(12) United States Patent
Nevalainen et al.

(10) Patent No.: US 7,306,921 B2
(45) Date of Patent: Dec. 11, 2007

(54) DIAGNOSTIC AND MONITORING METHODS FOR CANCER

(76) Inventors: Marja T. Nevalainen, 10740 Brewer House Rd., Rockville, MD (US) 20852; Hallgeir Rui, 10740 Brewer House Rd., Rockville, MD (US) 20852

( * ) Notice: Subject to any disclaimer, the term of this patent is extended or adjusted under 35 U.S.C. 154(b) by 544 days.

(21) Appl. No.: 10/376,286

(22) Filed: Mar. 3, 2003

(65) Prior Publication Data

US 2003/0224465 A1 Dec. 4, 2003

Related U.S. Application Data

(62) Division of application No. 09/760,899, filed on Jan. 17, 2001, now abandoned.

(51) Int. Cl.
*G01N 33/53* (2006.01)
(52) U.S. Cl. ...................................... 435/7.1
(58) Field of Classification Search ................ 436/64, 436/813; 424/130.1; 530/387.1
See application file for complete search history.

(56) References Cited

U.S. PATENT DOCUMENTS

| | | | |
|---|---|---|---|
| 5,244,787 A | 9/1993 | Key et al. | 435/7.9 |
| 5,578,452 A | 11/1996 | Shi et al. | 435/7.21 |
| 5,599,681 A | 2/1997 | Epstein et al. | 435/7.23 |
| 5,707,803 A | 1/1998 | Lamb et al. | 435/6 |
| 6,306,653 B1 * | 10/2001 | Papsidero et al. | 435/331 |

FOREIGN PATENT DOCUMENTS

| | | | |
|---|---|---|---|
| EP | 0 217 577 A2 | 4/1987 | |
| WO | WO 83/03679 | 10/1983 | |
| WO | WO 86/01533 | 3/1986 | |
| WO | WO 00/44774 | * 8/2000 | |

OTHER PUBLICATIONS

Waston et al. Br. J. Cancer, 1995, 71(4): 840-4.*
Ho et al., blood, 1999, 93(12): 4354-4364.*
Turkson et al., Oncogene 2000, 19:6613-6626.*
Bowman et al., Oncogene 2000, 19: 2474-2488.*
Bradshaw et al., Adv. Protein chem. 2002, 61: 161-210.*
Nishimura et al., Mol. Cell. Biol., 1993, 13(11): 6889-6896.*
Barber et al., Blood, 2001, 97(8): 2230-2237.*
Reich et al., Nature Reviews, Immunology, 2006, 6: 602-612.*
Allred, D.C. et al., "Prognostic and Predictive Factors in Breast Cancer by Immunohistochemical Analysis," *Mod. Pathol.* 11:155-168, The United States and Canadian Academy of Pathology, Inc. (1998).
Apantaku, L.M., "Breast Cancer Diagnosis and Screening ," *Am. Fam. Phnysician* 62:596-602, 605-606, American Academy of Family Physicians (Aug. 2000).
Ariyoshi, K. et al., "Constitutive Activation of STAT5 by a Point Mutation in the SH2 Domain," *J. Biol. Chem.* 275:24407-24413, The American Society for Biochemistry and Molecular Biology, Inc. (Aug. 2000).

Azam, M. et al., "Functionally Distinct Isoforms of STAT5 Are Generated by Protein Processing," *Immunity* 6:691-701, Cell Press (1997).
Barahmand-Pour, F. et al., "Jak2-Stat5 Interactions Analyzed in Yeast," *J. Biol. Chem.* 273:12567-12575, The American Society for Biochemistry and Molecular Biology, Inc. (1998).
Berg, K. et al., "Photochemical Internalization: A Novel Technology for Delivery of Macromolecules into Cytosol," *Cancer Res.* 59:1180-1183, Amercan Association for Cancer Research (1999).
Berois, N. et al., "Molecular detection of cancer cells in bone marrow and peripheral blood of patients with operable breast cancer. Comparison of CK19, MUC1 and CEA using RT-PCR," *Eur. J. Cancer* 36:717-723, Elsevier Science Ltd. (Apr. 2000).
Bishayee, A. et al., "Phosphorylation of Tyrosine 992, 1068 and 1086 Is Required for Conformational Change of the Human Epidermal Growth Factor Receptor C-Terminal Tail," *Mol. Biol. Cell* 10:525-536, The American Society for Cell Biology (Mar. 1999).
Boon, M.E. and Kok, L.P., "Microwaves for immunohistochemistry," *Micron* 25:151-170, Elsevier Science Ltd. (1994).
Braun, S. et al., "Cytokeratin-Positive Cells in the Bone Marrow and Survival of Patients with State I, II or III Breast Cancer," *N. Engl. J. Med.* 342:525-533, The Massachnusetts Medical Society (Feb. 2000).
Bridges. R.S., "The role of lactogenic hormones in maternal behavior in female rats," *Acta Paediatr. Suppl.* 397:33-39, Scandinavian University Press (1994).
Bromberg, J. and Darnell Jr., J.E., "The role of STATs in transcriptional control and their impact on cellular function," *Oncogene* 19:2468-2473, Macmillan Publishers Ltd. (May 2000).
Brown, C., "Antigen Retrieval Methods for Immunohistochemistry," *Toxicol Pathol.* 26:830-831, Society of Toxicologic Pathologist (1998).
Cardosi, R.J. and Fiorica, J.V., "Surveillance of the endometrium in tamoxifen treated women," *Curr. Opin. Obstet. Gynecol.* 12:27-31, Lippincott Williams & Wilkins (Feb. 2000).
Chen, J. et al., "Stat5 is a physiological substrate of the insulin receptor," *Proc. Natl. Acad. Sci. USA* 94:2295-2300, The National Academy of Sciences of the USA (1997).
Cochrane, D. et al., "Identification of Natural Ligand for SH2 Domains from a Phage Display cDNA Library," *J. Mol. Biol.* 297:89-97, Academic Press (Mar. 2000).

(Continued)

*Primary Examiner*—Christopher H. Yaen
*Assistant Examiner*—Hong Sang
(74) *Attorney, Agent, or Firm*—Conley Rose, P.C.

(57) ABSTRACT

The invention is directed to diagnostic and monitoring methods (assays) for cancer and kits that may be used in such methods. More particularly, an aspect of the invention relates to the use of activated Stat5 for diagnosing and monitoring breast cancer and predicting the effectiveness of cancer treatment. The invention also relates to the use of screening assays for discovering compounds that effect levels of activated Stat5.

20 Claims, 12 Drawing Sheets

OTHER PUBLICATIONS

Cole, P., "Major Aspects of the Epidemiology of Breast Cancer," *Cancer* 46:865-867, American Cancer Society (1980).

Cristiano, R.J., "Targeted, Non-Viral Gene Delivery for Cancer Gene Therapy," *Front. Biosci.* 3:D1161-D1170, Frontiers in Bioscience, Inc. (1998).

Dahiya, R. and Deng. G., "Molecular prognostic markers in breast cancer," *Breast Cancer Res. Treat.* 52:185-200, Kluwer Academic Publishers (1998).

Darnell Jr., J.E., "STATs and gene regulation," *Science* 277:1630-1635, The American Association for the Advancement of Science (1997).

Darnell Jr., J.E., "Studies of IFN-Induced Transcriptional Activation Uncover the Jak-Stat Pathway," *J. Interferon Cytokine Res.* 18:549-554, The Rockefeller University Press (1998).

Del Mastro, L. and Venturini, M., "Strategies for the Use of Epoetin Alfa in Breast Cancer Patients," *Oncologist* 3:314-318, AlphaMed press (1998).

Dente, L. et al., "Modified Phage Peptide Libraries as a Tool to Study Specificity of Phosphorylation and Recognition of Tyrosine Containing Peptides," *J. Mol. Biol.* 269:694-703, Academic Press Limited (1997).

Doi, N. and Yanagawa, H., "Screening of conformationally constrained random polypeptide libraries displayed on a protein scaffold," *Cell Mol. Life Sci.* 54:394-404, Birkhäuser Verlag (1998).

Doi, N. and Yanagawa, H., "STABLE: protein-DNA fusion system for screening of combinatiorial protein libraries in vitro," *FEBS Lett.* 457:227-230, Federation of European Biochemical Societies (1999).

Elledge, R.M. and McGuire, W.L., "Prognostic and Therapeutic Decisions in Axillary Node-Negative Breast Cancer," *Annu. Rev. Med.* 44:201-210, Annual Reviews, Inc. (1993).

Fata, J.E., et al., "The Osteoclast Differentiation Factor Osteoprotegerin-Ligand Is Essential for Mammary Gland Development," *Cell* 103:41-50, Cell Press (Sep. 2000).

Fetsch, P.A. et al., "Detection of Circulating Tumor Cells and Micrometastases in Stage II, III and IV Breast Cancer Patients Utilizing Cytology and Immunocytochemistry," *Diagn. Cytopathol.* 22:323-328, Wiley-Liss, Inc. (May 2000).

Fitzgibbons, P.L. et al., "Prognostic Factors in Breast Cancer. College of American Pathologists Consensus Statement 1999," *Arch. Pathol. Lab. Med.* 124:966-978, College of American Pathologists (Jul. 2000).

Freije, J.M. et al.. "Nm23 and tumour metastasis: basic and translational advances," *Biochem. Soc. Symp.* 63:261-271, Portland Press (1998).

Fresno, M. et al., "p53 Expression is of Independent Predictive Value in Lymph Node-Negative Breast Carcinoma," *Eur. J. Cancer* 33:1268-1274, Elsevier Science Ltd. (1997).

Gail, M.H. et al., "Weighing the Risks and Benefits of Tamoxifen Treatment for Preventing Breast Cancer," *J. Natl. Cancer Inst.* 91:1829-1846, Oxford University Press (1999).

Glockshuber, R. et al., "A Comparision of Strategies to Stabilize Immunoglulin $F_v$-Fragments," *Biochemistry* 29:1362-1367, American Chemical Society (1990).

Gouilleux, F. et al., "Prolactin induces phosphorylation of Tyr694 of Stat5 (MGF), a prerequisite for DNA binding and induction of transcription," *EMBO J.* 13:4361-4369, Oxford University Press (1994).

Gram, H. et al., "Identification of phosphopeptide ligands for the Src-homology 2 (SH2) domain of Grb2 by phage display," *Eur. J. Biochem.* 246:633-637, Federation of European Biochemical Societies (1997).

Gram, H., "Phage Display in Proteolysis and Signal Transduction," *Comb. Chem. High Throughput Screen* 2:19-28, Bentham Science Publishers B.V. (1999).

Grimley, P.M. et al., "Stat5a and Stat5b: fraternal twins of signal transduction and transcriptional activation," *Cytokine Growth Factor Rev.* 10:131-157, Elsevier Science Ltd. (1999).

Hanahan, D. and Weinberg, R.A., "The Hallmarks of Cancer," *Cell* 100:57-70, Cell Press (Jan. 2000).

Handwerger, S. and Freemark, M., "The Roles of Placental Growth Hormone and Placental Lactogen in the Regulation of Human Fetal Growth and Development," *J. Pediatr. Endocrinol. Metab.* 13:343-356, Freund Publishing House Ltd. (Apr. 2000).

Hankinson, S.E. et al., "Plasma Prolactin Levels and Subsequent Risk of Breast Cancer in Postmenopausal Women," *J. Natl. Cancer Inst.* 91:629-634, Oxford University Press (1999).

Hart, I.R. and Easty, D., "Tumor cell progression and differentiation in metastasis," *Semin. Cancer Biol.* 2:87-95, Academic Press (1991).

Haspel, R.L. and Darnell, Jr., J.E., "A nuclear protein tyrosine phosphatase is required for the inactivation of Stat1," *Proc. Natl. Acad. Sci. USA* 96:10188-10193, National Academy of Sciences (1999).

Horn, I.R. et al., "Selection of phage-displayed Fab antibodies on the active conformation of Ras yields a high affinity conformation-specific antibody preventing the binding of c-Raf kinase to Ras," *FEBS Lett.* 463:115-120, Federation of European Biochemical Societies (1999).

Huber, B.E., "Therapeutic opportunities involving cellular oncogenes: novel approaches fostered by biotechnology," *FASEB J.* 3:5-13, Federation of American Societies for Experimental Biology (1989).

Humphreys, R.C. and Hennighausen, L., "Signal Transducer and Activator of Transcription of 5a Influences Mammary Epithelial Cell Survival and Tumorigenesis," *Cell Growth Differ.* 10:685-694, American Association for Cancer Research (1999).

Humphreys, R. C. and Hennighausen, L., "Transforming growth factor alpha and mouse models of human breast cancer," *Oncogene* 19:1085-1091, Macmillan Publishers Ltd. (Feb.2000).

Igarashi, K. et al., "Sck Interacts with KDR and Flt-1 via Its SH2 Domain," *Biochem. Biophys. Res. Commun.* 251:77-82, Academic Press (1998)

Ikeda, N. et al., "Prognostic Significance of Occult Bone Marrow Micrometastases of Breast Cancer Detected by Quantitative Polymerase Chain Reaction for Cytokeratin 19 mRNA," *Jpn. J. Cancer Res.* 91:918-924, Japanese Cancer Association (Sep. 2000).

Illgen, K. et al., "Simulated molecular evolution in a full combinatorial library," *Chem. Biol.* 7:433-441, Elsevier Science Ltd. (May 2000).

Jones, F. E. et al., "ErbB4 Signaling in the Mammary Gland Is Required for Lobuloalveolar Development and Stat5 Activation during Lactation," *J. Cell Biol.* 147:77-88, The Rockefeller University Press (1999).

Kaplan, E. L. and Meier, P., "Nonparametic Estimation from Incomplete Observations," *Am. Stat. Assoc. J.* 53:457-481, American Statistical Association.

Kazansky, A.V. et al., "Differential Effects of Prolactin and scr/abl Kinases on the Nuclear Translocation of STAT5B and STAT5A," *J. Biol. Chem.* 274:22484-22492, American Society for Biochemistry and Molecular Biology (1999).

Kelly, M.A. et al., "Characterization of SH2-Ligand Interactions via Library Affinity Selection with Mass Spectrometric Detection," *Biochemistry* 35:11747-11755, American Chemical Society (1996).

Kinzler, K.W. and Vogelstein, B., "Lessons from Hereditary Colorectal Cancer," *Cell* 87:159-170, Cell Press (1996).

Kirken, R.A. et al., "Prolactin Stimulates Serine/Tyrosine Phosphorylation and Formation of Heterocomplexes of Multiple Stat5 Isoforms in Nb2 Lymphocytes." *J. Biol. Chem.* 272:14098-14103, American Society for Biochemistry and Molecular Biology (1997).

Kohler, G. and Milstein, C., "Continuous cultures of fused cells secreting antibody of predefined specificity," *Nature* 256:495-467, Macmillan Publishing Group (1975).

Kononen, J. et al., "Tissue microarrays for high-throughput molecular profiling of tumor specimens," *Nat. Med.* 4:844-847, Nature Publishing Group (1998).

Kouraklis, G., "Progress in Cancer Gene Therapy," *Acta Oncol.* 38:675-683, Scandinavian University Press (1999).

Kraeft, S.-K. et al., "Detection and Analysis of Cancer Cells in Blood and Bone Marrow Using a Rare Event Imaging System," *Clin. Cancer Res.* 6:434-442, American Association for Cancer Research (Feb. 2000).

Krenacs, L. et al., "Antigen Retrieval for Immunohistochemical Reactions in Routinely Processed Paraffin Sections," *Methods Mol. Biol. 115*:85-93, Humana Press Inc. (1999).

Lacronique, V. et al., "A TEL-JAK2 Fusion Protein with Constitutive Kinase Activity in Human Leukemia," *Science 278*:1309-1312, American Association for the Advancement of Science (1997).

Lamoyi, E. and Nisonoff, A., "Preparation of F(ab')₂ Fragments from Mouse IgG of Various Sublcasses," *J. Immunol. Methods 56*:235-243, Elsevier Biomedical Press (1983).

Lavabre-Bertrand, T. et al., "Quantitative immune phenotyping: a new dimension for the monitoring of haemopoietic malignancies," *Nouv. Rev. Fr. Hematol. 36*:373-382, Springer-Verlag (1994).

Lee, C. et al., "Characterization of the Stat5 Protease," *J. Biol. Chem. 274*:26767-26775, The American Society for Biochemistry and Molecular Biology, Inc. (1999).

Lengauer, C. et al., "Genetic instabilities in human cancers," *Nature 396*:643-649, Macmillan Publishing Group (1998).

Leonard, W.J. and O'Shea. J.J., "JAKS and STATS: Biological Implications," *Annu. Rev. Immunol. 16*:293-322, Annual Reviews Inc. (1998).

Liu, F. and Roth, R.A., "Grb-IR: a SH2-domain-containing protein that binds to the insulin receptor and inhibits its function," *Proc. Natl. Acad. Sci. USA 92*:10287-10291, The National Academy of Science (1995).

Liu, K. D. et al., "JAK/STAT signaling by cytokine receptors," *Curr. Opin. Immunol. 10*:271-278, Current Biology Ltd. (1998).

Liu, x. et al., "Cloning and expression of Stat5 and an additional homologue (Stat5b) involved in prolactin signal transduction in mouse mammary tissue," *Proc. Natl. Acad. Sci. USA 92*:8831-8835, The National Academy of Science (1995).

Liu, X. et al., "Stat5a is mandatory for adult mammary gland development and lactogenesis," *Genes Dev. 11*:179-186, Cold Spring Harbor University Press (1998).

Marks, L.B. and Prosnitz, L.R., "Lumpectomy With and Without Radiation for Early-Stage Breast Cancer and DCIS," *Oncology (Huntingt)* 11:1361-1368, 1371; discussion 1372, 1374, PRR Inc. (1997).

Marks, L.B. and Prosnitz, L.R., "The Role of Radiation Therapy After Local Excision of Invasive and Noninvasive Breast Cancer," *Surg. Oncol. Clin. N. Am. 6*:359-379, W.B. Saunders Inc. (1997).

Matthew, W.D. and Reichardt, L.F., "Development and Application of an Efficient Procedure for Converting Mouse IgM Into Small, Active Fragments," *J. Immunol. Methods 50*:239-253, Elsevier Biomedical Press (1982).

McGuire, W.L., "Breast Cancer Prognostic Factors: Evaluation Guidelines," *J. Natl. Cancer Inst. 33*:154-155, Oxford University Press (1991).

McGuire, W.L. et al., "Prognosis and Treatment Decisions in Patients with Breast Cancer without Axillary Node Involvement," *Cancer 70*:1775-1781, John Wiley & Sons, Inc. (1992).

McNicol, A.M. and Richmond, J.A., "Optimizing inummohistochemistry: antigen retrieval and signal amplification." *Histopathology 32*:97-103, Blackwell Science Limited (1998).

Meadowcroft, A.M. et al., "Cost of managing anemia with and without prophylactic epoetin alfa therapy in breast cancer patients receiving combination chemotherapy," *Am. J. Health Syst. Pharm. 55*:1898-1902, American Society of Health-System Pharmacists, Inc. (1998).

Messmer, B.T. et al., "Sequential Determination of Ligands Binding to Discrete Components in Heterogeneous Mixtures by Iterative Panning and Blocking (IPAB)," *J. Mol. Biol. 296*:821-832, Academic Press (Feb. 2000).

Meyer, J. et al. "Carboxyl-Truncated STAT5β Is Generated by a Nucleus-Associated Serine Protease in Early Hematopoietic Progenitors," *Blood 91*:1901-1908, The American Society of Hematology (1998).

Mighell, A.J. et al., "An overview of the complexities and subtleties of immunohistochemistry," *Oral Dis. 4*:217-223, Stockton Press (1998).

Moriggl, R. et al., "Stat5 Is Required for IL-2-Induced Cell Cycle Progression of Peripheral T Cells," *Immunity 10*:249-259, Cell Press (1999).

Morrison, S.L. et al., "Chimeric human antibody molecules: Mouse antigen-binding domains with human constant region domains," *Proc. Natl. Acad. Sci. USA 81*:6851-6855, The National Academy of Science (1984).

Morrow, M. t al., "Local Control Following Breast-Conserving Surgery for Invasive Cancer: Results of Clinical Trials," *J. Natl. Cancer Inst. 87*:1669-1673, Oxford University Press (1995).

"Update: *NCCN* Practice Guidelines for the Treatment of Breast Cancer," *Oncology (Huntingt)* 13:41-66, The National Comprehensive Cancer Network (1999).

Neuberger, M.S. et al., "Recombinant antibodies possessing novel effector functions," *Nature 312*:604-608. Macmillan Publishing Group (1984).

Nevalainen, M.T. et al., "Epithelial Defect in Prostates of Stat5a-null Mice." *Lab. Invest. 80*:993-1006, Lippincott Williams & Wilkins (Jul. 2000).

Noguchi, M. and Miyazaki, I., "Breast Conserving Surgery and Radiation in the Treatment of Operable Breast Cancer," *Int. Surg. 79*:142-147, International College of Surgeons (1994).

Noguchi, M. et al., "Breast-Conserving Treatment: Controversies and Consensus," *J. Surg. Oncol. 62*:228-234, Wiley-Liss, Inc. (1996).

Ohno, K. et al., "Cell-Specific, Multidrug Delivery System Using Streptavidin-Protein A Fusion Protein," *Biochem. Mol. Med. 58*:227-233, Academic Press, Inc. (1996).

Ohno, K. and Meruelo, D., "Multi-Drug Delivery System Using Streptavidin-Transforming Growth Factor-α Chimeric Protein," *DNA Cell Biol. 15*:401-406, Mary Ann Liebert, Inc. (1996).

Orr, R.K. et al., "The Learning Curve for Sentinel Node Biopsy in Breast Cancer: Practical Considerations," *Arch. Sur. 134*:764-767, American Medical Association (1999).

Panneerselvam, K. et al., "A Conformation-specific Anti-peptide Antibody to the β-type Platelet-derived Growth Factor Receptor Also Recognizes the Activated Epidermal Growth Factor Receptor," *J. Biol. Chem. 270*:7975-7979, The American Society for Biochemistry and Molecular Biology, Inc. (1995).

Parham, P. et al., "Monoclonal Antibodies: Purification, Fragmentation and Application to Structural and Functional Studies of Class I MHC Antigens," *J. Immunol . Methods 53*:133-173, Elsevier Biomedical Press (1982).

Parham, P., "On the Fragmentation of Monoclonal IgG1, IgG2a, and IgG2b From BALB/c Mice," *J. Immunol. 131*:2895-2902, The American Association of Immunologists (1983).

Parkin, D.M., "Epidemiology of cancer: global patterns and trends," *Toxicol. Lett. 102-103*:227-234, Elsevier Science Ireland Ltd. (1998).

Patterson, A. and Harris, A.L., "Molecular Chemotherapy for Breast Cancer," *Drugs Aging 14*:75-90, Adis International Limited (1999).

Pellegrini, M.C. et al., "Mapping the Subsite Preferences of Protein Tyrosine Phosphatase PTP-1B Using Combinatorial Chemistry Approaches." *Biochemistry 37*:15598-15606, American Chemical Society (1998).

Pharoah, P.D.P. et al., "Somatic mutations in the *p53* gene and prognosis in breast cancer: a meta-analysis," *Br. J. Cancer 80*:1968-1973, Cancer Research Campaign (1999).

Piazza, F. et al., "Myeloid differentiation of FdCP1 cells is dependent on Stat5 processing," *Blood 96*:1358-1365, The American Society of Hematology (Aug. 2000).

Prince. H.M., "Gene Transfer: A Review of Methods and Applications," *Pathology 30*:335-347, Royal College of Pathologists of Australia (1998).

Reid, I.M. and Donohue, J.H., "The Biological Significance of Locoregional Recurrence Following Breast Conserving Therapy," *Semin. Surg. Oncol. 8*:113-116, Wiley-Liss, Inc. (1992).

Rennie, I.G., "Clinically Important Ocular Reactions to Systemic Drug Therapy," *Drug Safety 9*:196-211, Adis International Limited (1993).

Rivadeneira, D.E. et al. "Predictive Factors Associated with Axillary Lymph Node Metastases in T1a and T1b Breast Carcinomas: Analysis in More Than 900 Patients," *J. Am. Coll. Surg. 191*:1-6; discussion 6-8, The American College of Surgeons (Jul. 2000).

Rousseaux, J. et al., "Optimal Conditions for the Preparation of Proteolytic Fragments from Monoclonal IgG of Different Rat IgG Subclasses," *Methods Enzymol. 121*:663-669, Academic Press, Inc. (1986).

Schnitt, S.J., "Can We Identify Patients with Invasive Breast Cancer Adequately Treated with Breast-Conserving Surgery Alone?" *Mod. Pathol. 11*:129-133, The United States and Canadian Academy of Pathology, Inc. (1998).

Schraml, P. et al., "Tissue Microarrays for Gene Amplification Surveys in Many Different Tumor Types," *Clin. Cancer Res. 5*:1966-1975, The American Association for Cancer Research (1999).

Shi, S.-R. et al., "Antigen Retrieval Immunohistochemistry: Past, Present, and Future," *J. Histochem. Cytochem. 45*:327-343, The Histochemical Society, Inc. (1997).

Simmons, R.M. and Osborne. M.P., "The evaluation of high risk and pre-invasive breast lesions and the decision process for follow up and surgical intervention," *Surg. Oncol. 8*:55-64, Elsevier Science Ltd. (1999).

Slamon, D.J. et al., "Human Breast Cancer: Correlation of Relapse and Survival with Amplification of the HER-2/*neu* Oncogene," *Science 235*:177-182, The American Association for the Advancement of Science (1987).

Spira, G. et al., "Generation of biologically active anti-*Cryptococcus neoformans* IgG, IgE and IgA isotype switch variant antibodies by acridine orange mutagenesis," *Clin. Exp. Immunol. 105*:436-442, Blackwell Science (1996).

Stebbing, J. et al., "Herceptin (trastuzamab) in advanced breast cancer," *Cancer Treat. Rev. 26*:287-290, Harcourt Publishers Ltd. (Aug. 2000).

Stoll, B.A., "Western diet, early puberty, and breast cancer risk." *Breast Cancer Res. Treat. 49*:187-193, Kluwer Academic Publishers (1998).

Styblo, T.M. and Wood, W.C., "the management of ductal and lobular breast cancer," *Surg. Oncol. 8*:67-75, Elsevier Science Ltd. (1999).

Sugg, S.L. et al., "Should Internal Mammary Nodes Be Sampled in the Sentinel Lymph Node Era?" *Ann. Surg. Oncol. 7*:188-192, The Society of Surgical Oncology, Inc. (Apr. 2000).

Taghian, A.G. and Powell, S.M., "The Role of Radiation Therapy for Primary Breast Cancer," *Surg. Clin. North Am. 79*:1091-1115, W.B. Saunders Company (1999).

Tandon, A.K. et al., "HER-2/*neu* Oncogene Protein and Prognosis in Breast Cancer," *J. Clin. Oncol. 7*:1120-1128, The American Society of Clinical Oncology (1989).

Teglund, S. et al., "Stat5a and Stat5b Proteins Have Essential and Nonessential, or Redundant, Roles in Cytokine Responses," *Cell 93*:841-850, Cell Press (1998).

Thammana, P. and Scharff, M.D., "Immunoglobulin heavy chain class switch from IgM to IgG in a hybridoma," *Eur. J. Immunol 13*:614-619, Verlag Chemie GmbH (1983).

Thomssen, C. et al., "Do we need better prognostic factors in nodenegative breast cancer?" *Eur. J. Cancer 36*:293-306. Elsevier Science Ltd. (Feb. 2000).

Tubiana, M., "Contribution of human data to the analysis of human carcinogenesis," *C. R. Acad. Sci. III 322*:215-224, Elsevier Science, Inc. (1999).

Udy, G.B. et al., "Requirements of STAT5b for sexual dimorphism of body growth rates and liver gene expression," *Proc. Natl. Acad. Sci. USA 94*:7239-7244, The National Academy of Science (1997).

Viens, P. et al., "Benefits of granulocyte-colony-stimulating factor after stem cell transfusion in intensive sequential chemotherapy for breast cancer," *Eur. Cytokine Netw. 9*:93-98, John Libbey Eurotext (1998).

Vomachka, A.J. et al., "Prolactin gene-disruption arrests mammary gland development and retards T-antigen-induced tumor growth," *Oncogene 19*:1077-1084, Macmillan Publishers Ltd. (Feb. 2000).

Wakao, H. et al., "Mammary gland factor (MGF) is a novel member of the cytokine regulated transcription factor gene family and confers the prolactin response," *EMBO J. 13*:2182-2191, European Molecular Biology Organization (1994).

Wang, D. et al., "Naturally Occurring Dominant Negative Variants of Stat5," *Mol. Cell Biol. 16*:6141-6148, American Society for Microbiology (1996).

Ward, E.S. et al., "Binding activities of a repertoire of a single immunoglobulin variable domains secreted from *Escherichia coli*," *Nature 341*:544-546, Macmillan Publishers, Inc. (1989).

Wartmann, M. et al., "Lactogenic Hormone Activation of Stat5 and Transcription of the β-Casein Gene in Mammary Epithelial Cells Is Independent of p42 ERK2 Mitogen-activated Protein Kinase Activity," *J. Biol. Chem. 271*:31863-31868, American Society for Biochemistry and Molecular Biology (1996).

Wellbrock, C. et al., "Signalling by the oncogenic receptor tyrosine kinase Xmrk leads to activation of STAT5 in *Xiphophorus melanoma*," *Oncogene 16*:3047-3056, Stockton Press (1998).

Welte, T. et al., "STAT5 Interaction with the T Cell Receptor Complex and Stimulation of T Cell Proliferation," *Science 283*:222-225, American Association for the Advancement of Science (1999).

Winter, G. and Milstein, C., "Man-made antibodies," *Nature 349*:293-299, Macmillan Publishers Inc. (1991).

Wu, N. and Ataai, M.M., "Production of viral vectors for gene therapy applications," *Curr. Opin. Biotechnol. 11*:205-208, Elsevier Science Ltd. (Apr. 2000).

Yamashita, H. et al., "Differential Control of the Phosphorylation State of Proline-juxtaposed Serine Residues $Ser^{725}$ of Stat5a and $Ser^{730}$ of Stat5b in Prolactin-sensitive Cells," *J. Biol. Chem. 273*:30218-30224, American Society for Biochemistry and Molecular Biology (1998).

Zhang, Z. et al., "Selection and application of peptide-binding peptides," *Nat. Biotechnol. 18*:71-74, Nature America Inc. (Jan. 2000).

Zhong, X.Y. et al., "Sensitive detection of micrometastases in bone marrow from patients with breast cancer using immunomagnetic isolation of tumor cells in combination with reverse transcriptase/polymerase chain reaction for cytokeratin-19," *J. Cancer Res. Clin. Oncol. 126*:212-218, Springer-Verlag (Apr. 2000).

Widschwendter, A., et al., "Prognostic Significance of Signal Transducer and Activator of Transcription 1 Activation in Breast Cancer," *Clin. Canc. Res. 8*:3065-3074, American Association for Cancer Research (Oct. 2002).

"Chapter 6 Table of Contents," and "Monoclonal antibodies are powerful immunochemical tools," in *Antibodies: A Laboratory Manual*, Harlow, E., and Lane, D., eds., Cold Spring Harbor Laboratory , Cold Spring Harbor, NY, pp. 139-142 (1988).

Nevalainen, M.T., et al., "Basal Activation of Transcription Factor Signal Transducer and Activator of Transcription (Stat5) in Nonpregnant Mouse and Human Breast Epithelium," *Mol. Endocrinol. 16*:1108-1124, The Endocrine Society (May 2002).

Zymed Laboratoreis, Inc., "Rabbit anti-phosphoSTAT5," *Zymed Catalog*, Catalog No. 71-6900 (2002).

* cited by examiner

PRL:    -    +

DIAGNOSTIC AND MONITORING METHODS FOR CANCER

CROSS-REFERENCE TO RELATED APPLICATIONS

This application is a divisional of U.S. patent application Ser. No. 09/760,899, filed on Jan. 17, 2001, now abandoned.

BACKGROUND OF THE INVENTION

1. Field of the Invention

The invention generally relates to diagnostic and monitoring methods and assays for cancer and kits that may be used in such methods. More particularly, the application relates to the use of activated Stat5 for diagnosing and monitoring cancer and predicting the prognosis of (breast) cancer patients and the outcome of cancer therapies, especially breast cancer. The invention also relates to screening assays for discovering compounds that affect levels of activated Stat5.

2. Related Art

One of the most pressing health issues today is diagnosing, monitoring and treating cancer and particularly breast cancer. Breast cancer is the leading form of cancer in women, and the second leading cause after lung cancer of cancer death among this population in the United States. In the industrialized world, about one woman in every nine can expect to develop breast cancer in her lifetime. In the United States, the annual incidence breast cancer is about 180,000 new cases and approximately 48,000 deaths each year (Parkin 1998; Apantaku 2000). Approximately two million women living in the United States alone have been diagnosed with breast cancer at some point in their lives. Breast cancer also occurs among men, though far more rarely (approximately 1,600 new cases diagnosed in the U.S. 1998). Treatment for male breast cancer is guided by our understanding of the disease in women.

Despite ongoing improvements in understanding the disease, breast cancer has remained to a large extent resistant to medical intervention. Most clinical initiatives are focused on early diagnosis, followed by conventional forms of intervention, particularly surgery, radiation, hormone suppression, and chemotherapy. Such interventions are of limited success, particularly in patients where the tumor has undergone metastasis. In patients with breast cancer without detectable lymph node metastases, socalled node negative breast cancer, the risk of death from breast cancer recurrence within 10 years is also high, approximately 30% (McGuire, Tandon et al. 1992). There is a pressing need to improve the arsenal of diagnostic tools and methods available to provide more precise and more effective information that will allow successful treatment in the least invasive way possible. Specifically, markers that can identify patients with very low risk of disease recurrence and death after initial surgery would reduce the extent of overtreatment with expensive and potentially toxic supplementary regimes. The invention meets that need by providing new methods and markers for monitoring breast cancer.

Breast Cancer

Development of cancer is a multistep process of genetic alterations that transform normal cells into highly malignant derivatives (Kinzler and Vogelstein 1996; Lengauer, Kinzler et al. 1998). Tumors within the breast may arise from any of its component tissues (e.g. connective tissue and epithelial structures). However, it is the epithelial tissue compartment that gives rise to most common malignant breast neoplasms.

A number of risk factors for carcinoma of the breast have been identified. These include: geographic influences, genetic predisposition, increasing age, length of reproductive life, parity, age at birth of first child, obesity, exogenous estrogens, fibrocystic changes with a typical epithelial hyperplasia and carcinoma of the contralateral breast or endometrium (Cole 1980; Stoll 1998). The chief forms of carcinoma of the breast are classified as infiltrating or noninfiltrating arising in the ducts. These include intraductal carcinoma, comedocarcinoma, simple or usual type (including scirrhous carcinoma), medullary carcinoma, colloid carcinoma, Paget's disease of the breast and tubular carcinoma. Infiltrating and noninfiltrating carcinomas also arise in the lobules and are referred to as in situ lobular carcinoma and infiltrating lobular carcinoma (Simmons and Osborne 1999; Styblo and Wood 1999).

Among the large group of breast cancer patients with localized tumors and without detectable metastases to nearby lymph nodes, many will be cured by surgery because the tumors have not spread to surrounding tissues and lymph nodes. However, others have occult micrometastatic disease and could benefit from supplementary radiation or adjuvant anti-hormone therapy or chemotherapy. There is a need for diagnostic markers to discriminate between tumors with low risk for micrometastatic spread and those with higher risk. Tumor markers that signify low risk of micrometastatic disease may directly affect the therapeutic decision of whether to use supplementary radiation or adjuvant hormone or chemotherapy. Furthermore, such tumor markers may also affect the surgeon's recommendation of whether to choose breast conserving surgery or mastectomy.

The molecular basis of cancer is still being determined. Underlying genome instability facilitates progressive accumulation of growth-promoting traits in premalignant cells under selective pressure from various growth barriers (Cahill et al 1999). Growth-promoting characteristics of cancer include self-sufficiency in growth signals, insensitivity to anti-growth signals, evasion of apoptosis, limitless replicative potential, sustained angiogenesis, tissue invasion and metastasis (Hanahan and Weinberg 2000). Associated with this stepwise progression of tumor cells toward increasing malignancy is a gradual loss of tissue-specific cell differentiation.

Loss of tumor cell differentiation appears to be particularly prominent at the transition from localized, surgically curable cancer to metastatic disease (Hart and Easty 1991; Freije, MacDonald et al. 1998; Rivadeneira, Simmons et al. 2000). This transition also is the single most critical determinant of prognosis for patients with solid tumors (McGuire 1991; Tubiana 1999). Assessment of the activity of transcriptional regulators that maintain cell and tissue-specific differentiation in primary tumors may therefore be useful for predicting the risk of occult micrometastases and tumor recurrence. Such informative tumor markers may directly influence treatment decisions by either providing prognostic distinction between low- and high-risk malignancies, or by predicting tumor response to specific adjuvant therapies or tumor response to specific modes of surgery (breast conservation surgery vs. mastetomy).

In breast cancer, receptors for estrogen and progesterone are related to the state of mammary epithelial cell differentiation and have prognostic value for disease outcome in certain cases. Estrogen and progesterone receptor (ER/PR) status is particularly useful as a predictive marker of positive response to adjuvant anti-estrogen therapy in node-positive breast cancer. However, the ER/PR status is not clinically useful to predict prognosis in node-negative cancer (Fitzgibbons, Page et al. 2000). This may be due to the high proportion of ER/PR positive, localized tumors. There is a need to identify low-risk breast cancer patients who may be spared from costly and potentially toxic adjuvant antiestrogen treatment or chemotherapy. There is also a need to identify low-risk breast cancer patients who may benefit from less invasive procedures such as breast conserving surgery, or lumpectomy, with or without post-surgical radiation therapy, instead of mastectomy. The benefits of less extensive and less invasive therapeutic regimes to patients with good prognosis may include avoidance of side-effects, improved mental and physical health, improved quality of life, and lower financial burden. The benefits to society are particularly the cost-saving aspects of avoiding unnecessary overtreatment. One means of accomplishing this is to obtain better prognostic markers for node-negative, as well as other types of breast cancer. These needs are met by the invention.

Diagnosis of Breast Cancer

The definitive diagnosis of all types of breast disease is based on histologic evaluation of tissue samples using the light microscope. The histologic criteria used to define most breast lesions are historic but nonetheless quite reproducible for identifying fully invasive breast cancers.

Improved detection and screening routines, and the development and increasing utilization of fine needle aspirates (FNAs) and core needle biopsies for obtaining tissue samples have been major advances in both detection and diagnosis. Stereotactic image guidance of needle biopsies has tremendously improved our ability to sample suspicious lesions, particularly non-palpable masses, as small as a few millimeters in diameter nearly anywhere in the breast. This has dramatically increased the detection of small, more treatable breast cancers and decreased unnecessary surgery in an enormous number of patients with insignificant benign disease. Recent accomplishments include the identification of a small number of tissue-based biomarkers that are helpful in predicting clinical outcome and response to therapy (e.g., S-phase fraction, estrogen and progesterone receptors, c-erbB-2) and the discovery of genes (BRCA-1 and BRCA-2) associated with familial risk for breast cancers (Dahiya and Deng 1998; Fitzgibbons, Page et al. 2000).

However, diagnosing breast cancer still requires some type of biopsy procedure. In addition, current diagnostic and prognostic methods cannot absolutely distinguish breast cancers that are treatable by surgery alone from those that are likely to recur or have already spread through micrometastases. As a result, at least 50 percent of breast cancer patients with node negative disease are treated with some form of adjuvant therapy. Moreover, available methods are inadequate for predicting the response of breast cancers to specific types of adjuvant therapies.

Treatment decisions for individual breast cancer patients are frequently based on the number of axillary lymph nodes involved with disease, estrogen receptor and progesterone receptor status, size of the primary tumor, and stage of disease at diagnosis (Tandon, Clark et al. 1989). However, even with this variety of factors, it is currently not possible to predict accurately the course of disease for all breast cancer patients. There is clearly a need to identify new markers in order to separate patients with good prognosis, who might need no supplementary therapy beyond surgical removal of the malignant breast tumor, from those whose cancer is more likely to recur and who might benefit from additional and more exhaustive treatment forms.

Despite extensive efforts over several decades, only a limited number of immunohistochemical breast tumor markers have been identified. Among immunohistochemical markers, hormone receptor status remains the only to have gained standard clinical use for evaluating node-negative breast tumors (Fitzgibbons, Page et al. 2000). With improving methods for screening and detection of early breast cancer the proportion of node-negative cases is expected to continue to rise (Elledge and McGuire 1993). Parameters that have been established to be important for the prognosis of patients with breast malignancies in general and that are used by clinicians include: size of primary tumor, stage of disease at diagnosis, number of axillary lymph nodes involved with disease, and hormonal receptor status (ER/PR) (Fitzgibbons, Page et al. 2000). Abnormal status of ErbB-2 or p53, as well as other histological and genetic markers, also are associated with poor prognosis especially in node-positive tumors (Slamon, Clark et al. 1987; Fresno, Molina et al. 1997; Pharoah, Day et al. 1999).

In this regard, U.S. Pat. No. 5,599,681 has suggested the use of an antibody that specifically binds to a reversible phosphorylation site of the c-erbB2 oncoprotein in its active form to screen for the metastatic potential of tumors in patients with node-negative breast cancer. Nowhere, however, was it suggested that screening for activated Stat5 could be used to predict the metastatic potential of breast cancer.

There remain deficiencies in the art with respect to the identification of markers linked with the progression of breast cancer, the development of diagnostic methods to monitor disease progression and the development of therapeutic methods and compositions; to treat breast diseases and cancers. The identification of markers which are differentially expressed or activated in breast cancer would be of considerable importance in the development of a rapid, inexpensive method to improve diagnosing of breast cancer and to predict tumor behavior with respect to patient prognosis and responsiveness to individual therapeutic options. The identified marker(s) would also be useful as a target of therapeutic compositions, of in screening assays for therapeutic compounds.

The diagnostic and monitoring methods of the invention meet many needs in this area.

Therapeutic Regimes for Treating Breast Cancer

Treatment of breast cancer is multifaceted and complex. The choice of therapeutic approach is guided by a series of criteria based on a limited set of tumor characteristics. Nearly all patients with breast cancer will have some type of surgery. This may be supplemented by local therapy with radiation, or by systemic therapy including hormone suppression or chemotherapy. To kill cancer cells that may have spread beyond the breast and nearby tissues, physicians employ oral or intravenous systemic therapy. Examples of systemic treatments for breast cancer are chemotherapy and antiestrogen therapy. Systemic therapy given to patients after surgery is often referred to as adjuvant therapy. The goal of adjuvant therapy is to kill hidden cancer cells. Even in the early stages of the disease cancer cells can break away from the primary breast tumor and spread through the bloodstream. These cells usually cause no detectable symptoms and usually do not show up on an x-ray and cannot be felt during a physical examination. But they can establish new tumors in other locations in the body. Furthermore, oncologists sometimes give patients neo-adjuvant therapy—that is, systemic therapy before surgery, typically to shrink the tumor.

The following summarizes the main principles of treatment of breast cancer according to current guidelines endorsed by the U.S. National Cancer Consortium Network and the American Cancer Society (1999). The text below maintains an emphasis on treatment of node-negative breast cancer, as it relates to the present invention.

Breast conserving surgery—"Lumpectomy" removes only the breast lump and the surrounding area, or margin, of normal tissue. If cancer cells are present at the margin (the edge of the excisional biopsy or lumpectomy specimen), a re-excision can usually be done to remove the remaining cancer. In most cases, lumpectomy is combined with 6 to 7 weeks of supplementary radiation therapy following surgery. This combination of lumpectomy and radiation is often referred to as "breast conserving therapy".

Mastectomy—In a "simple (total) mastectomy" procedure surgeons remove the entire breast but do not remove any lymph nodes from under the arm, or muscle tissue from beneath the breast. In a "modified radical mastectomy", surgeons remove the entire breast and some of the axillary (underarm) lymph nodes. Modified radical mastectomy is the most common surgery for patients with breast cancer in whom doctors remove the whole breast. "Radical mastectomy" removes not only the entire breast, but axillary lymph nodes and the chest wall muscles under the breast as well. The less extensive modified radical mastectomy has proved as effective as radical mastectomy, which is nowadays rarely performed due to disfiguration and frequent side-effects.

Lymph node surgery—Regardless of whether a breast cancer patient has a mastectomy, or a lumpectomy for invasive cancer, the physicians need to determine whether the cancer has spread. The regional lymph nodes in the underarm drain lymph from the breast, and are typically the first sites of spread. Furthermore, lymph node involvement increases the likelihood that cancer cells have spread through the blood-stream to other parts of the body.

While lymph node surgery itself does not improve the chance for a cure, this is the only way to accurately determine if the cancer has spread to the lymph nodes. This usually means removing some or all of the lymph nodes in the armpit. Typically 10 to 20 lymph nodes in the armpit are examined by an operation called "axillary lymph node dissection". Although axillary lymph node dissection is a safe procedure with low rates of serious side effects, efforts are ongoing to develop new ways of detecting the spread of cancer to lymph nodes that are less invasive and do not involve a full lymph node dissection. Such alternative methods include the "sentinel lymph node biopsy" (Orr, Hoehn et al. 1999; Sugg, Ferguson et al. 2000), and new detection methods for breast cancer cells in bone marrow and blood (Berois, Varangot et al. 2000; Braun, Pantel et al. 2000; Fetsch, Cowan et al. 2000; Ikeda, Miyoshi et al. 2000; Kraeft, Sutherland et al. 2000; Zhong, Kaul et al. 2000). It is possible that these newer methods in the future may replace lymph node dissection as a means of determining micrometastatic spread of cancer.

Sentinel lymph node biopsy—In the sentinel lymph node biopsy procedure the surgeon finds and removes the 'sentinel node'—the first lymph node into which a tumor drains, and therefore the one most likely to contain cancer cells. Many doctors recommend it for most women with breast cancer, but others still consider it investigational. In a sentinel lymph node biopsy the surgeon injects a radioactive substance and/or a blue dye into the area around the tumor. Lymphatic vessels carry these materials into the sentinel node. The doctor can either see the blue dye or detect the radioactivity with a geiger counter, and then cuts out the node for examination. If the sentinel node contains cancer, the surgeon will have to perform an axillary dissection—removal of more lymph nodes in the axilla (armpit). If the sentinel node is cancer-free, the patient and her physicians may consider avoiding more lymph node surgery and its potential side effects. Although the sentinel node procedure is relatively new and its long-term effectiveness is uncertain (Orr, Hoehn et al. 1999; Sugg, Ferguson et al. 2000), it may turn out to be equally as effective in determining lymph node spread as full lymph node dissection.

Detection of disseminated cancer cells in blood and bone marrow—Recent methods for detecting metastatic breast cancer cells in blood (Berois, Varangot et al. 2000; Fetsch, Cowan et al. 2000; Kraeft, Sutherland et al 2000) or in bone marrow (Braun, Pantel et al. 2000; Ikeda, Miyoshi et al. 2000; Zhong, Kaul et al. 2000) are typically based on the detection of cytokeratin markers characteristic to breast cancer cells by immunological methods or by gene-based testing. These new methods may also lead to an alternative approach to lymph node dissection for determining whether a breast cancer has spread beyond the local tumor area.

Radiation therapy—Radiation is used to destroy cancer cells left behind in the breast, chest wall, or lymph nodes after surgery. Radiation treatments usually take place 5 days a week over a period of 6 to 8 weeks. Side effects most likely to occur include swelling and heaviness in the breast, sunburn-like skin changes in the treated area, and fatigue. Changes to the breast tissue and skin usually go away in 6 to 12 months. In some women, the breast becomes smaller and firmer after radiation therapy. Radiation therapy of axillary (armpit area) lymph nodes can also cause lymphedema. Although generally safe, it is evident that radiation therapy comes at a considerable expense and with potentially serious side-effects. Radiation therapy also involves a major risk for abnormal fetal development, and cannot be used to treat pregnant women with breast cancer.

New tumor markers that signify good prognosis may reduce the need for supplementary radiation therapy.

Chemotherapy—Patients receive this treatment of anti-cancer drugs intravenously (injected into a vein) or by mouth. Either way, the drugs travel in the bloodstream and move throughout the entire body. Doctors who prescribe these drugs (medical oncologists) generally use a combination of medicines proven more effective than a single drug. For women with node-negative breast cancer the most frequently used chemotherapy options are CMF (cyclophosphamide, methotrexate, and fluorouracil), CAF (cyclophosphamide, doxorubicin), and AC (doxorubicin (Adriamycin) and cyclophosphamide) (1999). Doctors give chemotherapy in cycles, with each period of treatment followed by a recovery period. The total course of chemotherapy usually lasts 3 to 6 months depending on the combinations used. This is significant both in terms of cost and reduced well-being. The side effects of chemotherapy are many and potentially severe, and depend on the type of drugs used, the amount taken, and the length of treatment. Doxorubicin and epirubicin may cause heart damage, although doctors limit the dose and perform periodic tests to check heart function in order to prevent this side effect. Other side effects include loss of appetite, nausea and vomiting, mouth sores, hair loss, and changes in the menstrual cycle. Because chemotherapy can damage the blood-producing cells of the bone marrow, a drop in white blood cells can raise a patient's risk of infection, a shortage of blood platelets can cause bleeding or bruising after minor cuts or injuries; and a decline in red blood cells can lead to fatigue due to anemia.

New tumor markers that identify patients with excellent prognosis may eliminate the need for adjuvant chemotherapy among these patients.

Hormone therapy—Estrogen, a female sex hormone produced by the ovaries, promotes growth of some breast cancers. Doctors use several approaches to block the effect of estrogen or to lower estrogen levels. The most commonly used antiestrogen drug is tamoxifen, taken daily in pill form, usually for 5 years. Studies show that tamoxifen can reduce the chances of breast cancer coming back after surgery if the breast cancer cells contain receptors for estrogen or progesterone. Tamoxifen may be used to treat metastatic breast cancer, but also a significant number of patients with node-negative cancer receive tamoxifen treatment.

Adjuvant Herceptin therapy—A new form of adjuvant breast cancer treatment involves the use of Herceptin, a drug that antagonizes activity of the Her2/neu oncogene reecently introduced for select patients with node-positive breast cancer (Stebbing, Copson et al. 2000). Herceptin therapy will not be discussed in more detail here.

Therapeutic considerations in node-negative breast cancer—Decisions about types of surgery (breast conserving lumpectomy, radical mastectomy), radiation therapy, adjuvant chemotherapy or hormonal therapy are currently based on the status of axillary lymph nodes, the size of the malignant tumor and its histologic type (appearance under a microscope), and hormone receptor status. For example, if regional lymph nodes are negative (do not contain any cancer cells) and the tumor measures half a centimeter or smaller, the patient needs no adjuvant (post-surgery) therapy. In current practice, a substantial number of patients with node-negative breast cancer with larger tumors receive adjuvant therapies with questionable benefit in terms of relatively limited improvement in prognosis considering the associated increased morbidity and serious side-effects (McGuire, Tandon et al. 1992). These adjuvant therapies also come at high cost as described above. Furthermore, the choice of the less invasive breast conserving surgery (lumpectomy) is generally preferred by doctors and patients over mastectomy, but more specific guidelines and better prognostic tumor markers are needed to guide this selection. There is therefore a strong need for new markers to identify breast cancer patients with low risk for disease recurrence and death.

Markers for low-risk cancer and patient follow-up—Better prognostic tumor markers may also have the benefit of reducing the frequency of follow-up visits among patients with low-risk cancer. Tumor markers identifying low-risk breast cancer patients may also allow reduced frequency and lighten the extensive requirements for patient follow-up. While this is primarily a cost issue, it also positively impacts the patient's quality of life. Routine surveillance and follow-up for all patients who have had invasive breast cancer curently includes the following: a history and physical exam every 4-6 months for 2 years, then every 6 months for 3 years, and then, once every year (1999). Women who have had a lumpectomy and radiation (breast conservation therapy) should undergo mammography of the treated breast at 6 months after radiation therapy, and then mammography of both breasts on an annual basis. Women who have had a mastectomy should get a mammogram of the remaining breast annually after the surgery. Because tamoxifen increases a postmenopausal woman's risk of developing cancer of the endometrium (lining of the upper part of the uterus), postmenopausal patients taking this drug also should have an annual pelvic exam. Markers indicating low-risk for tumor recurrence therefor may benefit both patients and society by reduced costs associated with fewer and less extensive follow-up examinations.

Monitoring of recurrent breast cancer—Work-up for a suspected recurrence of breast cancer includes a biopsy to confirm the first recurrence whenever possible. A recurrence may be local, meaning that cancer has returned to the breast, underarm lymph nodes, or nearby tissues, or systemic, which means that cancer has spread to distant organs. There exist a series of guidelines to treat locally recurring breast cancer. The current recommendations for treatment of the locally recurring tumor depend in large part on what mode of treatment was used for the original tumor (1999). New markers that predict the biological behavior of breast cancer may affect the choice of follow-up therapy, depending on whether the recurrent tumor is deemed low or high risk. For instance, local recurrence of a tumor positive for a marker indicating low risk of distant spread may allow the use of less intensive therapeutic approaches than if the tumor is negative for this same marker. For example, reexcision and possibly local radiation may suffice instead of radical mastectecomy with or without adjuvant chemotherapy or anti-hormone therapy.

Stat5

The Signal Transducer and Activator of Transcription (STAT) family of transcription factors provide a signaling link between cell surface hormone and cytokine receptors and specific response elements in the promoters of selective genes. Seven mammalian STAT genes have been identified. The Stat5 transcription factor is involved in regulation of cell growth, differentiation, and cell survival (Wakao, Gouilleux et al. 1994). It exists as two highly homologous isoforms, Stat5a and 5b, which have more than 95% amino acid homology and are encoded by separate genes (Liu, Robinson et al. 1995; Grimley, Dong et al. 1999). Stat5 is required for normal mammary epithelial cell development and differentiation (Liu, Robinson et al. 1997; Udy, Towers et al. 1997; Moriggl, Topham et al. 1999).

Stat5 polypeptides typically are cytoplasmic and quiescent under homeostatic conditions. Their activation results from phosphorylation of the highly conserved C-terminal tyrosine at Tyr694 in Stat5a or the corresponding Tyr699 in Stat5b by certain intracellular tyrosine kinases. This phosphorylation permits dimer pair formation which is needed for Stat5 to bind to DNA.

This initial phosphotyrosyl "on-switch" is a generic Stat feature (Darnell 1997; Darnell 1998) and is triggered when cells with cognate receptors are exposed to a variety of stimuli including cytokines, immune complexes, microbiologic agents or non-peptidyl compounds. Although the spectrum of agonists thus is heterogeneous, the bulk implicated in triggering Stat5 activation belong to the class I and class II cytokine superfamilies. (See Table 4 of (Grimley, Dong et al. 1999). These cytokines utilize receptors lacking a catalytic domain (Liu, Gaffen et al. 1998), so that the Stat activation is most often dependent upon an auxiliary protein kinase (Leonard and O'Shea 1998).

The Janus tyrosine kinases (Jaks) form biochemically stable associations with class I and class II cytokine receptors. A non-covalent linkage facilitates Jak phosphorylations during receptor ligation and increases the odds of interactions between Jaks and Stat5 recruited to receptor-Jak complexes (Leonard and O'Shea 1998). This critical and conserved mutual relationship has engendered the scientific vernacular of "Jak-Stat pathway" (Liu, Gaffen et al. 1998). However, Jaks are not the sole means of Stat activation.

Stat5a and Stat5b can also be tyrosine phosphorylated by a number of cytokines commonly designated as "growth factors" which bind to receptor tyrosine kinases (RTKs). The RTKs possess intrinsic catalytic properties, and may trigger Stat5 signals absent a direct linkage to the Jak enzyme system (Chen, Sadowski et al. 1997). In addition, Stat5 tyrosine phosphorylation might be effected by cytosolic protein kinases in the Src or Tec families. As "nonreceptor tyrosine kinases" (NTKs), the latter enzymes can function without extrinsic stimulation due to receptor ligation. The Src-family kinase Lck has been implicated in Stat5 phosphorylation during T cell proliferation (Welte, Leitenberg et al. 1999) and constitutively active NTKs, RTKs or analogous oncoproteins may be particularly significant in maintaining a constitutive phosphorylation of Stat5 in autonomously proliferating neoplastic cells (For example, See (Lacronique, Boureux et al. 1997; Wellbrock, Geissinger et al. 1998)).

In addition to the initial activation switch of Stat5, which involves phosphorylation of a tyrosine residue within a conserved C-terminal segment and causes dimerization of Stat5 molecules (Gouilleux, Wakao et al. 1994), a second coordinated activation event is required for functional activation. This involves translocation of dimerized Stat5 from the cytoplasm into the cell nucleus, which permits Stat5 to come in proximity of and bind to gene regulatory promoter elements, and thus regulate transcription of specific genes (Gouilleux, Wakao et al. 1994; Kazansky, Kabotyanski et al. 1999). Because Stat5 not only requires phosphorylation of a specific tyrosine residue, but also needs to translocate into the cell nucleus in order to function as an active DNA-binding transcription factor, amounts of tyrosine phosphorylated Stat5 located within the cell nucleus will reflect the levels of activated Stat5 more accurately than overall cellular levels of tyrosine phosphorylated Stat5. For instance, tyrosine phosphorylation of Stat5a by the Src tyrosine kinase has been shown not to be accompanied by nuclear translocation (Kazansky, Kabotyanski et al. 1999), illustrating that quantitation of tyrosine phosphorylation status alone without assessing nuclear localization is not sufficient for accurate determination of levels of activated Stat5. Correspondingly, Stat transcription factors may become dephosphorylated within the cell nucleus and loose the ability to bind to DNA (Haspel and Darnell 1999), making assays that detect nuclear Stat5 protein levels alone also not sufficient for accurate determination of levels of activated Stat5. In the present description, the term 'levels of activated Stat5' refers to levels of tyrosine phosphorylated Stat5 within the cell nucleus.

Antibodies that bind exclusively to tyrosine phosphorylated Stat5 can be used to detect activated Stat5 in the nuclei of cells by immunocytochemistry or immunohistochemistry, provided that proper steps are taken to achieve antigen retrieval of this cryptic antigenic site. This antigenic site is cryptic, or unavailable, unless the phosphorylated tyrosine bound to the SH2 domain of the partner molecule in the dimer is dissociated by specific treatment.

Detection of active, tyrosine phosphorylated Stat5 by immunohistochemistry in tissue sections has been reported (Jones, Welte et al. 1999). Stat5 activation in normal mouse mammary gland tissue in response to Erb-B4 activation was studied. However, human breast tissue or human breast cancer samples were not examined. In further contrast to Jones, the current invention may use a simple one-step antigen-retrieval method for determining levels of activated Stat5.

The extent to which Stat5 promotes cell proliferation or inhibits growth by inducing cell differentiation in various tissues, including mammary gland, is unresolved. The possibility that Stat5 activation status is of prognostic value for breast cancer was not obvious prior to the inventors' discovery, because a priori, it had been argued that Stat5 activation may promote mammary tumor formation instead of being associated with reduced risk of invasion and metastasis.

It was specifically suggested that a general anti-apoptotic effect of Stat5 might contribute to mammary tumor progression in rodents (Humphreys and Hennighausen 2000). This notion was supported by the observation that in mice lacking the Stat5a gene (Stat5a−/− mice) but overexpressing the oncogenic TGF-alpha transgene, the rate of mammary tumor formation was reduced relative to that observed in Stat5a+/+ mice (Humphreys and Hennighausen 1999)). This suggested that the Stat5a transcription factor promotes mammary tumor formation. Likewise, a positive role for Stat5 in mammary carcinogenesis indirectly has been indicated by the reduced mammary tumor formation in mice lacking the gene for prolactin, a major activator of Stat5 in mammary epithelial cells (Vomachka, Pratt et al. 2000), as well as the observation that circulating prolactin levels correlated with increased risk of breast cancer in post-menopausal women (Hankinson, Willett et al. 1999). Furthermore, the notion of a tumorigenic role of Stat5 in the mammary gland (Humphreys and Hennighausen 1999; Humphreys and Hennighausen 2000) would be consistent with the prevailing view of a tumor-promoting role of Stat5 in hematopoietic cancer (lymphomas, leukemias) (Wellbrock, Geissinger et al. 1998; Bromberg and Darnell 2000).

Alternatively, it could be argued that Stat5 activation may suppress breast tumor formation by acting as a growth-inhibitory differentiation factor for mammary epithelial cells. Likewise, Stat5 regulates normal differentiation of ovaries and prostate (Teglund, McKay et al. 1998; Moriggl, Topham et al. 1999; Nevalainen, Ahonen et al. 2000). However, there is currently no direct evidence available demonstrating a role of Stat5 as a tumor suppressor in either breast or other tissues. Therefore, the present invention and description of activated Stat5 as a marker of good prognosis in node-negative human breast cancer was unexpected based on the published literature and prevailing views within the scientific field. As such, the role of Stat5 in human breast cancer development and progression had not been established, and its use as a marker of biologic behavior of human breast tumors had not been reported.

SUMMARY OF THE INVENTION

It has been discovered by the inventors that activated Stat5 within human primary breast tumors correlates with reduced risk of death from breast cancer and reduced risk of metastatic disease. This correlation was particularly strong for node-negative breast cancer. Such a correlation was not known or even suspected prior to the inventors' discovery. Therefore, nuclear, activated Stat5 is a new and novel prognostic marker of breast cancer.

The presence of nuclear, activated Stat5 in human breast cancer indicates a higher degree of differentiation of the tumor and is also associated with an increased survival rate within this patient population. Activated Stat5 levels in the primary tumor of node negative breast cancer patients is a strong positive prognostic factor independent of other known prognostic markers, as evidenced by multivariate Cox regression analysis.

Levels of activated, nuclear Stat5 may be analyzed with antibodies or other binding probes. Thus, the analysis of activated Stat5 adds a new level of information to current breast cancer markers and is a reliable prognostic molecular/biochemical marker of cancer in samples from untreated breast cancer patients. Additionally, monitoring levels of activated Stat5 should be predictive of the outcome of Stat5-targeted therapeutic strategies.

The invention involves the use of activated Stat5 as a tumor marker that predicts the risk/prognosis and biological behavior of breast cancer. The inventors describe a straightforward method to determine Stat5 activation status in histological tissue sections of tumors by immunohistochemistry. In this regard, analysis of nuclear, activated Stat5 levels, by univariate Cox regression analysis can also be used as a predictive measure of a positive outcome of antiestrogen treatment. Furthermore, it may also be predictive of the success of other treatments where alterations in Stat5 activation levels are involved, as well as predictive of success of breast conserving surgery and radical mastectomy.

The invention is first directed to a diagnostic or monitoring method comprising: a) obtaining a sample of tissue from an individual in need of diagnosis or monitoring for cancer; b) detecting levels of activated Stat5 antigen in said sample; c) scoring said sample for activated Stat5 levels; and d) comparing said scoring to that obtained from a control tissue sample to determine the prognosis associated with said cancer. Cancers that may be diagnosed or monitored include but are not limited to breast cancer, ovarian cancer, endometrial cancer, thyroid cancer, prostate cancer, colorectal cancer, hematopoietic cancer, and skin cancer.

The invention is further directed to a diagnostic or monitoring method comprising: a) obtaining a sample of breast tissue from an individual in need of diagnosis or monitoring for breast cancer; b) detecting levels of activated Stat5 antigen in said sample; c) scoring said sample for activated Stat5 levels; and d) comparing said scoring to that obtained from a control breast sample to determine the prognosis associated with said breast cancer. Preferably, the cancer is a node negative breast cancer.

The invention is also directed to a diagnostic or monitoring method comprising: a) obtaining a sample from an individual in need of diagnosis or monitoring for breast cancer; b) contacting said sample with an antibody or binding probe that detects activated Stat5; c) detecting or measuring the level of activated Stat5; and d) comparing the level of activated Stat5 to that obtained from a control breast sample.

In all aspects of the invention a preferable embodiment involves contacting the sample of interest with an antibody to tyrosine-phosphorylated Stat5. Preferably the detecting is done on histological or tissue sections or cytological preparations by immunohistochemistry or immunocytochemistry. Additionally, detecting of activated Stat5 in the methods of the invention may be done by immunoblotting or by Fluorescence-Activated Cell Sorting (FACS).

The invention is also directed to a method for screening compounds comprising: a) obtaining compounds to be screened for use in breast cancer therapy; b) contacting a cell or tissue sample with said compound; and c) determining the effect of said compound on the level of Stat5 activation in said cell or tissue sample relative to a control sample. Preferably the cell or tissue sample is cells or tissue from a breast cancer. Additionally, in the method of the invention the effect of said compound may be determined by the binding of an antibody to activated Stat5 to said sample relative to control cells or tissue. Also preferably in the method said activated Stat5 is tyrosine-phosphorylated Stat5 found in the cell nucleus.

The invention is further directed to a method for screening compounds comprising: a) obtaining compounds to be screened for altering Stat5 activation levels, b) contacting a cell or tissue of interest with said compounds, c) determining the effect of said compound on the level of activated Stat5 in said cell or tissue sample relative to a control sample.

The invention is also directed to a method for screening compounds comprising: a) obtaining compounds to be screened for use in cancer therapy; b) contacting a cell or tissue sample with said compound; and c) determining the effect of said compound on the level of Stat5 activation in said cell or tissue sample. Preferably the cell or tissue sample is from a human cancer. The effect of said compound may be determined by the binding of an antibody to activated Stat5 to said sample relative to control cells or tissue. Preferably said activated Stat5 is tyrosine-phosphorylated Stat5 found in the cell nucleus.

The invention is also directed to a method for screening compounds comprising: a) obtaining compounds to be screened for their ability to positively or negatively affect Stat5 activation; b) contacting a relevant cell or tissue sample with said compound; and c) determining the effect of said compound on the level of Stat5 activation in said cell or tissue sample. Preferably the effect of said compound may be determined by the binding of an antibody to activated Stat5 to said sample relative to control cells or tissue. Also preferably said activated Stat5 is tyrosine-phosphorylated Stat5 found in the cell nucleus.

The invention is also directed to a method for determining the effect of antiestrogen treatment comprising: a) obtaining a cell or tissue sample from an individual in need of antiestrogen treatment, b) measuring the levels of activated Stat5 in said cell or tissue sample; and c) comparing said levels to that of a control breast cancer sample to predict the responsiveness to antiestrogen treatment.

The invention is also directed to a method for determining the efficacy of breast conserving surgery (lumpectomy) for treatment of node-negative breast cancer comprising: a) obtaining a cell or tissue sample from an individual in need of breast conserving surgery, b) measuring the levels of activated Stat5 in said cell or tissue sample; and c) comparing said levels to that of a control breast cancer sample to predict the responsiveness of said breast cancer to breast conserving surgery.

The invention is further directed to a kit for determining the level of activated Stat5 in a mammalian biological sample, wherein said activated Stat5 is an indicator of the prognosis of breast cancer, said kit comprising: a) an antibody or binding probe to activated Stat5, b) a reagent useful for detecting the extent of interaction between said antibody or binding probe and activated Stat5; c) a reagent or solution useful for antigen retrieval; and c) positive and/or negative control samples. The kit of invention may include a monoclonal or polyclonal antibody as the antibody. This antibody may be directly linked to an indicator reagent, wherein said indicator reagent is selected from the group consisting of fluorescent, colorimetric, immunoperoxidase and isotopic reagents. Alternatively, the kit may further include a second indicator antibody linked to an indicator reagent, wherein said indicator reagent is selected from the group consisting of fluorescent, calorimetric, immunoperoxidase and isotopic reagents.

The invention is further directed to a method for diagnosing a pathological condition or a susceptibility to a pathological condition comprising: a) obtaining a sample from an individual in need of diagnosis for a pathological condition related to activity of Stat5, b) determining the amount or presence of activated Stat5 in said sample; and c) diagnosing said pathological condition or a susceptibility to said pathological condition based on the presence or amount of activated Stat5 relative to a control sample.

Any of the methods of the claimed invention may use either univariate or multivariate Cox regression analysis or Kaplan-Meyer survival analysis with log-rank statistics for analyzing the obtained results or may analyze a sample in a tissue section, isolated cell, or isolated nuclei (smears, cytological sample or flow cytometry.) The methods of the invention may further comprise analyzing the levels of activated Stat5 in conjunction with additional breast cancer markers.

The invention is further directed to a diagnostic or monitoring method comprising: a) obtaining a sample of breast tissue from an individual in need of diagnosis or monitoring for breast cancer; b) treating said sample in a microwave oven or by other forms of heat based antigen retrieval methods; c) detecting levels of activated Stat5 antigen in said sample; d) scoring said samples for activated Stat5 levels; and e) comparing said scoring to that obtained from a control breast sample to determine the prognosis associated with said breast cancer. In addition to heat based antigen retrieval methods, other methods known in the art for antigen retrieval may also be used.

The invention is further directed to a diagnostic or monitoring method comprising: a) obtaining a sample of breast tissue from an individual in need of diagnosis or monitoring for breast cancer, b) treating said sample with an antigen-retrieval buffer, c) detecting levels of activated Stat5 antigen in said sample; d) scoring said samples for activated Stat5 levels; and e) comparing said scoring to that obtained from a control breast sample to determine the prognosis associated with said breast cancer. Preferably said antigen retrieval solution is an aqueous buffer about pH 7 to about pH 10, such as for example Phosphate Buffered Saline at pH 7.4. Most preferably, the antigen retrieval solution is about 1 mM Tris having about a pH 10.

The invention is further directed to a method for predicting disease-free survival and overall survival in patients with node-negative breast cancer comprising: a) obtaining a sample of breast cancer tissue from an individual with node-negative breast cancer; b) detecting levels of activated Stat5 antigen in breast cancer cells or breast cancer tissue of said sample; c) scoring said samples for activated Stat5 levels; and d) comparing said scoring to that obtained from a control breast sample to determine likelihood of disease-free survival and overall survival associated with said breast cancer.

Any of the methods of the invention may score the analysis by using a scale of 0 to 4, where 0 is negative (no detectable activated Stat5 in cell nuclei), and 4 is high intensity staining in the majority of cell nuclei and wherein a score of 1 to 4 (i.e. a positive score) indicates a better prognosis for disease free and overall survival in patients with node-negative breast cancer.

The invention is also directed to a method for predicting disease-free survival and overall survival in patients who have not received adjuvant hormone or chemotherapy comprising: a) obtaining a sample of breast tissue from an individual with breast cancer who has not received adjuvant hormone or chemotherapy, b) detecting levels of activated Stat5 antigen in breast cells or breast tissue of said sample, c) scoring said sample for activated Stat5 levels; and d) comparing said scoring to that obtained from a control breast sample to determine the likelihood of disease-free survival and overall survival associated with said breast cancer.

The invention is further directed to a method for treating breast cancer comprising: a) obtaining a sample of breast tissue from a patient in need of treatment of breast cancer, b) determining the level of activated Stat5 in said breast tissue sample, c) treating said patient with a therapeutic regime known to improve the prognosis for breast cancer, d) repeating steps "a" and "b", e) adjusting the therapeutic regime based on the determination of the activated Stat5 levels and f) repeating steps a-e as frequently as deemed appropriate.

The invention is further directed to a method for screening for metastatic potential of breast tumors comprising: a) obtaining a sample of breast tissue from an individual in need of screening for metastatic potential of a breast tumor, b) reacting an antibody to activated Stat5 with tumor tissue from said patient, c) detecting the extent of binding of said antibody to said tissue and d) correlating the extent of binding of said antibody with its metastatic potential Preferably, the tumor is a node-negative breast cancer.

The invention is further directed to a method for screening for metastatic potential of solid tumors comprising: a) obtaining a sample of tumor tissue from an individual in need of screening for metastatic potential of a solid tumor; b) reacting an antibody to activated Stat5 with tumor tissue from said patient; c) detecting the extent of binding of said antibody to said tissue and d) correlating the extent of binding of said antibody with its metastatic potential. Preferably, the tumor is a node-negative cancer arising from the ovary, large bowel (colorectal cancer), uterus (endometrial cancer), thyroid gland, prostate, or skin.

Any of the methods of the invention involving analysis of the levels of activated Stat5 may be used in conjunction with additional breast cancer markers readily known to those of skill in the art.

The invention is further directed to a monoclonal antibody, wherein said antibody a) is generated against the phosphopeptide KAVDG(phospho Y)VKPOIK (SEQ ID NO: 1); b) specifically recognizes tyrosine phosphorylated isoforms of Stat5, but not unphosphorylated isoforms; c) does not recognize Stat5 mutants in which the Tyr694 residue has been substituted with phenylalanine; and d) recognizes phosphorylated Stat5 following an antigen retrieval treatment that does not use a protease.

DETAILED DESCRIPTION OF THE PREFERRED EMBODIMENTS

Definitions

Figure 1:
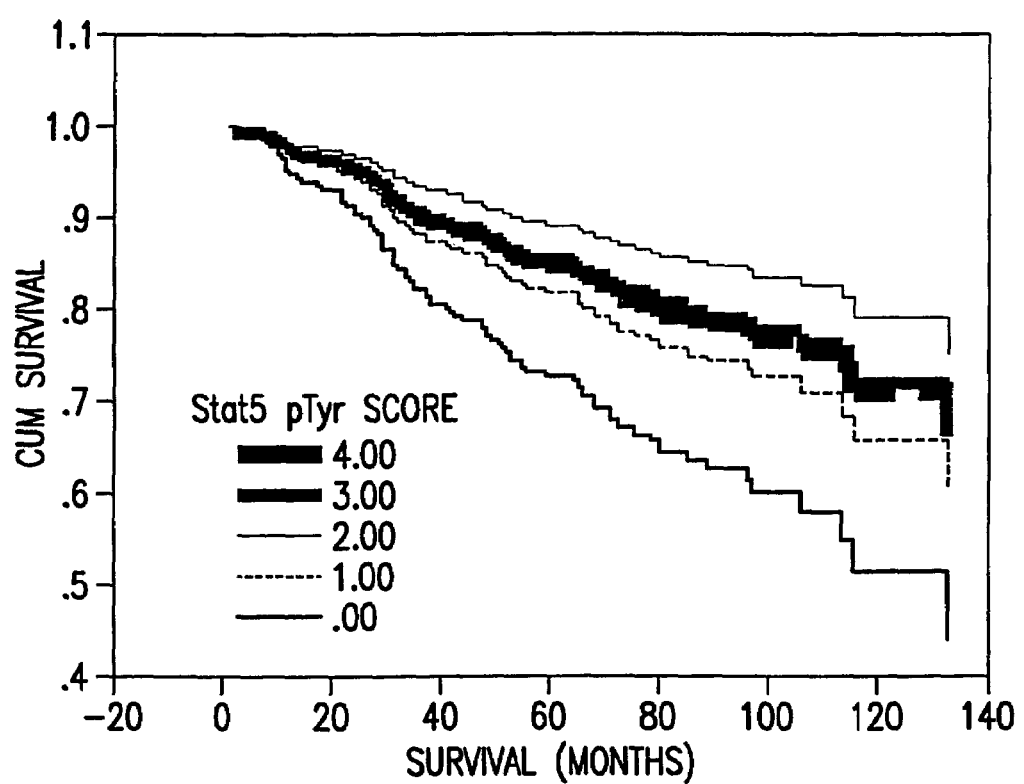
FIG. 1—Cutpoint analysis of scores quantifying levels of activated Stat5. The effect of various levels of activated Stat5 on overall survival of breast cancer patients is shown. Patients with primary tumors with no detectable level of activated Stat5 (Score 0) has significantly lower rates of overall survival than patients with detectable levels of activated Stat5 in their tumors (Scores 1-4). However, no significant difference was noted between scores 1-4 in terms of overall survival rate. Scores 1-4 were therefore recoded into a single categorical parameter ("Positive Stat5 activation status"), whereas score 0 was given the designation "negative Stat5 activation status".

In order to provide a clearer understanding of the specification and claims the following definitions are provided.

The terms a and an should be understood to refer to at least "one" item, but are not limited to reference to only "one", unless such is specifically indicated. Thus, for example, reference to "a" cell refers to one or more cells.

Activated Stat5—Activated Stat5 is Stat5 that is detected in the cell nucleus in the tyrosine phosphorylated form. Tyrosine phosphorylated Stat5 has been reported to exist in a dimeric structural configuration that is capable of binding to specific DNA sequences. Activated Stat5 may include Stat5a and Stat5b isoforms, gene products, and/or posttranslationally modified variants thereof, such as for example proteolytically truncated forms (Wang, Stravopodis et al. 1996; Azam, Lee et al. 1997; Kirken, Malabarba et al. 1997; Meyer, Jucker et al. 1998; Grimley, Dong et al. 1999; Lee, Piazza et al. 1999; Piazza, Valens et al. 2000).

Stat5 is activated by two distinct, sequential events. The initial activation switch of Stat5 involves phosphorylation of a tyrosine residue within a conserved C-terminal segment that causes dimerization of Stat5 molecules (Gouilleux, Wakao et al. 1994). A second coordinated activation event involves translocation of dimerized Stat5 from the cytoplasm into the cell nucleus, which permits Stat5 to bind to gene regulatory promoter elements and regulate transcription of specific genes (Gouilleux, Wakao et al. 1994; Kazansky, Kabotyanski et al. 1999). Because Stat5 not only requires phosphorylation of a specific tyrosine residue, but also needs to translocate into the cell nucleus in order to function as an active DNA-binding transcription factor, amounts of tyrosine phosphorylated Stat5 located within the cell nucleus will more accurately reflect the levels of activated Stat5 than overall cellular levels of tyrosine phosphorylated Stat5. For instance, aberrant tyrosine phosphorylation of Stat5a by hyperactive Src tyrosine kinase has been shown not to be accompanied by nuclear translocation (Kazansky, Kabotyanski et al. 1999). This observation illustrates that quantitation of tyrosine phosphorylation status alone without assessing nuclear localization is not sufficient for accurate determination of levels of activated Stat5. Correspondingly, Stat transcription factors may become dephosphorylated within the cell nucleus and loose the ability to bind to DNA (Haspel and Darnell 1999), making assays that detect nuclear Stat5 protein levels alone also not sufficient for determining levels of activated Stat5. The definition of activated Stat5 therefore refers to both nuclear localization and tyrosine phosphorylation.

Alternatively, antibodies or binding reagents that specifically detect Stat5 in its active, dimerized (structural) configuration may also be used to detect Stat5 that has become phosphorylated and translocated to the cell nucleus. For description of such conformation-specific antibody-derivatives that may not bind directly to a phosphorylation site but still detect the active form of other effector molecules, including cellular oncogenes Ras and receptors for epidermal growth factor and platelet-deriverd growth factor, see (Panneerselvam, Reitz et al. 1995; Bishayee, Beguinot et al. 1999; Horn, Wittinghofer et al. 1999). Detection of activated, nuclear Stat5 is used to predict the biological behavior of breast tumors and may also be useful for diagnosing or monitoring other pathological conditions involving changes in the activation state and expression levels of Stat5, including other forms of cancer.

Antibody—An "antibody" (interchangeably used in plural form) is an immunoglobulin molecule capable of specific binding to a target, such as a polypeptide, through at least one antigen recognition site. As used herein, the term encompasses not only intact antibodies, but also fragments thereof, mutants thereof, fusion proteins, humanized antibodies, and any other modified configuration of the immunoglobulin molecule that comprises an antigen recognition site of the required specificity. An antibody against activated Stat5 is used in the methods of the invention.

Antigen—The term "antigen" refers to the target molecule that is specifically bound by an antibody through its antigen recognition site, such as for example, the activated Stat5 antigen. The antigen may, but need not be chemically related to the immunogen that stimulated production of the antibody. The antigen may be polyvalent, or it may be a monovalent hapten. Examples of different kinds of antigens that can be recognized by antibodies include polypeptides, polynucleotides, other antibody molecules, oligosaccharides, complex lipids, drugs, and chemicals. An "immunogen" is an antigen capable of stimulating production of an antibody when injected into a suitable host, usually a mammal.

Compounds may be rendered immunogenic by many techniques known in the art, including crosslinking or conjugating with a carrier to increase valency, mixing with a mitogen to increase the immune response, and combining with an adjuvant to enhance presentation.

Antigen Retrieval Reagent—An "antigen retrieval reagent" facilitates and/or allows binding of immunostaining reagents with epitopes masked by formalin-fixation, by natural binding moieties, or by structural constraints such as protein folding, or any combination of these factors. Antigen retrieval reagents can be used alone or in combination with other physical or physicochemical procedures such as heating or microwave treatment (Boon and Kok 1994; Fresno, Molina et al. 1997; Shi, Cote et al. 1997; Brown 1998; McNicol and Richmond 1998; Mighell, Hume et al. 1998; Krenacs, Krenacs et al. 1999).

Such a reagent expands the range of antibodies useful in immunohistochemistry as well as reduces the incidence of false negative staining in over-fixed tissues. Methods of antigen retrieval are known in the art such as described, for example, in U.S. Pat. Nos. 5,244,787 and 5,578,452 and in (Boon and Kok 1994; Fresno, Molina et al. 1997; Shi, Cote et al. 1997; Brown 1998; McNicol and Richmond 1998; Mighell, Hume et al. 1998; Krenacs, Krenacs et al. 1999).

Any embodiment of the invention may use an antigen-retrieval buffer of about 1 mM Tris at a pH of about 10.

Binding Probe—Binding probes are not antibody-based (immunoglobulin based) but still bind with high specificity and affinity to an antigen or antigenic site. For instance, following routine molecular engineering methods such as those set forth in (Ausubel 1988; Sambrook, Maniatis et al. 1989), those skilled in the art may develop a binding probe containing the Stat5 SH2 (src-homology-2) domain, which is known to bind with high affinity and specificity to the tyrosine-phosphorylated Stat5 molecule (Liu and Roth 1995; Igarashi, Shigeta et al. 1998; Ariyoshi, Nosaka et al. 2000). Such a binding probe could contain one (monovalent) or several (mulitivalent) Stat5 SH2 domains. This binding probe could be engineered or chemically modified to contain detection label, which could consist of isotope, fluorescence, enzyme or one or more antigenic sites or "tags" to be recognized by secondary antibodies, which in turn may have similar detection labels attached. Thus a non-antibody based binding probe could be generated that is able to specifically detect activated Stat5 that is tyrosine phosphorylated and present in the cell nucleus.

Rational genetic engineering, random mutagenesis, or targeted molecular evolution in vitro may lead to Stat5-SH2 domains with improved binding characteristics (Ariyoshi, Nosaka et al. 2000). Alternatively, peptide-based binding probes may be generated from scratch by selection of random chemical or genetic libraries for interaction with Stat5 in its activated, dimeric conformation, for example by binding to tyrosine phosphorylated Stat5. General approaches to selection of these types of binding probes have been described by numerous authors (Kelly, Liang et al. 1996; Dente, Vetriani et al. 1997; Gram, Schmitz et al. 1997; Doi and Yanagawa 1998; Pellegrini, Liang et al. 1998; Doi and Yanagawa 1999; Gram 1999; Cochrane, Webster et al. 2000; Illgen, Enderle et al. 2000; Messmer, Benham et al. 2000; Zhang, Zhu et al. 2000).

Cancer Cell—The terms "cancerous cell" or "cancer cell", used either in the singular or plural form, refer to cells that have undergone a malignant transformation that makes them pathological to the host organism. Malignant transformation is a single- or multi-step process, which involves in part an alteration in the genetic makeup of the cell and/or the gene expression profile. Malignant transformation may occur either spontaneously, or via an event or combination of events such as drug or chemical treatment, radiation, fusion with other cells, viral infection, or activation or inactivation of particular genes. Malignant transformation may occur in vivo or in vitro, and can if necessary be experimentally induced. Malignant cells may be found within the well-defined tumor mass or may have metastasized to other physical locations.

A feature of cancer cells is the tendency to grow in a manner that is uncontrollable by the host, but the pathology associated with a particular cancer cell may take any form. Primary cancer cells (that is, cells obtained from near the site of malignant transformation) can be readily distinguished from non-cancerous cells by well-established pathology techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells.

Cell line—A "cell line" or "cell culture" denotes higher eukaryotic cells grown or maintained in vitro. It is understood that the descendants of a cell may not be completely identical (either morphologically, genotypically, or phenotypically) to the parent cell. Cells described as "uncultured" are obtained directly from a living organism, and have been maintained for a limited amount of time away from the organism: not long enough or under conditions for the cells to undergo substantial replication.

Clinical Sample—It is understood that a "clinical sample" encompasses a variety of sample types obtained from a subject and useful in the procedure of the invention, such as for example, a diagnostic or monitoring test of activated Stat5 levels. The definition encompasses solid tissue samples obtained by surgical removal, a pathology specimen, an archived sample, or a biopsy specimen, tissue cultures or cells derived therefrom and the progeny thereof, and sections or smears prepared from any of these sources. Non-limiting examples are samples obtained from breast tissue, lymph nodes, and breast tumors. The definition also encompasses blood, bone marrow, spinal fluid, and other liquid samples of biologic origin, and may refer to either the cells or cell fragments suspended therein, or to the liquid medium and its solutes.

Control Sample—A control sample is a source of cells or tissue for comparison purposes. A control sample may include, inter alia, cancer-free breast or mammary tissue or an archived pathology sample containing activated Stat5 at various levels for use as positive control, and breast tumor tissue or other tissue showing no Stat5 activation as negative control samples.

Diagnostic Method—A "diagnostic method" may include, but is not limited to determining the metastatic potential of a tumor or determining a patient's prognosis following discovery of a breast tumor. Such diagnostic methods may also be used for determining the effectiveness of a therapeutic regime used to treat cancer or other disease involving the presence of activated Stat5. An example of such a therapeutic treatment is antiestrogen treatment for breast cancer. The terms "diagnostic method" or "monitoring method" are often used interchangeably.

Differential Result—A "differential" result is generally obtained from an assay in which a comparison is made between the findings of two different assay samples, such as a cancerous cell line and a control cell line or a cancerous tissue and a control tissue. Thus, for example, "differential levels" of a marker protein, such as Stat5 are observed when the level of Stat5 is higher in one tissue sample than another.

Disease-Free Survival—"Disease-free survival" should be understood to mean living free of the disease being monitored. For example, if activated Stat5 is used to diagnose or monitor breast cancer, disease-free survival would mean free from detectable breast cancer.

Metastatic Potential—Metastasis refers to the condition of spread of cancer from the organ of origin to additional sites in the patients. Therefore, "metastatic potential" as it relates to for example, breast cancer may be considered to be the risk of progression of primary node-negative cancer from localized disease to disseminated, metastatic disease.

Monitoring Method—A "monitoring method" may include, but is not limited to, following a patient's progress or response to a therapeutic regime after discovery of a breast tumor. Such monitoring methods may also be used for determining the effectiveness of a therapeutic regime used to treat cancer or other diseases involving the presence of activated Stat5. An example of such a therapeutic treatment is antiestrogen treatment for breast cancer. Antibodies to activated Stat5 are used in monitoring methods of this invention. The terms "diagnostic method" or "monitoring method" are often used interchangeably.

Node Negative Breast Cancer—"Node negative breast cancer" is breast cancer that is localized to the breast without detectable metastasis to nearby lymph nodes, thereby indicating a low risk for recurrence of the cancer after surgery of the primary tumor.

Pathology—The "pathology" caused by cancer cells within a host is anything that compromises the well-being or normal physiology of the host. This may involve, but is not limited to abnormal or uncontrollable growth of the cancer cell, metastasis, release of cytokines or other secretory products at an inappropriate level, manifestation of a function inappropriate for its physiological milieu, interference with the normal function of neighboring cells, aggravation or suppression of an inflammatory or immunological response, or the harboring of undesirable chemical agents or invasive organisms.

Pharmaceutical Candidate—A "pharmaceutical candidate" or "drug candidate" is a compound believed to have therapeutic potential, that is to be tested for efficacy against a specific condition, such as for example a condition having altered activated Stat5 levels (such as breast cancer). The "screening" of a pharmaceutical candidate refers to conducting an assay that is capable of evaluating the efficacy and/or specificity of the candidate. In this context, "efficacy" refers to the ability of the candidate to affect Stat5 activation levels and/or affect the cell or organism it is administered to in a beneficial way: for example, the limitation of the pathology of cancerous cells.

Prognosis—"Prognosis" as used in this application means the likelihood of recovery from a disease or the prediction of the probable development or outcome of a disease. For example, if a sample from a patient with breast cancer is positive for nuclear staining with an antibody to activated Stat5, then the "prognosis" for that patient is better than if the sample was negative for activated Stat5 staining. Samples may be scored for activated Stat5 levels on a scale from 0-4 for levels of antibody staining, where 0 is negative and 1-4 represents positive staining at four semiquantitative steps of increasing intensity. Scores 1-4 can be recoded as positive because each positive score was associated with significantly reduced risk for relapse and fatal disease when compared to score 0 (negative), but increasing intensity among the positive scores did not provide additional risk reduction. Cox semiparametric proportional hazard analysis can be used to estimate the prognostic value of activated Stat5. Cutpoint analysis has shown that scores 1-4 differ significantly from 0 in terms of predicting overall survival among node-negative breast cancer patients, but did not differ significantly from each other (See FIG. 1). Additional refinement of the quantification procedure may reveal a better quantitative relationship with the prognosis. The term positive or negative "Stat5 activation status" of tumors used in this description refers to scores 0 or scores 1-4, respectively.

The prognosis of a patient with breast cancer may be based, inter alia, at least in part on the metastatic potential of the breast cancer and a relationship to activated Stat5 levels. This description is not meant to limit the basis for the determination of a patient's prognosis, because those of skill in the art would be aware of other related bases for determination of the prognosis.

Relative Amount—The term "relative amount" is used where a comparison is made between a test measurement and a control measurement. Thus, the relative amount of a reagent forming a complex in a reaction is the amount reacting with a test specimen, compared with the amount reacting with a control specimen. The control specimen may be run separately in the same assay, or it may be part of the same sample (for example, normal tissue surrounding a malignant area in a tissue section).

Scoring—A sample may be "scored" during the diagnosis or monitoring of breast cancer. In its simplest form, scoring may be categorical negative or positive as judged by visual examination of samples by immunohistochemistry. More quantitative scoring involves judging the two parameters intensity of staining and the proportion of stained ("positive") cells that are sampled. Based on these two parameters numbers may be assigned that reflect increasing levels of positive staining. Allred et al (Allred, Harvey et al. 1998) have described one way of achieving this, which involved scoring both parameters on a scale from 0 (negative) to 4, and summarizing the scores of the individual parameters to an overall score. This results in a scale with possible scores of 0, 2, 3, 4, 5, 6, 7 or 8. (Note that a score of 1 is not possible on Allred's scale). A somewhat simpler scoring method integrates the intensity of nuclear staining and the proportion of cells that display stained nuclei into a combined scale from 0 to 4. In practice, the scores 7 and 8 of Allred's scale correspond to 4 on the simplified scale. In the same way, scores 5 and 6 correspond to 3, scores 3 and 4 to score 2, score 2 corresponds to 1, and, 0 corresponds to 0 on both scales. Either scoring method may be applied to scoring intensity and proportion of staining of activated Stat5 in the cell nuclei. The terms positive or negative "Stat5 activation status" of tumors used in the present description refers to levels of activated Stat5 that correspond to scores 0 or 1-4 on the simplified scale, respectively.

Treatment—"Treatment" of an individual or a cell is any type of intervention in an attempt to alter the non-treated course of the individual or cell. For example, treatment of an individual may be undertaken to decrease or limit the pathology caused by a cancer harbored in the individual. Treatment includes but is not limited to a) administration of a composition, such as a pharmaceutical composition, b) administration of a surgical procedure (such as lumpectomy or modified radical mastectomy), or c) administration of radiation therapy, and may be performed either prophylactically, subsequent to the initiation of a pathologic event or contact with an etiologic agent.

Tyrosine-phosphorylated Stat5—"Tyrosine-phosphorylated Stat5" refers to Stat5a phosphorylated on amino acid residue Tyr694 or Stat5b phosphorylated on the homologous amino acid residue Tyr699. This tyrosine phosphorylation causes the Stat5 molecules to dimerize, and is critical for the ability of Stat5 to bind to DNA. Tyrosine phosphorylated Stat5 is therefore equated with activated Stat5, although only tyrosine phosphorylated Stat5 that is found in the nucleus may strictly reflect properly activated Stat5. Tyrosine phosphorylated Stat5 that remains located in the cytoplasm is not functionally activated in the sense that it remains unable to interact with DNA in the cell nucleus and regulate gene transcription.

Diagnostic Antibodies

The present invention relates to the use of antibodies against activated Stat5, antibody fragments against activated Stat5 and Stat5 binding probes. Examples of binding probes that may be used to detect activated Stat5 that are not antibody or immunoglobulin based include proteins derived from the phosphotyrosyl-binding SH2 (src-homology-2) domain of Stat5 (Wakao, Gouilleux et al. 1994; Ariyoshi, Nosaka et al. 2000), or binding proteins that have been selected for their ability to bind to activated Stat5 by using screening methods for large chemical or molecular libraries similar to those described in the literature (Kelly, Liang et al. 1996; Dente, Vetriani et al. 1997; Gram, Schmitz et al. 1997; Igarashi, Shigeta et al. 1998; Cochrane, Webster et al. 2000). The principles for development of such binding reagents have been described in detail for other binding probes, and provide means for those skilled in the art to use similar approach to develop probes that bind to activated Stat5. Further elaboration is now provided for terms related to diagnostic antibodies and assays.

"Fragment" is defined as at least a portion of the variable regions of the immunoglobulin molecule which binds to its target, i.e. the antigen binding region. Some of the constant region of the immunoglobulin may be included.

"Antigen-binding region" means that part of the antibody, the fusion protein, or the immunoconjugate of the invention which recognizes the target or portions thereof "Directly" means the use of antibodies coupled to a label. The specimen is incubated with the labeled antibody, unbound antibody is removed by washing, and the specimen may be examined.

"Indirectly" means incubating the specimen with an unconjugated antibody, washing and incubating with a marker-conjugated antibody. The marker may be a fluorochrom, enzyme, isotope, metal, etc. The second or "sandwich" antibody thus reveals the presence of the first.

The term "Stat5 antibody" as used herein includes whole, intact polyclonal and monoclonal antibody materials, and chimeric antibody molecules. The Stat5 antibody described above may include any fragments thereof containing the active antigen-binding region of the antibody such as Fab, F(ab')2 and Fv fragments, using techniques well established in the art (see, e.g., (Rousseaux, Rousseaux-Prevost et al. 1986)). The Stat5 antibody used in the invention also includes fusion proteins.

In addition, the present invention encompasses use of antibodies that are capable of binding to the same antigenic determinant as the activated Stat5 antibodies and competing with the antibodies for binding at that site. These include antibodies having the same antigenic specificity as the Stat5 antibodies but differing in species origin, isotype, binding affinity or biological functions (e.g., cytotoxicity). For example, class, isotype and other variants of the antibodies of the invention having the antigen-binding region of the Stat5 antibody can be constructed using recombinant class-switching and fusion techniques known in the art (see, e.g., (Thammana and Scharff 1983; Neuberger, Williams et al. 1984; Spira, Paizi et al. 1996).

One skilled in the art will appreciate that the invention also encompasses the use of immunoglobulin fragments that retain recognition of the antigen. Such immunoglobulin fragments may include, for example, the Fab', F(ab')2, F(v) or Fab fragments, or other antigen recognizing immunoglobulin fragments. Such immunoglobulin fragments can be prepared, for example, by proteolytic enzyme digestion, using enzymes such as pepsin or papain, reductive alkylation, or recombinant techniques. The materials and methods for preparing such immunoglobulin fragments are well-known to those skilled in the art. See generally, (Matthew and Reichardt 1982; Parham, Androlewicz et al. 1982; Lamoyi and Nisonoff 1983; Parham 1983).

An immunoglobulin can be a "chimeric antibody" as that term is recognized in the art. Also, the immunoglobulin may be a "bifunctional" or "hybrid" antibody, that is, an antibody which may have one arm having a specificity for one antigenic site, such as a tumor associated antigen while the other arm recognizes a different target, for example, a hapten which is, or to which is bound, an agent lethal to the antigen-bearing tumor cell. Alternatively, the bifunctional antibody may be one in which each arm has specificity for a different epitope of a tumor associated antigen of the cell to be therapeutically or biologically modified. In any case, the hybrid antibodies have a dual specificity, preferably with one or more binding sites specific for the hapten of choice or one or more binding sites specific for a target antigen, for example, an antigen associated with a tumor, an infectious organism, or other disease state.

Biological bifunctional antibodies are described, for example, in European Patent Publication, EPA 0 105 360, to which those skilled in the art are referred. Such hybrid or bifunctional antibodies may be derived, as noted, either biologically, by cell fusion techniques, or chemically, especially with cross-linking agents or disulfide bridge-forming reagents, and may be comprised of whose antibodies and/or fragments thereof Methods for obtaining such hybrid antibodies are disclosed, for example, in PCT application WO83/03679 and published European Application EPA 0 217 577. Particularly preferred bifunctional antibodies are those biologically prepared from a "polydome" or "quadroma" or which are synthetically prepared with cross-linking agents such as bis-(maleimideo)-methyl ether ("BMME"), or with other cross-linking agents familiar to those skilled in the art.

In addition the immunoglobin may be a single chain antibody ("SCA") These may consist of single chain Fv fragments ("scFv") in which the variable light ("V(L)") and variable heavy ("V(H)") domains are linked by a peptide bridge or by disulfide bonds. Also, the immunoglobulin may consist of single V(H) domains (dAbs) which possess antigen-binding activity. See, e.g., (Ward, Gussow et al. 1989; Glockshuber, Malia et al. 1990; Winter and Milstein 1991).

As used herein, the term "chimeric antibody" refers to a monoclonal antibody comprising a variable region, i.e. binding region, from one source or species and at least a portion of a constant region derived from a different source or species, usually prepared by recombinant DNA techniques. Such murine/human chimeric antibodies are the product of expressed immunoglobulin genes comprising DNA segments encoding murine immunoglobulin variable regions and DNA segments encoding human immunoglobulin constant regions. Other forms of chimeric antibodies encompassed by the invention are those in which the class or subclass has been modified or changed from that of the original antibody. Such "chimeric" antibodies are also referred to as "class-switched antibodies". Methods for producing chimeric antibodies involve conventional recombinant DNA and gene transfection techniques now well known in the art. See, e.g., (Morrison, Johnson et al. 1984).

In addition, the invention encompasses within its scope use of immunoglobulins (as defined above) or immunoglobulin fragments to which are fused active proteins, for example, an enzyme of the type disclosed in (Neuberger, Williams et al. 1984), PCT application, WO86/01533. The disclosure of such products is incorporated herein by reference.

Furthermore, as noted above, the immunoglobulin (antibody), or fragment thereof, used in the present invention may be polyclonal or monoclonal in nature. Monoclonal antibodies are the preferred immunoglobulins, however. The preparation of such polyclonal or monoclonal antibodies now is well known to those skilled in the art who, of course, are fully capable of producing useful immunoglobulins which can be used in the invention. See, e.g., (Kohler and Milstein 1975). In addition, monoclonal antibodies which are produced by such hybridomas and which are useful, with the appropriate antigen retrieval procedures, in the practice of the present invention are publicly available from sources such as Advantex BioReagents LLP, 11950 White Oak Landing, Conroe, Tex. 77385, or Zymed, Inc, 458 Cartlon Court, South San Francisco, Calif. 94080.

Particularly preferred antibodies for use in the present invention are monoclonal antibodies which recognize tyrosine phosphorylated, activated Stat5.

Diagnostic Techniques

Diagnostic techniques involve the detection and quantitation of antigens of patients thought to be suffering from carcinoma. Such antigens can be detected using techniques known in the art such as immunohistochemistry and immunocytochemistry wherein an antibody reactive with the antigen is used to detect the presence of the antigen in a tissue sample. These assays, using anti-active Stat5 antibodies can therefore be used for the detection in tissue of the antigen with which the anti-active Stat5 antibodies react and thus predict the metastatic potential of the tumor. Thus, it is apparent from the foregoing that the Stat5 antibodies can be used in most assays involving antigen-antibody reactions. These assays include, but are not limited to, standard radioimmunoassays (RIA) techniques, both liquid and solid phase, as well as enzyme-linked immunosorbent assays (ELISA) assays, ELISPOT, immunofluorescence techniques, and other immunocytochemical assays (see, e.g., (Sikora and Smedley 1984)). Preferably, the assay is one which can be used in situ such as in a biopsy sample to be diagnosed or pathological archived material to directly detect levels of activated Stat5 within the tumor cell nuclei.

The invention also encompasses diagnostic kits for carrying out the assays described above. In one embodiment, the diagnostic kit comprises at least anti-active Stat5 monoclonal antibody, fragments thereof, fusion proteins or chimeric antibody of Stat5, or a non-antibody based binding probe specific for activated Stat5, and a conjugate comprising a specific binding partner for the Stat5 antibody or binding probe and a label capable of producing a detectable signal. The reagents can also include ancillary agents such as buffering agents, antigen retrieval solutions and reagents, and protein stabilizing agents (e.g., polysaccharides). The diagnostic kit can further comprise, where necessary, other components of the signal-producing system including agents for reducing background interference, control reagents or an apparatus or container for conducting the test.

In another embodiment, the diagnostic kit comprises at least a conjugate of the Stat5 antibodies and a label capable of producing a detectable signal. Ancillary agents as mentioned above can also be present.

Flow Cytometry (FACS Analysis)

Flow cytometry (FCM), an automated, laser optics-based technique, is used to detect and quantify the levels of antigens or chemically reactive substances in isolated cells or cell nuclei in suspension. The uptake or binding of fluorescent molecules that diagnose changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins or other antigens as measured by reactivity with specific antibodies; and alterations in plasma membrane composition as measured by the binding of fluorescein-conjugated Annexin V protein to the cell surface. Methods in flow cytometry are discussed in (Ormerod 2000).

Flow cytometric quantitation in breast cancer cells obtained from biopsies or fine needle aspirates provides relevant information, and allows the characterization and quantitation of breast cancer associated parameters, like over or under-expression or activation as compared to normal counterparts, that is suitable for the diagnosis of malignancy or for residual disease evaluation. It may improve scoring systems for prognostic markers of breast tumors. It allows to find original prognostic parameters and improves the comparison of different series due to a better definition of positivity (more quantitative).

Flow cytometry is now widely used for immunophenotyping purposes. It allows, in addition to the determination of the percentage of positive cells, to determine the intensity of fluorescent staining, that can be converted into antigen density provided that reagents are used under saturating concentrations and correct standards of fluorescence are tested in parallel. The concept of antigen density evaluation appears to improve the efficiency of immune techniques in the monitoring of hemopoietic malignancies (Lavabre-Bertrand, George et al. 1994).

Therapeutic Regimes for Treating Breast Cancer

Nearly all patients with breast cancer will have some type of surgery. "Lumpectomy" removes only the breast lump and the surrounding area, or margin, of normal tissue. In most cases, lumpectomy is combined with 6 to 7 weeks of radiation therapy following surgery. This combination of lumpectomy and radiation is often referred to as "breast conserving" therapy. Alternatively, in a "modified radical mastectomy", surgeons remove the entire breast and some of the axillary (underarm) lymph nodes. Modified radical mastectomy is the most common surgery for patients with breast cancer in whom doctors remove the whole breast. Systemic therapies for breast cancer includes adjuvant antiestrogen treatment and chemotherapy.

Breast conserving surgery—"Lumpectomy" removes only the breast lump and the surrounding area, or margin, of normal tissue. If cancer cells are present at the margin (the edge of the excisional biopsy or lumpectomy specimen), a re-excision can usually be done to remove the remaining cancer. In most cases, lumpectomy is combined with 6 to 7 weeks of supplementary radiation therapy following surgery.

Mastectomy—In a "simple (total) mastectomy" procedure surgeons remove the entire breast but do not remove any lymph nodes from under the arm, or muscle tissue from beneath the breast. In a "modified radical mastectomy", surgeons remove the entire breast and some of the axillary (underarm) lymph nodes. Modified radical mastectomy is the most common surgery for patients with breast cancer in whom doctors remove the whole breast. "Radical mastectomy" removes not only the entire breast, but axillary lymph nodes, and the chest wall muscles under the breast as well. The modified radical mastectomy has proved as effective as radical mastectomy, which is nowadays rarely performed due to disfiguration and frequent side-effects.

Lymph node surgery—Regardless of whether a breast cancer patient has a mastectomy, or a lumpectomy for invasive cancer, the physicians need to determine whether the cancer has spread. The regional lymph nodes in the underarm drain lymph from the breast, and are typically the first sites of spread. Furthermore, lymph node involvement increases the likelihood that cancer cells have spread through the blood-stream to other parts of the body.

While lymph node surgery itself does not improve the chance for a cure, this is the only way to accurately determine if the cancer has spread to the lymph nodes. This usually means removing some or all of the lymph nodes in the armpit. Typically 10 to 20 lymph nodes in the armpit are examined by an operation called "axillary lymph node dissection". Although axillary lymph node dissection is a safe procedure with low rates of serious side effects, efforts are ongoing to develop new ways of detecting the spread of cancer to lymph nodes that are less invasive and do not involve a full lymph node dissection. Such alternative methods include the "sentinel lymph node biopsy" (Orr, Hoehn et al. 1999; Sugg, Ferguson et al. 2000), and new detection methods for breast cancer cells in bone marrow and blood (Berois, Varangot et al. 2000; Braun, Pantel et al. 2000; Fetsch, Cowan et al. 2000; Ikeda, Miyoshi et al. 2000; Kraeft, Sutherland et al. 2000; Zhong, Kaul et al. 2000). It is possible that these newer methods in the future may replace lymph node dissection as a means of determining micrometastatic spread of cancer.

Sentinel lymph node biopsy—In the sentinel lymph node biopsy procedure the surgeon finds and removes the 'sentinel node'—the first lymph node into which a tumor drains, and therefore the one most likely to contain cancer cells. In a sentinel lymph node biopsy the surgeon injects a radioactive substance and/or a blue dye into the area around the tumor. Lymphatic vessels carry these materials into the sentinel node. The doctor can either see the blue dye or detect the radioactivity with a geiger counter, and then cuts out the node for examination. If the sentinel node contains cancer, the surgeon will have to perform an axillary dissection-removal of more lymph nodes in the axilla (armpit). If the sentinel node is cancer-free, the patient and her physicians may consider avoiding more lymph node surgery and the potential side effects. Although the sentinel node procedure is relatively new and its long-terin effectiveness is uncertain (Orr, Hoehn et al. 1999; Sugg, Ferguson et al. 2000), it is possible that it will turn out to be equally as effective in determining lymph node spread as the full lymph node dissection.

Detection of disseminated cancer cells in blood and bone marrow—Recent methods for detecting metastatic breast cancer cells in blood (Berois, Varangot et al. 2000; Fetsch, Cowan et al. 2000; Kraeft, Sutherland et al. 2000) or in bone marrow (Braun, Pantel et al. 2000; Ikeda, Miyoshi et al. 2000; Zhong, Kaul et al. 2000) are typically based on the presence of breast cell-specific cytokeratin markers by immunodetection or by genetic testing. These new methods may also lead to an alternative approach to lymph node dissection for determining whether a breast cancer has spread beyond the local tumor area.

Radiation therapy—Radiation is used to destroy cancer cells left behind in the breast, chest wall, or lymph nodes after surgery. Radiation treatments usually take place 5 days a week over a period of 6 to 8 weeks. Side effects most likely to occur include swelling and heaviness in the breast, sunburn-like skin changes in the treated area, and fatigue. Changes to the breast tissue and skin usually go away in 6 to 12 months. In some women, the breast becomes smaller and firmer after radiation therapy. Radiation therapy of axillary (armpit area) lymph nodes can also cause lymphedema. Although generally safe, it is evident that radiation therapy comes at a considerable expense and with potentially serious side-effects. Radiation therapy also involves a major risk for abnormal fetal development, and cannot be used to treat pregnant women with breast cancer.

Chemotherapy—Systemic treatment with anti-cancer drugs given intravenously (injected into a vein) or by mouth. Either way, the drugs travel in the bloodstream and move throughout the entire body. Doctors who prescribe these drugs (medical oncologists) generally use a combination of medicines proven more effective than a single drug. For women with node-negative breast cancer the most frequently used chemotherapy options are CMF (cyclophosphamide, methotrexate, and fluorouracil), CAF (cyclophosphamide, doxorubicin), and AC (doxorubicin (Adriamycin) and cyclophosphamide).

Hormone therapy—Estrogen, a female sex hormone produced by the ovaries, promotes growth of some breast cancers. Doctors use several approaches to block the effect of estrogen or to lower estrogen levels. The most commonly used antiestrogen drug is tamoxifen, taken daily in pill form, usually for 5 years. Studies show that tamoxifen can reduce the chances of breast cancer coming back after surgery if the breast cancer cells contain receptors for estrogen or progesterone. Tamoxifen may be used to treat metastatic breast cancer, but also a significant number of patients with node-negative cancer receive tamoxifen treatment.

Anti-estrogen treatment with tamoxifen is, however, associated with potentially serious morbidity and side-effects For instance, studies have shown an increase of early-stage endometrial cancer (which occurs in the lining of the uterus) among post-menopausal women taking tamoxifen (Cardosi and Fiorica 2000). Another potential side-effect of tamoxifen is deep vein thrombosis, a condition in which blood clots form in the deep blood vessels of the legs and groin. The blood clots sometimes break off and spread to the lungs as a life-threatening complication. The risk of stroke is also somewhat increased. Other side effects are hot flashes, mood swings, and cataracts (Rennie 1993; Gail, Costantino et al. 1999).

EXAMPLE 1

Analysis of Levels of Activated Stat5 in Breast Cancer to Predict Prognosis

It has been established in the present invention that activation of Stat5, a transcription factor which is constitutively activated in normal breast epithelial cells, is gradually lost in lesser differentiated human breast tumor cells. Based on analysis of human normal and malignant breast tissue samples, a positive correlation was observed between Stat5 activation and degree of cell differentiation. Cell differentiation, as measured by low histological grade, of a tumor is a known general prognostic factor for cancer. Tumors of higher grade, i.e. lower degree of tumor cell differentiation, is associated with poor prognosis. The prognostic value of Stat5 activation for breast cancer outcome therefore was examined. A simple procedure for antigen retrieval of tyrosine-phosphorylated Stat5 in formalin-fixed cells and tissues was established. The procedure validated the specificity of detection of antibodies directed to this phosphorylated epitope. The new technique was then applied to a material from 553 primary tumors obtained from breast cancer patients with known disease history and well-characterized tumors.

The results showed that Stat5 was activated in approximately 50% of primary breast cancers, and that activated Stat5 was correlated with reduced rate of recurrence and increased overall survival rate. This correlation was especially strong in patients with node-negative disease. Activated Stat5 may therefore be the first tumor marker that will significantly help to identify a subgroup of low-risk breast cancer patients with excellent prognosis.

Materials and Methods

Cell culture and Transfections used for Validation of Anti-pTyr-Stat5 Antibody AXI T47D human breast cancer cells—T47D cells (American Type Culture Collection, 10801 University Boulevard, Manassas, Va. 20110-2209, USA) were grown in RPMI 1640 medium (Biofluids, Rockville, Md.) containing 10% fetal calf serum (Atlanta Biologicals, Norcross, Ga.), 2 mM L-glutamine, and penicillin-streptomycin (50 IU/ml and 50 µg/ml, respectively) at 37° C. with 5% $CO_2$. Subconfluent cultures of T47D cells were stimulated with 10 nM human prolactin (Genzyme Diagnostics Inc, cat. no. 80-3910-01) for 30 min at 37 C then fixed in situ with 0.5% paraformaldehyde.

COS-7 cells for transfection studies—COS-7 cells (American Type Culture Collection, Fairfax, Va.) were grown in RPMI 1640 medium (Biofluids, Rockville, Md.) containing 10% fetal calf serum (Atlanta Biologicals, Norcross, Ga.), 2 mM L-glutamine, and penicillin-streptomycin (50 IU/ml and 50 µg/ml, respectively) at 37° C. with 5% $CO_2$. When COS-7 cells grown in 100 mM dishes reached 60% confluence cotransfections were performed using the FuGENE 6 transfection reagent (Roche Molecular Biochemicals, Indianapolis, Ind.). Two micrograms of an expression plasrmid p3PRLR encoding the human prolactin receptor (Yamashita, Xu et al. 1998) were co-transfected with either 5 µg of expression plasmid pXM-Stat5a (Liu, Robinson et al. 1995) encoding wild-type Stat5a or with 5 µg of plasmid pXM-Stat5a-Y694F (Yamashita, Xu et al. 1998) encoding a phosphotyrosyl-defective mutant of Stat5a. 24 h after transfection cells were stimulated with 10 nM human prolactin (Genzyme Diagnostics, Inc) for 30 min at 37 C.

Solubilization of Proteins and Immunoblotting—Cells were solubilized in lysis buffer containing 10 mM Tris-HCl, pH 7.6, 5 mM EDTA, 50 mM NaCl, 30 mM sodium pyrophosphate, 50 mM sodium fluoride, 1 mM sodium orthovanadate, 1% Triton X-100, 1 mM phenylmethylsulphonylfluoride, 5 µg/ml aprotinin, 1 µg/ml pepstatin A, and 2 µg/ml leupeptin. Clarified cell lysates were resolved by SDS-PAGE and transferred to polyvinylidene difluoride membranes (Millipore). A monoclonal antibody AX1 specific to Stat5 which is phosphorylated on tyrosine-Y694/699 (Advantex BioReagents LLP, Conroe, Tex.) (1 µg/ml) or polyclonal rabbit antiserum to Stat5a (Advantex BioReagents, Conroe Tex.) (1:3,000) was used as primary antibodies and horseradish peroxidase-conjugated goat antibodies to mouse or rabbit IgG as secondary antibodies in conjunction with enhanced chemiluminesence substrate mixture (Amersham Pharmacia Biotech, NJ). Consistent with specificity of recognition of the key phosphorylation site of Stat5, antibody AX1 recognized prolactin-induced tyrosine phosphorylation of WT-Stat5a but not of mutant Stat5a-Y694F, which lacks the phosphoacceptor hydroxyl group.

Immunocytochemistry and Immunohistochemistry of Activated Stat5

Immunocytochemistry with AX1 in prolactin-stimulated T47D or prolactin-stimulated COS-7 cells expressing WT or phosphotyrosyl-defective Stat5. T47D cells or COS-7 cells transfected and treated as described above were fixed in 0.5% formaldehyde and allowed to dry on glass slides. Sections of paraffin-embedded, formalin-fixed tissues from normal or malignant human breast were deparaffinized by 2 washes in xylene for 15 min each, followed by rehydration in graded ethanol. Slides containing deparaffinized tissue sections or fixed cells were microwave-treated for 25 min in a pressure-cooker with antigen-retrieval solution (1 mM Tris at pH 10). Other antigen-retrieval solutions also may be used, including phosphate buffered saline, pH 7.4, or other buffered aqueous solutions of pH 7-10.

Alternatively, antigen retrieval may be accomplished similar to Jones et al (Jones, Welte et al. 1999) as follows. Sections of fixed tissue can be pretreated first with 1 mg/ml of trypsin for 60 min, and subsequently with 2 N HCl for 60 min at room temperature, followed by two 5 min washes in 100 mM borate buffer. Next samples are treated with 0.2% of NP-40 for 30 min at room temperature (RT). In addition, between each of these treatments, two 5 min washes in phosphate-buffered saline (PBS) are needed.

Following the antigen retrieval procedure, endogenous peroxidase activity was blocked by incubating slides in 0.3% hydrogen peroxide for 10 min at RT, and non-specific binding of IgG was minimized by preincubation in normal goat serum for 2 h at RT. The primary antibody AX1 recognizing phosphorylated tyrosine 694/699 of activated Stat5a/b (Advantex BioReagents LLP, Conroe, Tex., Cat no AX1) was diluted in 1% bovine serum albumin (BSA) in PBS and incubated with the samples at a final concentration of 0.6 mg/ml for 16 h. Antigen-antibody complexes were detected using biotinylated goat anti-mouse secondary antibody (Biogenex) followed by streptavidin-horseradish-peroxidase complex, using 3,3-(prime) diaminobenzidine (DAB) as chromogen (brown) and Mayer hematoxylin (blue) as counterstain. For controls subtype-specific mouse IgG was used.

Monoclonal Anti-phospho-Stat5a/b(Tyr694/699) Antibody AX1

AX1 is a mouse monoclonal antibody generated against an immunogen consisting of a phosphopeptide corresponding to the phosphorylated tyrosine-694 of human Stat5a, KAVDG(phosoho Y)VKPQIK (SEQ ID NO: 1) that was conjugated to keyhole limpet hemocyanin by standard technique (Harlow and Lane 1988). This antigen was used for standard immunization of BALB/c mice (Shepherd and Dean 2000).

Fusion and screening: Lymphocytes from the spleen of mice with the highest titer were fused with a mouse myeloma cell line. The fused cells were plated in eight 96 well plates. Wells with cell growth were screened for IgG production and for specific antibody production by standard ELISA method and 8 mother clones were selected. Positive wells were subcloned three times by limited dilution method. Monoclonal antibody production was achieved in serum-free hybridoma cultures and purification was done by standard Protein A Sepharose affinity chromatography (Harlow and Lane 1988; Shepherd and Dean 2000). Clone AX1 specifically recognizes tyrosine phosphorylated isoforms of Stat5, but not unphosphorylated isoforms. This specificity has been established by immunoblotting of unphosphorylated and phosphorylated Stat5 immunoprecipitated from human breast cancer cells, or other prolactin-responsive cells, that have either been treated with prolactin for 30 min to stimulate Stat5 tyrosine phosphorylation, or from untreated cells in which Stat5 remains unphosphorylated (See below, Results section, FIG. 2). Furthermore, AX1 does not recognize Stat5 mutants in which the Tyr694 residue has been substituted with phenylalanine, which cannot undergo phosphorylation due to lack of the hydroxyl group of the phenyl ring, but otherwise resembles tyrosine (see below, Results section, FIGS. 3 and 4).

Other Anti-phospho-Tyr Stat5 Antibodies

Other antibodies to tyrosine phosphorylated Stat5 may also be useful for detection of activated Stat5 in tissues or cells including a monoclonal anti-Stat5pY antibody from Zymed, Inc (458 Carlton Court, South San Francisco, Calif. 94080; Cat. no. 33-6000), a monoclonal antibody anti-phospho Stat5a/b (Y694/Y699) from Upstate Biotechnology Inc (199 Saranac Ave, Lake Placid, N.Y. 12946; Cat. no. 05-495), and a polyclonal phospho-Tyr-Stat5 antibody from Upstate Biotechnology, Inc (Cat. no. 06-798). Of these, only Zymed's anti-Stat5 is reportedly useful in immunohistochemistry (Jones, Welte et al. 1999), although the extensive antigen retrieval procedure used included extended treatment of tissue sections with proteases. A concern with that antigen retrieval method is loss of antigen unless the proteolytic process is very carefully controlled. Because various batches of proteolytic enzymes will have different activities, it may be particularly difficult to keep conditions consistent with this extended and elaborate antigen retrieval method. No data are currently available about Upstate Biotechnology's anti-phospho-Stat5a/b (pTyr694/699) antibody regarding its usefulness in immunohistochemistry. There has been no suggestion whatsoever, to use any of the above antibodies in the diagnostic or monitoring methods for cancer as claimed in the current application.

Obtaining Human Samples

Human breast cancer cell line T47D was obtained from ATCC (American Type Culture Collection, 10801 University Boulevard, Manassas, Va. 20110-2209, USA). Human female breast tissues, both control tissue and that suspected of harboring a carcinoma, were obtained by standard biopsy and/or surgery methods known to one of skill in the art.

For example, incisional biopsies, which involve the removal of a small wedge of tissue from a larger tumor mass, and excisional biopsies, which involve an excision of the entire suspected tumor tissue with little or no margin of surrounding normal tissue were used. Aspiration (or fine needle) biopsy, which involves the aspiration of cells and tissue fragments through a needle that has been guided into the suspect tissue, are other examples of suitable tissue extraction methods. See generally (DeVita, Hellman et al. 1982; Calabresi and Schein 1993).

Breast Cancer Tissue Microarray

Formalin-fixed and paraffin-embedded tumor specimens were from the archives of the Institute for Pathology, University of Basel, Switzerland, and were obtained in the form of a tissue microarray mounted on a glass slide. All tumors were reviewed by a pathologist. The tissue microarray was constructed as described by (Kononen, Bubendorf et al. 1998). Briefly, a tissue arraying instrument (Beecher Instruments, MD) was used to create holes in a recipient paraffin block and to acquire tissue cores from the donor block by a thin walled needle with an inner diameter of 0.6 mm, held in an X-Y precision guide. The cylindrical sample was retrieved from the selected region in the donor and extruded directly into the recipient block with defined array coordinates. A solid steel wire, closely fit in the tube, was used to transfer the tissue cores into the recipient block. After the construction of the recipient block, multiple 5 um sections were cut with a microtome using an adhesive-coated tape sectioning system (Instrumedics, NJ). HE-stained sections were used for histological verification of tumor tissue on the arrayed samples. The use of tissue microarray is not a critical element of the present invention. Alternatively, tumor samples may be used that are mounted by conventional histological technique as larger tissue sections on individual glass slides.

Tumor Scoring and Statistical Methods

Individual breast tumor samples were scored for activated Stat5 levels on a scale from 0-4, where 0 is negative and 1-4 represented positive staining at four semiquantitative steps of increasing intensity. After an initial cutoff analysis, scores 1-4 were recoded as positive because each positive score was associated with significantly reduced risk for relapse and fatal disease, especially in node-negative breast cancer, when compared to score 0 (negative), but increasing intensity among the positive scores did not provide additional risk reduction (FIG. 1). Cox proportional hazard analysis was used to estimate the prognostic value of activated Stat5.

Cox regression analysis is a semiparametric method for modeling survival or time-to-event data in the presence of censored cases (Hosmer and Lemeshow, 1999; Cox, 1972). In contrast to other survival analyses, e.g. Life Tables or Kaplan-Meyer, Cox allows the inclusion of predictor variables (covariates) in the models. By constructing a Cox regression model, with Stat5 activation status of primary breast tumors as a covariate, it is possible to test hypotheses regarding the correlation of Stat5 activation status of primary breast tumors to time-to-onset of either disease relapse (disease-free survival time, or time to metastatic disease), or time to death from the disease (overall survival time). Cox regression analysis is also known as Cox proportional hazard analysis. This method is standard for testing the prognostic value of a tumor marker on patient survival time. When used in multivariate mode, the effect of several covariates are tested in parallel so that individual covariates that have independent prognostic value can be identified, i.e. the most useful markers.

Results

Validation of technique by immziocytochemistry using anti-phosphoTyr-Stat5 antibody.

Phosphospecific antibodies to tyrosine phosphorylated Stat5a/b (pTyr694/pTyr699) were developed and conditions for immunocytochemistry as well as immunohistochemistry of activated, tyrosine phosphorylated Stat5 in isolated cells or in paraffin-embedded tissue were established.

Figure 2A:
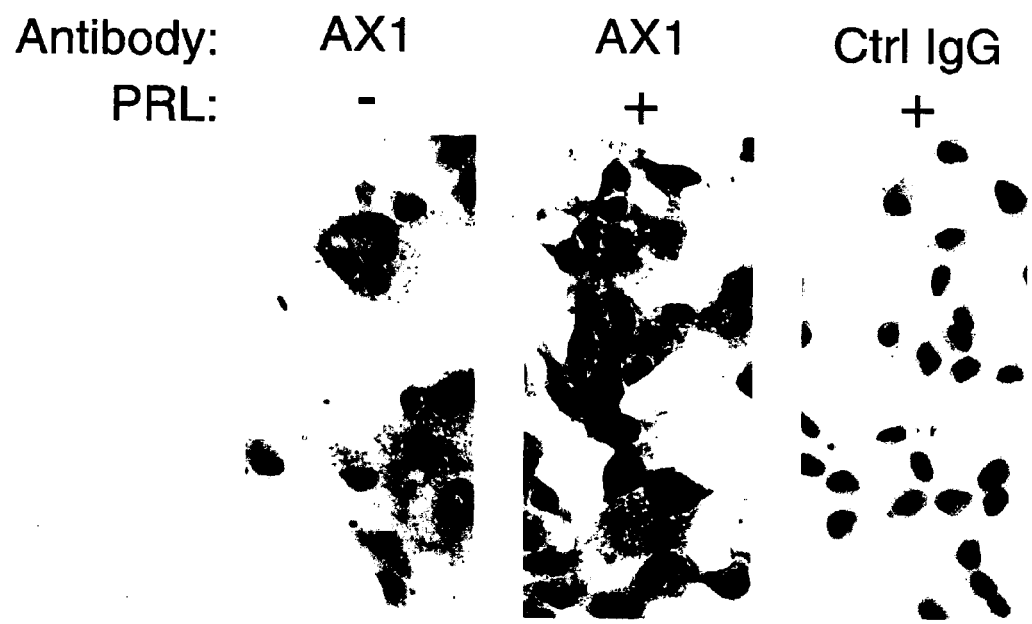
FIGS. 2A-2B—Detection of activated Stat5 by AX1 antibody. Immunocytochemistry (FIG. 2A) and immunoblotting (FIG. 2B) of activated Stat5 in T47D human breast cancer cells before and after prolactin stimulation.
Figure 2B:
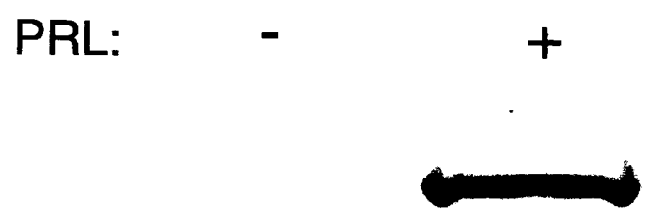
Figure 3:
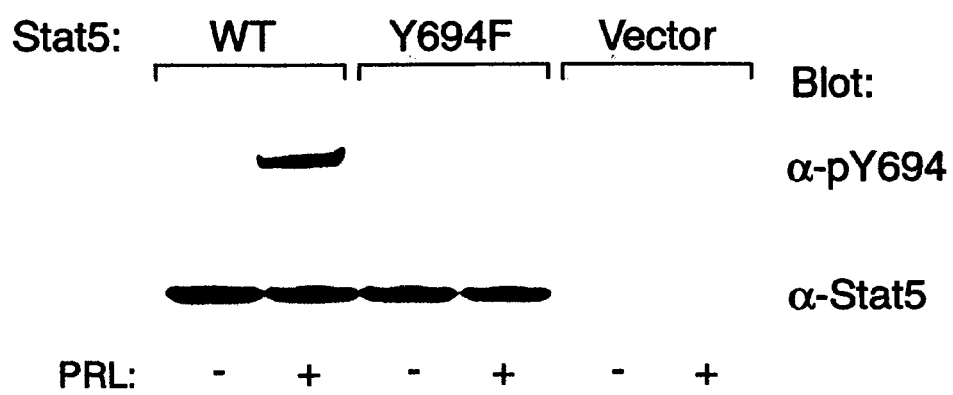
FIG. 3—Antibody AX1 specifically detects tyrosine phosphorylated Stat5 by immunoblotting. Immunoblotting of activated Stat5 in COS-7 kidney cells transfected with either wild type Sta5 or a tyrosine phosphorylation-defective mutant, Stat5-Y694F.
Figure 4:
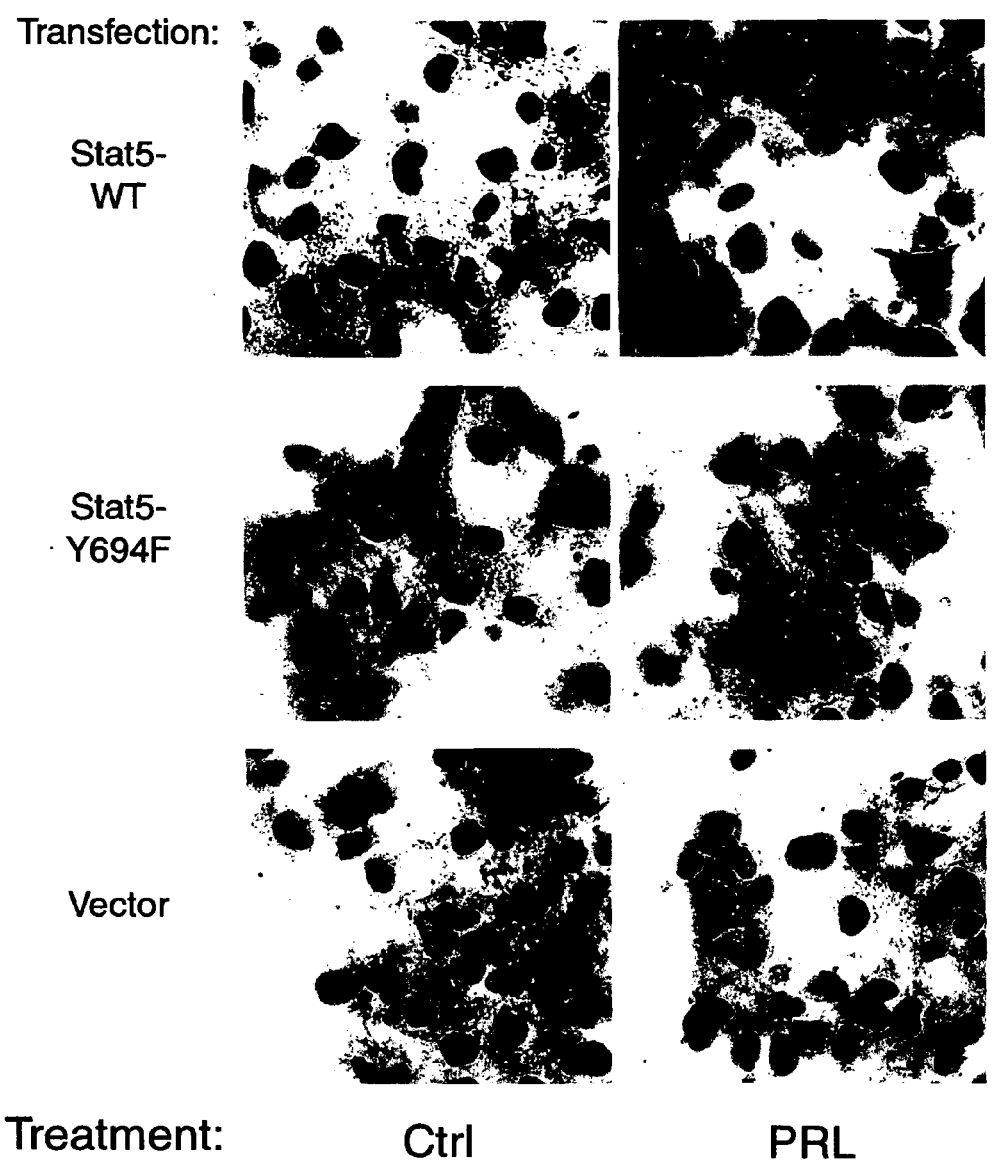
FIG. 4—Antibody AX1 specifically detects tyrosine phosphorylated Stat5 by immunocytochemistry. Immunocytochemical detection of activated Stat5 in COS-7 kidney cells transfected with either wild type Stat5 or a tyrosine phosphorylation-defective mutant, Stat5-Y694F.

Immunocytochemistry of formalin-fixed human T47D breast cancer cells showed marked nuclear staining with AX1 following 30 min of prolactin stimulation, consistent with inducible tyrosine phosphorylation and nuclear translocation of Stat5 (FIG. 2A, left and middle panels). Unstimulated cells displayed only weak and scattered nuclear staining (FIG. 2A, left panel), and prolactin-stimulated cells tested with control IgG were negative (FIG. 2A, right panel). FIG. 2B shows the corresponding prolactin-induced tyrosine phosphorylation of Stat5 in human breast cancer cells T47D by immunoblotting. Specific recognition by AX1 of Stat5 molecules that are phosphorylated on the positionally conserved tyrosine residue involved in Stat5 dimerization was verified by testing of AX1 against the phosphorylation-defective mutant Y694F. In this mutant the phosphoacceptor hydroxyl group of Tyr694 of Stat5a had been removed through substitution with Phe (FIG. 3). For these experiments, COS-7 cells that lacked detectable levels of endogenous Stat5 were transfected with expression plasmids encoding prolactin receptor and either wild type (WT) Stat5, mutant Stat5 (Y694F), or empty control plasmid (Ctrl). Immunoprecipitation of Stat5 from transfected cells followed by immunoblotting with AX1 showed that this antibody recognized tyrosine phosphorylated Stat5 only in prolactin-stimulated cells that expressed WT-Stat5, and not in unstimulated cells or in prolactin-stimulated cells expressing the phosphotyrosyl-defective Stat5 mutant (FIG. 3, upper panel). Blotting of replicate samples with anti-Stat5 antibodies verified that equal levels of Stat5-WT and Stat5-Y694F were expressed in the transfected cells, and that no Stat5 was detectable in untransfected COS-7 cells (FIG. 3, lower panel). The specificity of reaction of AX1 to Stat5 phosphorylated on the positionally conserved tyrosine residue also was verified by immunocytochemistry in COS-7 cells (FIG. 4). As demonstrated by marked and inducible nuclear staining, Stat5 became activated after prolactin stimulation in approximately 30-50% of the COS-7 cells, consistent with expected transfection efficiencies of these cells (FIG. 4, upper panels). No inducible nuclear or cytoplasmic staining was observed in COS-7 cells transfected with either phosphotyrosyl-defective Stat5 mutant or with vector control (FIG. 4B, middle and lower panels). These initial experiments therefore demonstrated that antibody AX1 specifically recognized the tyrosine phosphorylated form of Stat5, and that this antibody was useful for immunocytochemical analysis of formalin-fixed cells.

Figure 5:
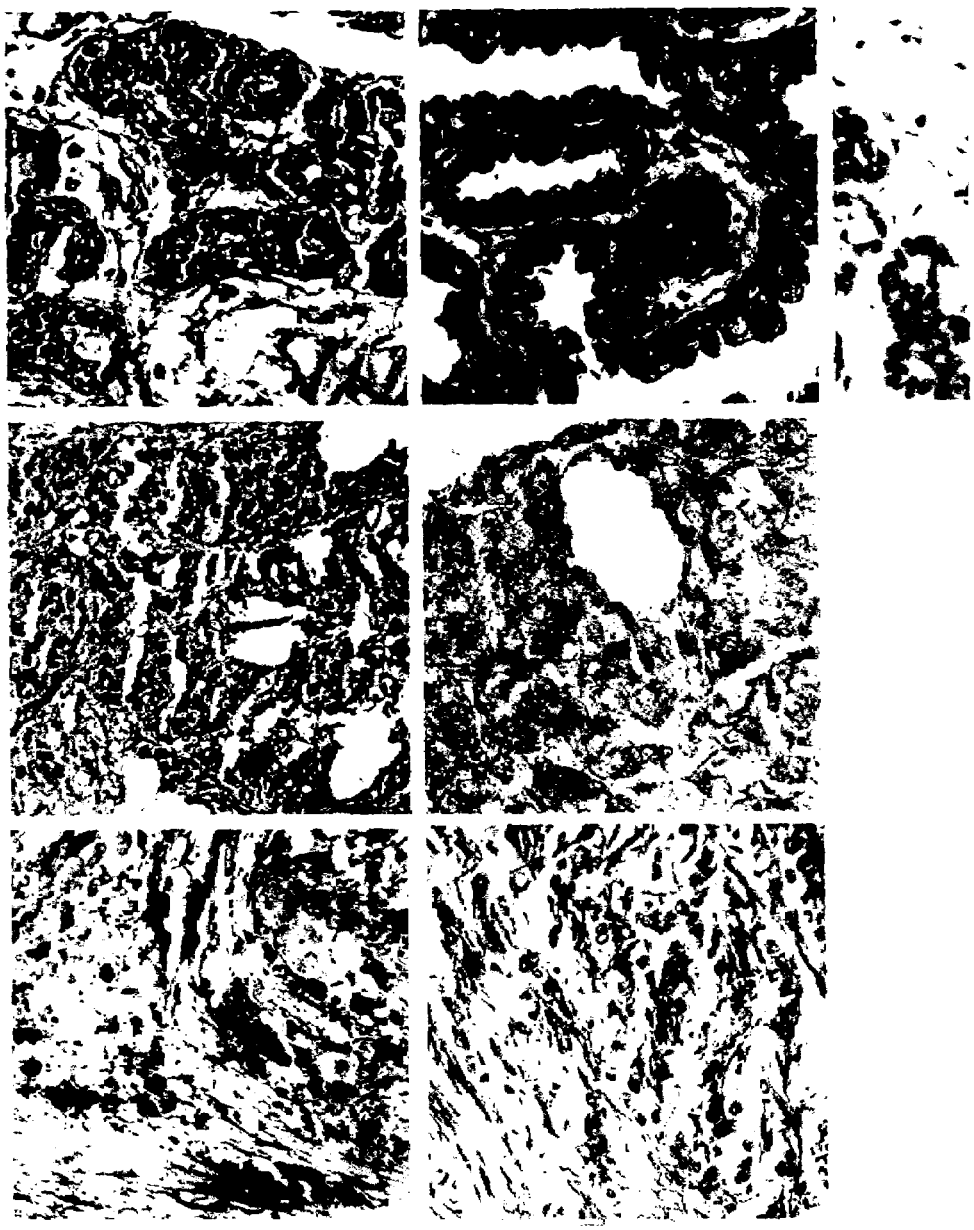
FIG. 5—Immunohistochemical detection of levels of activated Stat5 in normal and malignant human breast tissues using antibody AX1. Immunohistochemical detection of activated Stat5 in formalin-fixed, paraffin-embedded normal and malignant human breast tissues.

To test whether AX1 is useful for sections from formalin-fixed, paraffin-embedded tissues, initial screening of normal and malignant human breast tissues was performed. This analysis established that AX1 was useful for detection of activated Stat5 in sections from paraffin-embedded, formalin-fixed tissue and established that there were marked differences in nuclear AX1 staining between human breast tissue specimens. Specifically, immunohistochemistry of sections of paraffin-embedded tissues from resting and lactating breast demonstrated that Stat5 was consistently activated in resting mammary tissue, and even more markedly in lactating breast tissue (FIG. 5, upper panel). Furthermore, FIG. 5 also shows examples of human primary breast carcinomas that were either positive or negative for Stat5 activation, including cases of both infiltrating ductal and lobular breast carcinoma specimens (FIG. 5, middle and lower panels, respectively). Collectively, these experiments proved that antibody AX1 can be used to specifically recognize activated, pTyr-Stat5 within the cell nucleus, and is useful for immunocytochemical and immunohistochemical analyses in normal tissues and at least breast cancer.

The levels of activated Stat5 were evaluated in a series of human primary breast cancer samples using a phosphorylation-state specific antibody that recognizes tyrosine phosphorylated Stat5 and works in formalin-fixed tissue. Taking advantage of tissue microarray technology, the new immunohistochemical procedure was applied simultaneously to tissue derived from a total of 611 primary breast tumors from patients with well-characterized tumors. Long-term follow-up and disease history was available for 553 of these tumors.

With the goal of testing whether levels of active Stat5 in primary breast tumors are a marker of good prognosis, tumor tissues were analyzed from 553 separate breast malignancies of variable disease stage. For these cases, considerable information was available on the majority of tumors, including ER status, PR status, age of patients at diagnosis, disease stage, and status of axillary lymph nodes (Kononen, Bubendorf et al. 1998). With regard to assessing the role of Stat5 as a prognostic marker in node-negative breast cancer it was of particular interest to the current study that a relatively large number of node-negative tumors were from patients who had not received adjuvant antihormone or chemotherapy.

After eliminating specimens that were of insufficient quality for conclusive analysis, levels of activated Stat5 were determined in 428 of the 553 primary human breast tumor samples. The principal reason for exclusion of as many as 125 cases was not related to a generally poor specimen quality but rather reflected the technological compromise of small sample sizes available on tissue arrays, where each tumor is represented by a circular tissue section of 0.6 mm diameter (Kononen, Bubendorf et al. 1998; Schraml, Kononen et al. 1999). Samples were primarily excluded because of lack of sufficient number of tumor cells in the available section, and was only to a lesser extent due to unsatisfactory or unrepresentative tissue quality.

Levels of Activated Stat5 are a Marker of Human Breast Cancer Cell Differentiation Levels of activated Stat5 were determined by a semiquantitative scoring method that was based on the combined intensity of nuclear AX1 staining and the proportion of tumor cells that showed staining. Samples without nuclear staining were scored as 0 and samples showing nuclear staining were scored within a range of 1-4 according to the proportion and intensity of nuclear staining of tumor cells. This approach corresponded to a simplified version of the general immunohistochemical scoring method described by Allred and colleagues (Allred, Harvey et al. 1998). Correlation analysis of this large material established a strong negative correlation between levels of activated Stat5 and reduced tumor cell differentiation (high grade) as measured by histological grade (Table 1; Spearman correlation coefficient (rho)=−0.346; p<0.001). A weaker but statistically significant negative correlation also existed between levels of activated Stat5 and tumor stage (rho=−0.144; p=0.003). Importantly, there were highly significant positive correlations between levels of activated Stat5 in the primary tumor and both time to relapse of disease (metastasis; rho=0.223; p<0.001) and overall survival time (rho=0.218; p<0.001; see Table 1). These observations provided the first evidence that Stat5 activation status of primary tumors might has prognostic significance for breast cancer patients. In contrast, levels of activated Stat5 in the primary tumor did not correlate with either patient age or number of positive lymph nodes (Table 1).

TABLE 1

Spearman Rank Correlation Analysis of Levels of Activated Stat5,
Tumor Grade and Other Selected Parameters

|  |  | Activated Stat5 | Tumor grade | Tumor stage | Disease free interval | Survival time | Age |
|---|---|---|---|---|---|---|---|
| Tumor grade | Correlation Coeff. | −.346** | | | | | |
|  | Sig. (2-tailed) | .000 | | | | | |
|  | N | 428 | | | | | |
| Tumor stage | Correlation Coeff. | −.144** | .187** | | | | |
|  | Sig. (2-tailed) | .003 | .000 | | | | |
|  | N | 422 | 547 | | | | |
| Disease free interval[a] | Correlation Coeff. | .223** | −.285** | −.232** | | | |
|  | Sig. (2-tailed) | .000 | .000 | .000 | | | |
|  | N | 428 | 553 | 547 | | | |
| Survival time[a] | Correlation Coeff. | .218** | −.286** | −.192** | .934** | | |
|  | Sig. (2-tailed) | .000 | .000 | .000 | .000 | | |
|  | N | 428 | 553 | 547 | 553 | | |
| Age | Correlation Coeff. | −.015 | −.104* | .053 | .063 | .023 | |
|  | Sig. (2-tailed) | .753 | .015 | .216 | .138 | .582 | |
|  | N | 428 | 553 | 547 | 553 | 553 | |
| Positive lymph nodes | Correlation Coeff. | .014 | .120** | .340** | −.333** | −.268** | −.105* |
|  | Sig. (2-tailed) | .780 | .006 | .000 | .000 | .000 | .017 |
|  | N | 397 | 519 | 513 | 519 | 519 | 519 |

**Correlation is significant at the .01 level (2-tailed).
*Correlation is significant at the .05 level (2-tailed).
[a]Includes both censored and uncensored data Positive Stat5 Activation Status Correlates with Improved Prognosis of Breast Cancer.

Figure 6A:
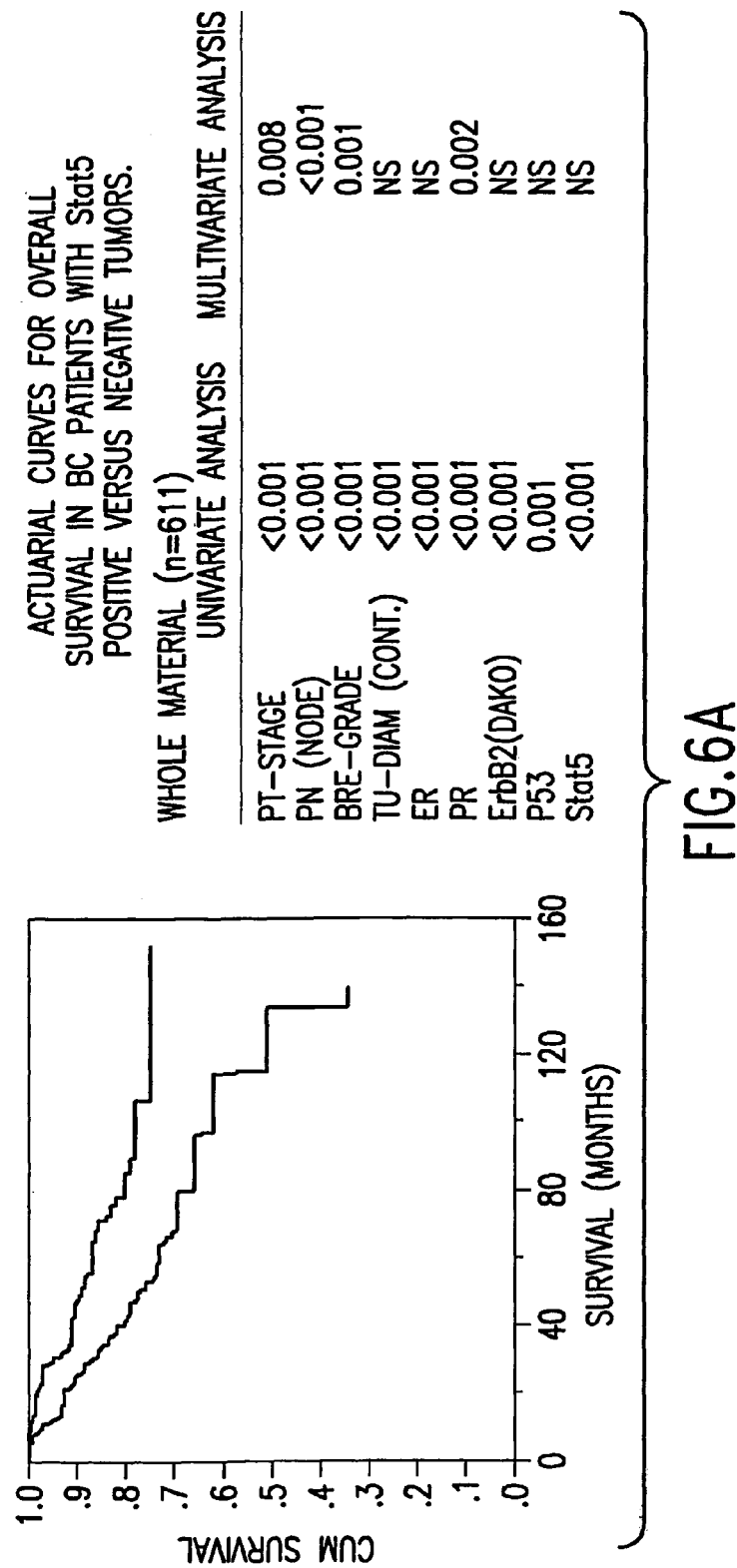
FIG. 6—Actuarial curves. Kaplan-Meyer actuarial curves for overall survival in breast cancer patients with Stat5 positive versus Stat5 negative tumors FIG. 7—Survival Function. Kaplan-Meyer actuarial curves for recurrence of metastatic disease (relapse) in node negative breast cancer patients who had undergone lumpectomy (breast conserving surgery) with Stat5 positive versus Stat5 negative tumors. Note that positive Stat5 activation status is associated with no relapse, indicating that lumpectomy is a safe procedure for this group of patients.

For subsequent statistical analyses, levels of activated Stat5 were recoded as a dichotomous variable that was either negative (score 0) or positive (scores 1-4) as described above. The terms negative and positive Stat5 activation status used in this description refers to levels of activated Stat5 corresponding to scores 0 and scores 1-4, respectively. Initial analysis of the breast cancer material of 553 cases with known disease history revealed that positive Stat5 activation status in primary tumors was associated with a moderately reduced risk of disease progression (FIG. 6A). By Kaplan-Meyer analysis (Kaplan 1958), the estimated risk of death from breast cancer within 10 years of surgical removal of the primary tumor was 25.8% (+/−(SE)4.6%) in patients with Stat5 positive breast cancer versus 48.9% (+/−7.7%) in the Stat5 negative group (p<0.001 by univariate analysis). Proportional hazard analysis showed that Stat5-negative status was associated with a general 2.0-fold increased risk of death from breast cancer (p=0.001). A similar protective effect of positive Stat5 status also was observed for disease-free survival (relapse), with 2.0-fold higher risk for progression to metastatic disease in patients with Stat5 negative tumors (p<0.001 by univariate proportional hazard analysis; actuarial curves not shown). However, when several tumor markers were compared by multivariate Cox regression analysis, Stat5 status of the primary tumor did not have independent predictive value in this combined material of both node-positive and node-negative patients. Instead, node status, tumor stage, histologic grade and progesterone receptor status were markers that had independent predictive value on survivorship in the combined material (FIG. 6A).

Positive Stat5 Activation Status is a Strong Positive Prognostic Marker for Node-negative Breast Cancer.

Figure 6B:
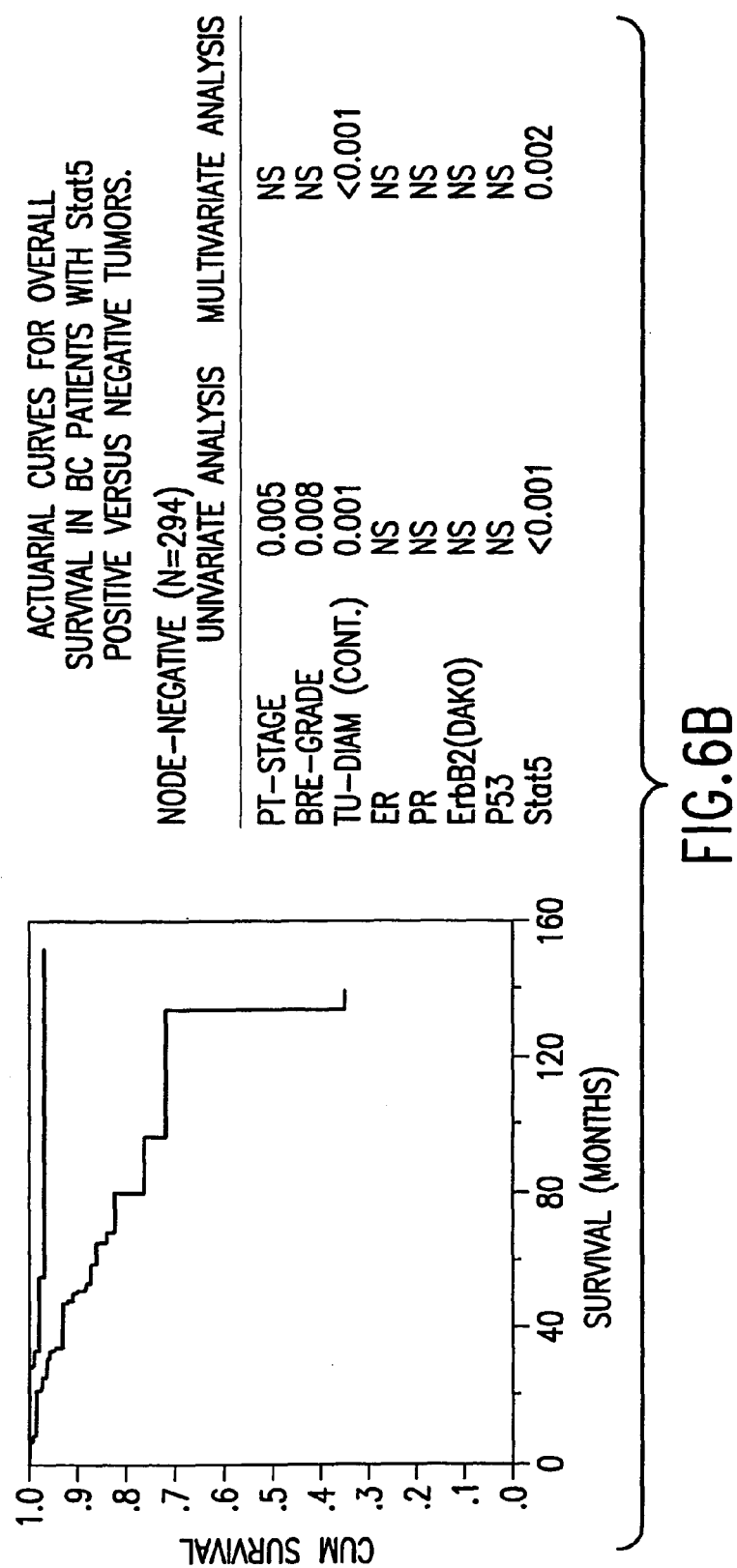

To test the ability of Stat5 activation status to predict overall survival in patients with node-negative disease, the analysis was confined to cases with localized tumors. In this patient group (n=272), Stat5 activation status was conclusively determined in 211 cases. Positive Stat5 activation status was associated with significantly increased overall survival (FIG. 6B) and disease-free survival (not shown), both by univariate and multivariate analysis (FIG. 6B). Multivariate analysis showed that positive Stat5 activation status continued to be a strong prognostic factor, providing additional and independent predictive information on overall survival in patients with node-negative disease, even when other prognostic factors were taken into account (FIG. 6B). In the material of node-negative tumors, other than Stat5 activation status only tumor size had independent prognostic value among the currently used prognostic factors, including tumor histological grade, and hormone receptor status.

Associated with positive Stat5 status in the primary tumor of breast cancer patients with node-negative disease, there was an approximately 25% survival benefit after 10 years. In this population of breast cancer patients, the estimated risk of death from the disease within 10 years of diagnosis based on Kaplan-Meyer analysis was approximately eight (8.5) times higher among patients with negative Stat5 activation status in the primary tumor than that of patients with positive Stat5 activation status (28.3% (+/−7.0%) vs. 3.32% (+/−1.9%); p=0.0001). Proportional hazard analysis estimated the overall relative risk of death in node-negative patients with negative Stat5 activation status of tumors to be 7.7 times the risk associated with Stat5 positive tumors (p=0.001).

Among node-negative patients in this material a significant fraction had received some form of adjuvant hormone or chemotherapy. To eliminate the potential bias introduced in case Stat5 status of primary tumors affects the clinical response to adjuvant therapy, and more specifically assess the pure prognostic value of Stat5 status in patients with node-negative breast cancer, tumors from patients who had received adjuvant therapy were excluded from the analysis. Survival analysis in the remaining population of node-negative patients. (n=114; valid n=86) showed that positive Stat5 activation status continued to be a strong prognostic marker associated with increased overall survival (FIG. 6C) and increased disease-free survival (not shown). Most importantly, positive Stat5 activation status in the primary tumor of node-negative patients who did not receive adjuvant treatment was associated with very high probability of 10 year survival (>97.5%) based on Kaplan-Meyer estimates (FIG. 5C). Proportional hazard analysis of this material of patients with node-negative disease estimated a general 11.0-fold higher risk for death when primary tumors were Stat5 negative compared to that of patients with Stat5 positive tumors (p=0.023).

Figure 6C:
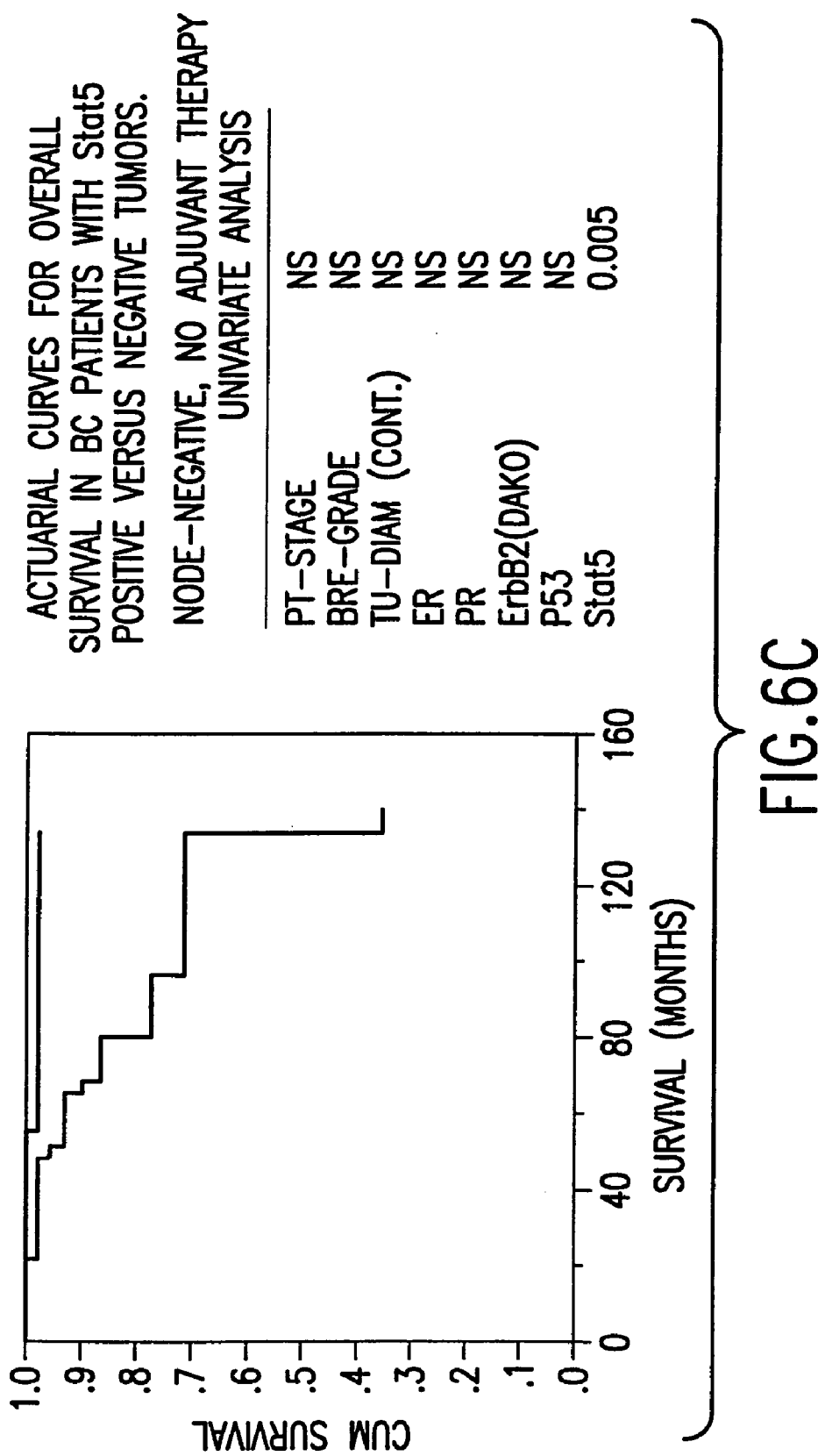
Figure 6D:
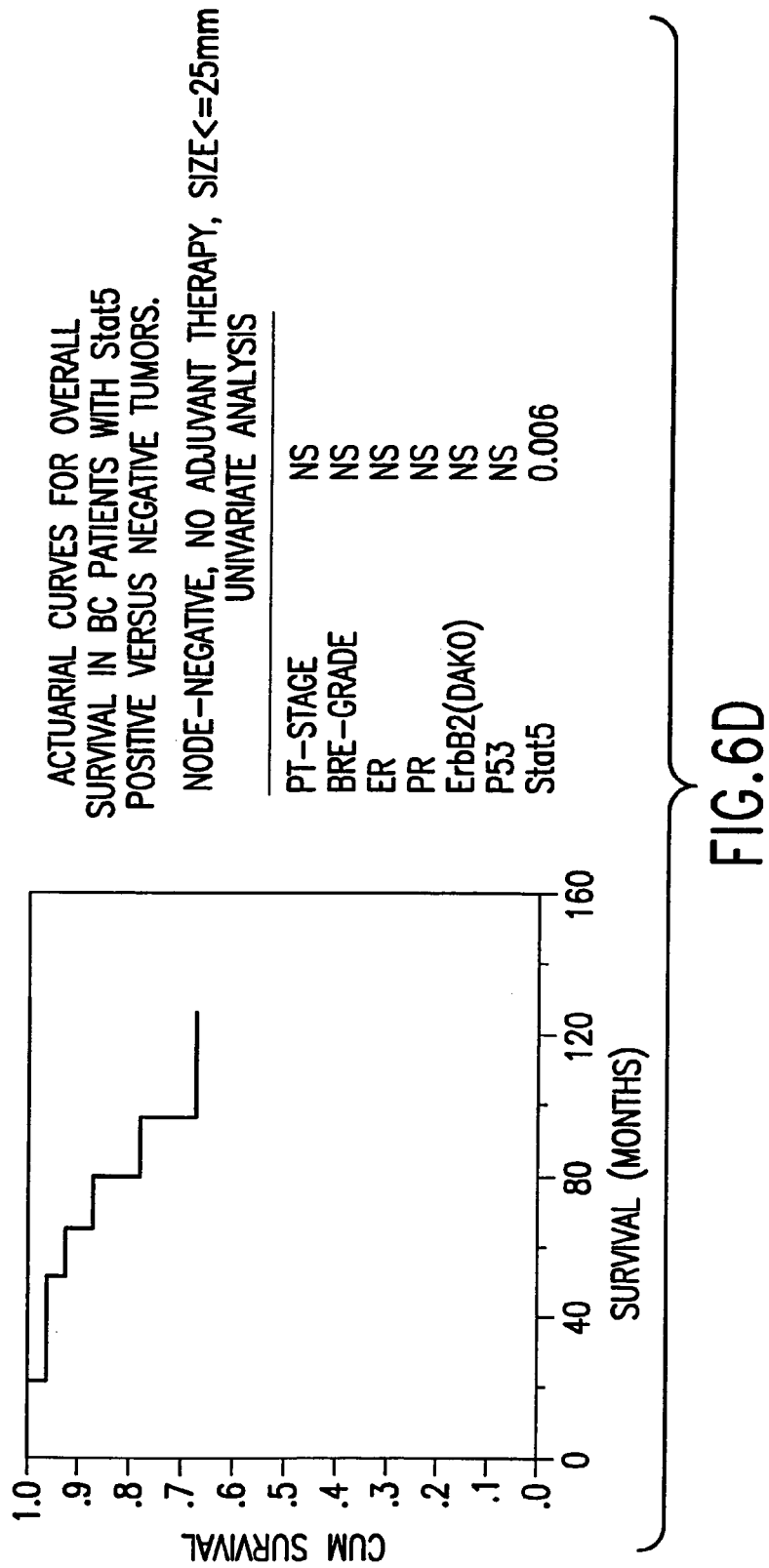

Preferably, histological breast tumor markers are prognostic also in small tumors. The mean diameter of primary tumors within the entire material was 27 mm. To assess whether Stat5 status remained a prognostic factor also in patients with small, node-negative tumors, the material of node-negative, adjuvant therapy-free patients was further confined to tumors with diameter of 25 nm or less. From a group of 58 cases, no deaths due to breast cancer were reported over the observation period among patients with Stat5 positive status, in contrast to five deaths among patients with Stat5 negative tumors (FIG. 6D). Despite the limited number of cases available for this particular analysis, the observed difference between the two populations was highly significant (p=0.006 by univariate chi-square statistics). Collectively, these results clearly suggested that Stat5 activation status will be useful also for predicting the prognosis of breast cancer patients with small, node-negative tumors.

The main conclusions from these analyses are:
1) Levels of activated Stat5 were strongly correlated with well-differentiated tumor histology.
2) Activated Stat5 status in node-negative tumors was associated with a remarkably reduced risk for subsequent disease relapse and death from breast cancer, an observation that was highly significant both by univariate and multivariate Cox regression analysis.

The data suggest that Stat5 activation status of individual tumors will significantly help to identify low-risk breast cancer patients. Stat5 activation status was the most reliable prognostic molecular/biochemical marker among untreated breast cancer patients with node negative disease. Knowledge of levels of Stat5 activation status in breast tumors will distinguish between low and relatively high risk patients with node-negative breast cancer. Identifying patients with excellent prognosis will, in general, allow doctors and patients to select less invasive and less extensive therapeutic approaches (see Example 2 for more details on therapeutic options). Stat5 activation status adds a new level of independent information to current markers of breast cancer.

Activated Stat5 is particularly valuable as a marker of low-risk for relapse and death in patients without detectable metastases to nearby lymph nodes, so called node-negative breast cancer. This is important, because until now, it has been impossible to predict with any confidence the risk for relapse (metastatic disease) in this large group of patients with apparently localized disease.

In addition to its diagnostic value for breast cancer, activated Stat5 levels should be useful in diagnosing and prognosticating other forms of cancer where activated Stat5 levels are an indication of tumor differentiation and metastastic potential. In particular, because of the high degree of tissue regulatory similarities between ovaries and mammary glands, including a critical role of Stat5 in maintaining normal differentiated function of the ovaries (Teglund, McKay et al. 1998), Stat5 should also be a prognostic marker for localized ovarian cancer. Without being limited by the following mechanism of action, if one assumes a general differentiative and anti-invasive role of Stat5 in various tissues, the diagnostic value of activated Stat5 levels should also be applicable to other forms of cancer, including but not limited to cancer of the ovaries, uterus, large bowel, thyroid, prostate, and skin. In this regard, one of skill in the art should be able to apply the basic methods used for monitoring and diagnosing breast cancer to other cancers of interest.

EXAMPLE 2

Treatment of Breast Cancer

A sample of breast tissue from a patient with breast cancer or suspected of having breast cancer is obtained. The sample may be either a biopsy sample, a pathology sample obtained after a tumor has been removed from the breast or an archived sample previously obtained from the patient. The sample is analyzed similar to Example 1.

Based on analysis of levels of activated Stat5 the tumor sample, a treatment regime is determined using acceptable treatment alternatives known to those skilled in the art. These may include, but are not limited to, observation, mode of surgery, non-adjuvant therapies such as radiation, and adjuvant therapies such as tamoxifen or cytotoxic chemotherapy.

The invention has established that a positive Stat5 activation status in node-negative breast cancer is associated with a remarkably low risk for subsequent disease relapse and death from breast cancer within 10 years. Specifically, in patients who did not receive any supplementary antihormone therapy, adjuvant chemotherapy, or neoadjuvant chemotherapy, 10 year estimated survival rate was approximately 97.5% (FIG. 6C). Positive Stat5 activation status in node-negative breast cancer reflects reduced risk of micrometastatic disease. For those skilled in the art, knowledge of levels of activated Stat5 in breast tumor biopsies may therefore directly affect the treatment regime chosen.

It is therefore significant that the present invention demonstrates that Stat5 status represents a new and informative prognostic marker for breast cancer, especially of node-negative breast cancer. Of immediate clinical importance is the exceptionally low risk for disease progression associated with positive Stat5 status in patients with node-negative breast tumors. Knowledge of the Stat5 activation status in primary breast tumors at the time of diagnosis and surgical removal may therefore directly influence therapeutic decisions regarding adjuvant hormone and chemotherapies, as well as supplementary radiation therapy. In general, the reduced risk of micrometastatic breast cancer associated with positive Stat5 activation status may be used to favor less invasive and less extensive treatment options, and thus reduce over-treatment of patients with potentially toxic, mutilating or costly procedures and regimes. As will be discussed in more detail below, this may involve mode of surgery, use of supplementary radiation therapy, or use of adjuvant antiestrogen or chemotherapy. This is important because a large number of breast cancer patients with localized disease currently receive potentially toxic and expensive supplementary therapies (Thomssen and Janicke 2000). Furthermore, Stat5 status determined in biopsies of primary breast tumors may also help guide surgeons and patients to select between tissue conserving surgery and radical mastectomy.

Impact of Stat5 activation status of primary tumors on choice of surgery. A series of studies have shown that in breast cancer patients with node-negative disease (stage I and II), conservation surgery (lumpectomy) is as effective as the modified radical mastectomy procedure (Reid and Donohue 1992; Noguchi and Miyazaki 1994). The principal advantage of breast conserving therapy is that lumpectomy preserves the appearance of the breast. Nontheless, modified radical mastectomy remains a widely used procedure, often due to personal preference of the surgeon and traditions at individual clinics.

Figure 7:
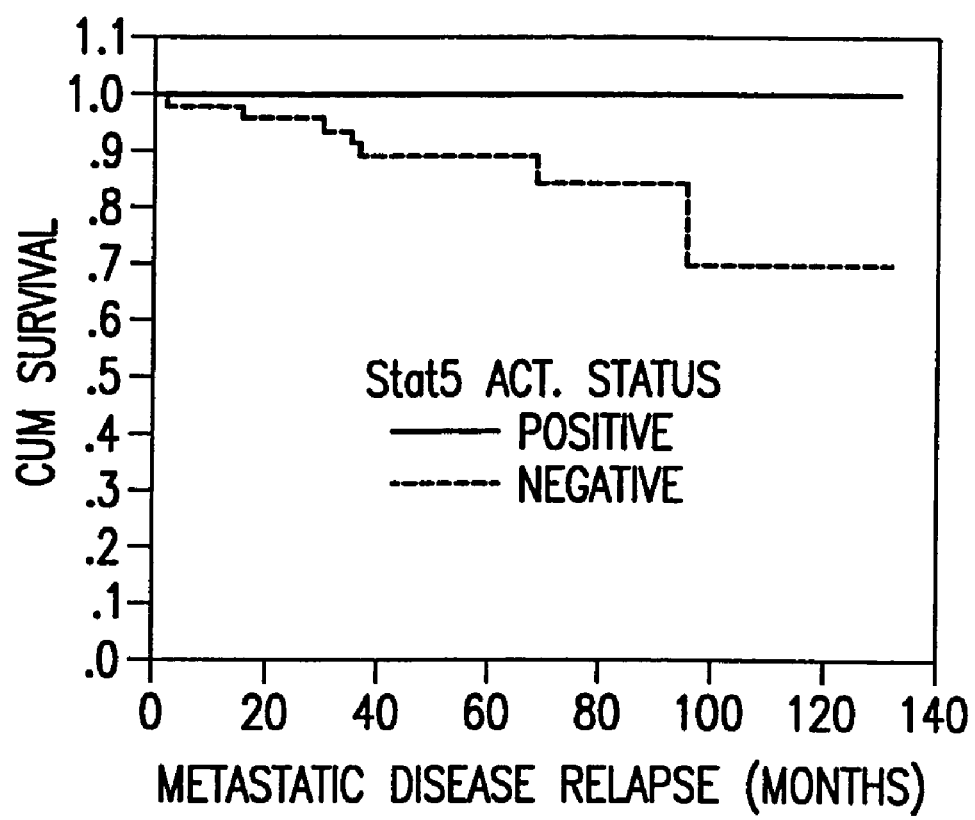
Figure 8:
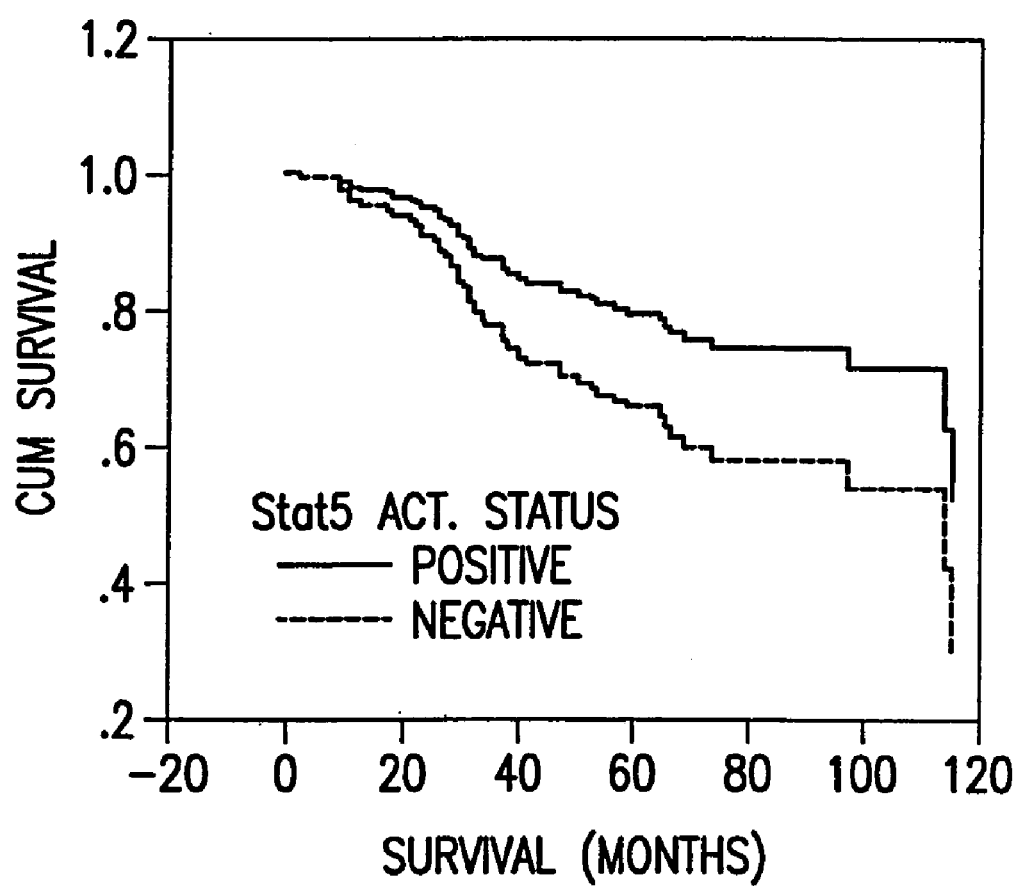
FIG. 8—Survival function for Stat5 activation status. Cox regression curves for overall survival in breast cancer patients with either positive or negative Stat5 activation status of the primary tumor. Note that positive Stat5 activation status predicts improved response to antiestrogen therapy on this overall material of node-positive and node-negative breast cancer material.

The reduced risk of micrometastatic breast cancer associated with positive Stat5 activation status could be used to favor less invasive breast conserving surgery, or lumpectomy, over mastectomy. To examine whether patients with positive Stat5 activation status could be safely treated with lumpectomy, occurrence of recurrent disease (relapse) in breast cancer patients who had undergone lumpectomy were compared with respect to the Stat5 activation status of their primary tumors (FIG. 7). Among 47 patients with node negative breast cancer with positive Stat5 activation status, no failures of lumpectomy treatment were observed. In contrast, among 51 corresponding patients with negative Stat5 activation status, metastatic disease occurred in 7 patients (14%; p=0.003 by log rank analysis) during the observation period. Therefore, we conclude that lumpectomy is a safe procedure for patients with localized breast cancer and positive Stat5 activation status. Thus, Stat5 activation status may justify the use of less invasive lumpectomy instead of mastectomy in breast cancer patients with node-negative disease.

Impact of Stat5 activation status of primary tumors on use of supplementary radiation therapy.

Although it is generally accepted that lumpectomy is as effective as mastectomy on overall survival of breast cancer patients with node-negative disease (stage I and II), lumpectomy alone is associated with a moderately increased risk of local recurrence (Reid and Donohue 1992; Schnitt 1998). However, supplementary radiation given following lumpectomy eliminates this increased risk of local recurrence, and is therefore typically used as a supplement to lumpectomy (Noguchi, Kinne et al. 1996; Taghian and Powell 1999). Nontheless, there is currently a significant extent of overtreatment with radiation therapy and markers have been sought to better define subpopulations of patients who might not need radiation therapy (Morrow, Harris et al. 1995; Marks and Prosnitz 1997; Marks and Prosnitz 1997; Schnitt 1998). The reduced risk of micrometastatic breast cancer and disease progression associated with positive Stat5 activation status therefore could be useful to identify a subpopulation of patients with node-negative disease who might not need supplementary radiation therapy in addition to lumpectomy.

Furthermore, there are several subgroups of patients in whom radiotherapy currently is specifically not recommended, which has led to the recommendation that complete removal of the breast (modified radical mastectomy) should be used for these groups of patients (1999). Among these are pregnant breast cancer patients, due to the harmful effects of radiation on the developing fetus. Likewise, breast cancer patients with certain connective tissue diseases that make body tissues especially sensitive to the side effects of radiation are also currently recommended to undergo mastectomy. Other examples of subgroups of patients who are not offered lumpectomy because of the danger of supplementary radiation include patients who have already had radiation therapy to the affected breast or chest, and patients whose initial excisional biopsy—or, when needed, their reexcision—has not completely removed their cancers. The reduced risk of micrometastatic breast cancer associated with positive Stat5 activation status may define a subgroup of these patients who could be safely treated with lumpectomy without the need for supplementary radiation therapy. Therefore, active Stat5 status in primary, node-negative breast cancer patients may identify patients for which lumpectomy can be used without need for supplementary radiation therapy.

Furthermore, also in many cases where a modified radical mastectomy is selected as the primary treatment, current guidelines make recommendations as to whether the patient should use supplementary radiation and/or chemotherapy after surgery (1999). For example, it is recommended that post-surgery radiation and chemotherapy be used when the primary tumor is larger than 5 centimeters, even when the breast cancer is node-negative and the margins are uninvolved with cancer. The reduced risk of micrometastatic breast cancer associated with positive Stat5 activation status could identify also among these patients with large tumors a subgroup with such excellent prognosis that they may not benefit from supplementary radiation therapy.

Impact of Stat5 Activation Status of Primary Tumors on Use of Adjuvant Antiestrogen Therapy Stat5 activation status of primary tumors may affect the choice of antiestrogen treatment in at least two ways. As part of the current invention positive Stat5 activation status in primary tumors was predictive of increased success of antiestrogen treatment by univariate Cox regression analysis (odds ratio=1.8, 95% confidence limits 1.0-3.2; p=0.043). Thus, in the absence of other information, positive Stat5 activation status of a primary tumor may favor the use to antiestrogen treatment by predicting a moderately improved outcome.

However, in node-negative breast cancer patients who did not receive any adjuvant therapy, the exceptionally low risk of micrometastatic breast cancer associated with positive Stat5 activation status could be useful to eliminate the need for adjuvant antiestrogen therapy in these patients. Thus breast cancer patients with low risk for distant spread of tumors could be spared from costly and potentially toxic adjuvant antiestrogen treatment. This is important because, in addition to high cost over a typical 5 year treatment period, anti-estrogen treatment with tamoxifen is associated with potentially serious morbidity and side-effects. For instance, studies have shown an increase of early-stage endometrial cancer (which occurs in the lining of the uterus) among post-menopausal women taking tamoxifen (Cardosi and Fiorica 2000). Another potential side-effect of tamoxifen is deep vein thrombosis, a condition in which blood clots form in the deep blood vessels of the legs and groin. The blood clots sometimes break off and spread to the lungs as a life-threatening complication. The risk of stroke is also somewhat increased. Other side effects are hot flashes, mood swings, and cataracts (Rennie 1993; Gail, Costantino et al. 1999). New tumor markers that will identify patients with very good prognosis may eliminate the need for adjuvant antiestrogen therapy in this group of patients.

Impact of Stat5 Activation Status of Primary Tumors on Use of Adjuvant Chemotherapy As for antiestrogen therapy, knowledge of Stat5 activation status in the primary tumor is useful to significantly help to identify low-risk breast cancer patients with node negative disease who may be spared from costly and toxic adjuvant chemotherapy. Chemotherapy is frequently used for node-negative breast cancer and is typically administered over 3-6 months is associated with significant side-effects and morbidity. Doxorubicin and epirubicin may cause heart damage, but doctors limit the dose and perform periodic tests to check heart function in order to prevent this side effect. Temporary side effects might include loss of appetite, nausea and vomiting, mouth sores, hair loss, and changes in the menstrual cycle. Because chemotherapy can damage the blood-producing cells of the bone marrow, a drop in white blood cells can raise a patient's risk of infection; a shortage of blood platelets can cause bleeding or bruising after minor cuts or injuries; and a decline in red blood cells can lead to fatigue.

It has been argued that patients can fend off many of these side effects. For example, several drugs can prevent or reduce nausea and vomiting. A new group of drugs called growth factors can help bone marrow recover after chemotherapy and can treat problems resulting from low blood counts. However, these drugs, especially growth factors such as Epogen and Neupogen are very costly, may not prolong survival, and may come with additional side effects (Del Mastro and Venturini 1998; Meadowcroft, Gilbert et al. 1998; Viens, Genre et al. 1998). In addition, patients may also experience permanent complications from anti-cancer drugs: premature menopause and infertility. The older a women is when she receives chemotherapy, the more likely she will stop menstruating or lose her ability to become pregnant. Therefore, if new tumor markers can identify patients with low risk for disease progression, adjuvant chemotherapy with its associated risks and side-effects may not be recommendable for these low-risk patients. This may also include neoadjuvant chemoptherapy which sometimes is given before initial surgery.

Impact of Stat5 Activation Status of Primary Tumors on Patient Follow-up.

The excellent prognosis associated with positive Stat5 activation status in node-negative breast cancer patients could also affect treatment by leading to reduced frequency of patient follow-up. Routine surveillance and follow-up for all patients who have had invasive breast cancer typically includes the following: a history and physical exam every 4-6 months for 2 years, then every 6 months for 3 years, and then, once every year. Women who have had a lumpectomy should undergo mammography of the treated breast at 6 months after radiation therapy, and then mammography of both breasts on an annual basis. Because tamoxifen increases a postmenopausal woman's risk developing cancer of the endometrium, postmenopausal patients taking this drug also need to have an annual pelvic exam.

If positive Stat5 activation status of primary breast cancer in node-negative patients reduces the need for adjuvant tamoxifen (antiestrogen) therapy, there would be a direct benefit in reduced need for pelvic examination. More importantly, an excellent prognosis may allow a general reduction in frequency of follow-up visits to the doctor's office, a significant benefit in terms of patient time, money and quality of life. It will also benefit society by costing less money and fewer work days will be lost.

Impact of Stat5 Activation Status on Treatment Options for Recurrent Tumors.

A recurrence may be local, meaning that cancer has returned to the breast, underarm lymph nodes, or nearby tissues, or systemic, which means that cancer has spread to distant organs. For local recurrence within the breast tissue in a patient who was first treated with lumpectomy and radiation, current guidelines suggest that a local recurrence should prompt a mastectomy, and then consideration of chemotherapy and/or hormonal therapy (1999). The good prognosis and the low risk of micrometastatic spread of cancer in patients with positive Stat5 activation status in the primary tumor could affect the treatment of locally recurrent cancer. If monitoring of the recurrent tumor through a biopsy shows that the tumor still has positive Stat5 activation status, this should signify continued good prognosis, and reexcision using breast conserving surgery might be used instead of the currently recommended and more extensive mastectomy.

Impact of Stat5 Activation Status of Primary Tumors on the Development and Application of New Treatment Approaches to Cancer.

In addition to affecting the choice and utilization of currently available breast cancer therapies, knowledge of the Stat5-activation status in primary and recurrent breast cancer may be useful for application of new breast cancer therapies. Because levels of activated Stat5 in node negative breast cancer are so closely associated with positive biological behavior of the tumor, regimes to restore activation of Stat5 in breast cancer with negative Stat5 activation status is predicted to improve outcome by re-establishing a differentiated and less invasive phenotype.

Therapies to restore Stat5 activation in Stat5 negative breast tumors may include gene therapeutic delivery of Stat5, or gene therapeutic delivery of a Stat5 activating tyrosine kinase, e.g. Jak2, or a combination of both. Alternatively, hyperactive forms of Stat5 may be used. Examples of hyperactive variants of Stat5 have been described in the literature, including point-mutants (Ariyoshi, Nosaka et al. 2000) and Jak2-Stat5 fusion proteins (Barahmand-Pour, Meinke et al. 1998). Such gene therapeutic delivery may involve viral delivery, e.g. adenoviral or adeno-associated viral vectors (Kouraklis 1999; Wu and Ataai 2000), or non-viral gene therapy, e.g. liposome-based delivery of DNA vectors (Cristiano 1998; Prince 1998). Delivery of viral or non-viral vectors may be systemic (e.g. intravenous) or local (e.g. intratumoral injection). To achieve more tissue-specific delivery to the tumor tissue, gene delivery may be combined with tissue-specific targeting strategies, which include but are not limited to tailoring of viral vectors according to tumor-specific surface markers, use of tumor-targeted inducible vectors that only express the genes of interest when a second, tumor-directed drug is used in combination. Alternatively, liposome based non-viral delivery may be targeted to tumors by various methods. Such pharmaceutical approaches for tumor-specific gene and drug delivery have been described and reviewed extensively (Huber 1989; Ohno, Levin et al. 1996; Ohno and Meruelo 1996; Berg, Selbo et al. 1999; Patterson and Harris 1999).

Oher approaches to restore Stat5 activation in breast cancer may involve use of drugs or hormones that specifically upregulate expression or activation of Stat5, or upregulate expression or activation of one or more Stat5 activating tyrosine kinases, e.g. Jak2, or inhibit or down-regulate Stat5 phosphotyrosine phosphatases. Inhibition of Stat5 tyrosine phosphatases might be achieved by use of small molecule inhibitors, antisense-based methods, or introduction of dominant-negative mutants. Examples of Stat5 activating hormones are the socalled lactogenic hormones, including human prolactin, human growth hormone, and human placetal lactogen (Bridges 1994; Wartmann, Cella et al. 1996; Handwerger and Freemark 2000). The success of such Stat5 targeted therapies may be further monitored in vivo (biopsy after initiation of treatment) of patients, or be carried out in vitro on tissue biopsy or cell culture samples, using the method of the present invention to detect levels of activated Stat5.

EXAMPLE 3

Method for Screening Compounds

The pharmaceutical industry is interested in evaluating pharmaceutically useful compounds which act as growth factor agonists or antagonists. Tens of thousands of compounds per year need to be tested in an entry level or "high flux" screening protocol. Out of the thousands of compounds scrutinized, one or two will show some activity in the entry level assay. These compounds are then chosen for further development and testing. Ideally, a screening protocol would be automated to handle many samples at once, and would not use radioisotopes or other chemicals that pose safety or disposal problems. An antibody-based approach to evaluating desired or undesired drug regulation of transcription factor activities would provide these advantages and offer the added advantage of high selectivity.

In particular, antibodies that recognize activated Stat5 may be used to for screening drugs in various screening protocols. Generally, two approaches are used. Cell or tissue based approaches use an indicator cell line or tissue that is exposed to the compound to be tested. When cells are used it is thought that this approach may quickly eliminate drugs having solubility or membrane permeability problems. Protein or enzyme-based screens may use purified proteins and can identify drugs that react with Stat5, or Stat5 tyrosine kinases, or Stat5 tyrosine phosphatases, to affect activation state of Stat5.

For cell or tissue based screening for drugs that modulate (e.g. stimulate, block, inhibit or suppress) Stat5 activation, immunohistochemistry or cytochemistry of Stat5 activation state can be used to measure the effects of individual agents. For example, human breast cancer cells, e.g. T47D cells, may be incubated with or without prolactin in the presence or absence of drug of interest. Following activation with prolactin for 15-30 min, a large proportion of intracellular Stat5 will normally become tyrosine phosphorylated and translocated to the nucleus, while Stat5 will remain unphosphorylated in cells not exposed to prolactin (see e.g. FIG. 2). By fixing cells in formalin, followed by antigen retrieval and immunocytochemistry for activated Stat5, the effect of the drug of interest on inducible and basal Stat5 activation state may be determined.

Sensitive drug screening methods have been previously proposed in the art to detect drugs that affect activation state of Stat5 and other Stat-family members based on the ability of activated Stat5 to bind to the promoter of and drive transcription of Stat-responsive reporter genes that contain the Stat consensus binding site TTNNNNNAA in their promoter regions (Lamb et al., U.S. Pat. No. 5,707,803, 1998). While this approach is fairly sensitive, and can be adapted to high throughput formats, the duration of Stat stimulation needed for transcription and translation is generally 10-16 h. During this extended time, a series of events that are unrelated to Stat activity are sensitive to disruption by non-specific drugs, including gene transcription, mRNA processing and stability, translation, and protein modification. It is therefore expected that a large number of drugs affecting this process will work through a non-Stat-dependent mechanism. This will result in many false positives, and will require additional control experiments. In addition, this DNA-based approach requires the use of transfection of cells either transiently or stably with a reporter gene construct, which limits the use of this approach to cells that are effectively transfectable and excludes the use of primary tumor cells or normal cells, which may be more physiologically and biologically relevant. These disadvantages are overcome by the method of the current invention.

Figure 9:
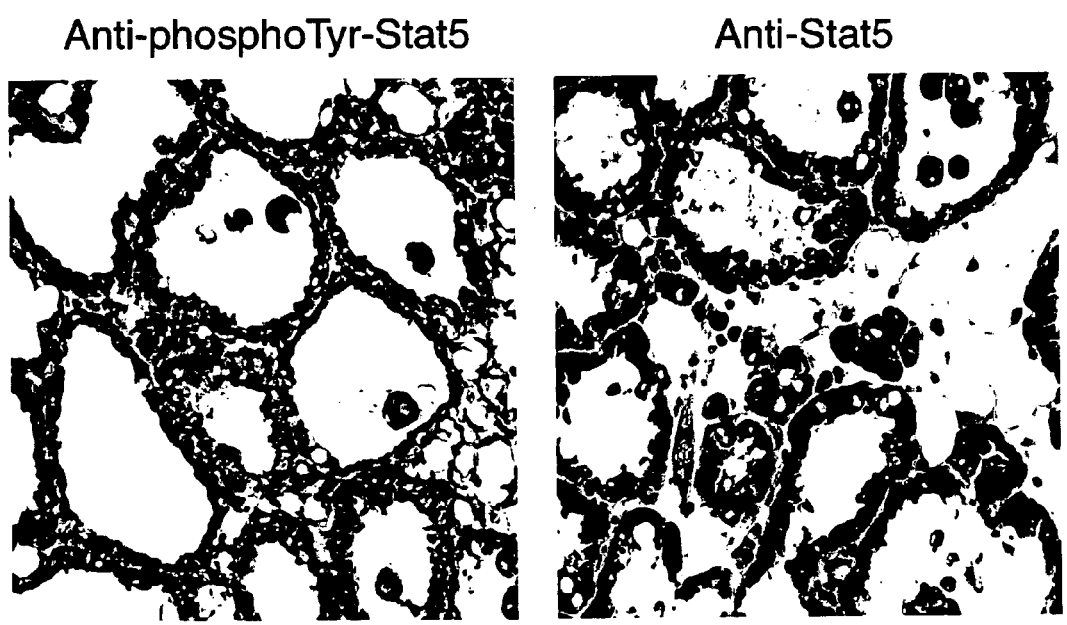
FIG. 9—Immunohistochemical analysis of activated Stat5 with Ax1 anti-phosphoTyr-Stat5 antibody and a general antibody to Stat5. This figure documents that at least in post-lactational mouse mammary glands (involution), when Stat5 is known to be turned off, AX1 does not detect activated Stat5 in cell nuclei (left panel), whereas a general Stat5 antibody detect significant levels (right panel). Thus, a general Stat5 antibody will not accurately detect levels of active Stat5 even if Stat5 is located in the cell nucleus.

A second method of studying Stat5 activation that may be useful for drug screening is marketed by Cellomics, Inc (635 William Pitt Way, Pittsburgh, Pa. 15238; "Stat5 activation HitKit"; Cat no. K01-0009-1). This method is based on direct detection of Stat5 localized to the nucleus of cells using regular anti-Stat5 antibodies in an immunocytochemical approach. While this method may in many experimental settings give an indication of Stat5 activation, this method is less precise than the method of the present invention which takes advantage of detecting tyrosine phosphorylated or dimerized Stat5 in the cell nucleus with specific anti-phospho-Stat5a/b(pTyr694/699) antibodies. Although there is probably a general correlation between nuclear levels of Stat5 and degree of Stat5 activation in a given cell, we have found based on several experimental models that levels of Stat5 protein in cell nuclei frequently do not correspond to the levels of activated Stat5 in the cell nucleus as measured by anti-phospho-Stat5a/b(pTyr694/699) antibodies. Specifically, in post-lactational mouse mammary glands a huge discrepancy was observed, showing that there can be significant levels of Stat5 detectable in cell nuclei that do not represent active Stat5 as determined by anti-phospho-Stat5a/b(pTyr694/699) antibodies in the same samples (FIG. 9). In cultured normal rat prostates a similar discrepancy between nuclear Stat5 protein levels and levels of activated Stat5 as measured by AX1 antibodies (not shown). Although Cellomic Inc's assay for Stat5 activation may be useful in many circumstances, it is evident that the Cellomic Inc's methods has the potential to give erroneous results in cases where nuclear Stat5 levels do not correspond to Stat5 activation. This disadvantage is overcome by the method of the current invention.

In contrast to previous methods, the proposed method will be able to accurately screen for drugs that affect Stat5 activation levels in normal and tumor cells that have not been transfected with artificial DNA. Furthermore, because the proposed screening method assays for Stat5 tyrosine phosphorylation and nuclear translocation, which should occur within 15-60 min of stimulation or exposure to a candidate drug, and does not include a readout that is dependent on proper transcription, mRNA processing, and translation of a gene product, the new method represents a clear improvement to the reporter-gene based assay types.

An immunohistochemistry-based method that accurately detects levels of activated Stat5 also has the advantage that it may be used with solid tumor explant cultures and organoid cultures, and therefore allows accurate detection of Stat5-modulating drugs in more physiologically relevant environmental settings than those used by other methods. Furthermore, the proposed method will also be applicable to screening and monitoring the effect of drugs on Stat5 activation state in tissues and cells in research animals and humans in vivo. Samples may be obtained by biopsy (e.g. fine needle aspiration, section) or by tissue harvesting in the case of research animals and then subjected to the methods of the invention.

The proposed method is highly sensitive, because Stat5 activation state, in principle, may be monitored in a single cell. For practical use, more cells may be needed, but good analytic estimates can certainly be obtained with as little as 20-100 cells.

The foregoing specification, including the specific embodiments and examples, is intended to be illustrative of the present invention and is not to be taken as limiting. Numerous other variations and modification can be effected without departing from the true spirit and scope of the present invention. All publications, patents and patent applications cited herein are incorporated by reference in their entirety into the disclosure.

(1999). "Update: NCCN practice guidelines for the treatment of breast cancer. National Comprehensive Cancer Network." *Oncology (Huntingt)* 13(5A): 41-66.

Allred, D. C., J. M. Harvey, et al. (1998). "Prognostic and predictive factors in breast cancer by immunohistochernical analysis." *Mod Pathol* 11(2): 155-68.

Apantaku, L. M. (2000). "Breast cancer diagnosis and screening." *Am Fam Physician* 62(3): 596-602, 605-6.

Ariyoshi, K., T. Nosaka, et al. (2000). "Constitutive activation of STAT5 by a point mutation in the SH2 domain." *J Biol Chem* 275(32): 24407-13.

Ausubel, F. M. (1988). *Current protocols in molecular biology*. New York, Published by Greene Pub. Associates and Wiley-Interscience: J. Wiley.

Azam, M., C. Lee, et al. (1997). "Functionally distinct isoforms of STAT5 are generated by protein processing." *Immunity* 6(6): 691-701.

Barahmand-Pour, F., A. Meinke, et al. (1998). "Jak2-Stat5 interactions analyzed in yeast." *J Biol Chem* 273(20): 12567-75.

Berg, K., P. K. Selbo, et al. (1999). "Photochemical internalization: a novel technology for delivery of macromolecules into cytosol." *Cancer Res* 59(6): 1180-3.

Berois, N., M. Varangot, et al. (2000). "Molecular detection of cancer cells in bone marrow and peripheral blood of patients with operable breast cancer. Comparison of CK19, MUC1 and CEA using RT-PCR." *Eur J Cancer* 36(6): 717-23.

Bishayee, A., L. Beguinot, et al. (1999). "Phosphorylation of tyrosine 992, 1068, and 1086 is required for conformational change of the human epidermal growth factor receptor c-terminal tail." *Mol Biol Cell* 10(3): 525-36.

Boon, M. E. and L. P. Kok (1994). "Microwaves for immunohistochemistry." *Micron* 25(2): 151-70.

Braun, S., K. Pantel, et al. (2000). "Cytokeratin-positive cells in the bone marrow and survival of patients with stage I, II, or III breast cancer N Engl J Med Jul. 27, 2000;343(4):308]." *N Engl J Med* 342(8): 525-33.

Bridges, R. S. (1994). "The role of lactogenic hormones in maternal behavior in female rats." *Acta Paediatr Suppl* 397: 33-9.

Bromberg, J. and J. E. Darnell, Jr. (2000). "The role of STAT5 in transcriptional control and their impact on cellular function." *Oncogene* 19(21): 2468-73.

Brown, C. (1998). "Antigen retrieval methods for immunohistochemistry." *Toxicol Pathol* 26(6): 830-1.

Calabresi, P. and P. S. Schein (1993). *Medical oncology: basic principles and clinical management of cancer*. New York, McGraw-Hill Health Professions Division.

Cardosi, R. J. and J. V. Fiorica (2000). "Surveillance of the endometrium in tamoxifen treated women." *Curr Opin Obstet Gynecol* 12(1): 27-31.

Chen, J., H. B. Sadowski, et al. (1997). "Stat5 is a physiological substrate of the insulin receptor." *Proc Natl Acad Sci USA* 94(6): 2295-300.

Cochrane, D., C. Webster, et al. (2000). "Identification of natural ligands for SH2 domains from a phage display cDNA library." *J Mol Biol* 297(1): 89-97.

Cole, P. (1980). "Major aspects of the epidemiology of breast cancer." *Cancer* 46(4 Suppl): 865-7.

Cox, D. R. (1972) "Regression models and life tables (with discussion.) *J. Royal Statistical Society* 34 (Series B), pp 187-220.

Cristiano, R. J. (1998). "Targeted, non-viral gene delivery for cancer gene therapy." *Front Biosci* 3: D1161-70.

Dahiya, R. and G. Deng (1998). "Molecular prognostic markers in breast cancer." *Breast Cancer Res Treat* 52(1-3): 185-200.

Darnell, J. E., Jr. (1997). "STAT5 and gene regulation." *Science* 277(5332): 1630-5.

Darnell, J. E., Jr. (1998). "Studies of IFN-induced transcriptional activation uncover the Jak-Stat pathway." *J Interferon Cytokine Res* 18(8): 549-54.

Del Mastro, L: and M. Venturini (1998). "Strategies for the Use of Epoetin Alfa in Breast Cancer Patients." *Oncologist* 3(5): 314-318.

Dente, L., C. Vetriani, et al. (1997). "Modified phage peptide libraries as a tool to study specificity of phosphorylation and recognition of tyrosine containing peptides." *J Mol Biol* 269(5): 694-703.

DeVita, V. T., S. Hellman, et al. (1982). *Cancer: principles and practice of oncology*. Philadelphia, Lippincott Co.

Doi, N. and H. Yanagawa (1998). "Screening of conformationally constrained random polypeptide libraries displayed on a protein scaffold." *Cell Mol Life Sci* 54(5): 394-404.

Doi, N. and H. Yanagawa (1999). "STABLE: protein-DNA fusion system for screening of combinatorial protein libraries in vitro." *FEBS Lett* 457(2): 227-30.

Elledge, R. M. and W. L. McGuire (1993). "Prognostic factors and therapeutic decisions in axillary node-negative breast cancer." *Annu Rev Med* 44: 201-10.

Fetsch, P. A., K. H. Cowan, et al. (2000). "Detection of circulating tumor cells and micrometastases in stage II, III, and IV breast cancer patients utilizing cytology and immunocytochemistry." *Diagn Cytopathol* 22(5): 323-8.

Fitzgibbons, P. L., D. L. Page, et al. (2000). "Prognostic factors in breast cancer. College of American Pathologists Consensus Statement 1999." *Arch Pathol Lab Med* 124 (7): 966-78.

Freije, J. M., N. J. MacDonald, et al. (1998). "Nm23 and tumour metastasis: basic and translational advances." *Biochem Soc Symp* 63: 261-71.

Fresno, M., R. Molina, et al. (1997). "p53 expression is of independent predictive value in lymph node-negative breast carcinoma." *Eur J Cancer* 33(8): 1268-74.

Gail, M. H., J. P. Costantino, et al. (1999). "Weighing the risks and benefits of tamoxifen treatment for preventing breast cancer" J Natl Cancer Inst Feb. 2, 2000;92(3): 275]." *J Natl Cancer Inst* 91(21): 1829-46.

Glockshuber, R., M. Malia, et al. (1990). "A comparison of strategies to stabilize immunoglobulin Fv-fragments." *Biochemistry* 29(6): 1362-7.

Gouilleux, F., H. Wakao, et al. (1994). "Prolactin induces phosphorylation of Tyr694 of Stat5 (MGF), a prerequisite for DNA binding and induction of transcription." *Embo J* 13(18): 4361-9.

Gram, H. (1999). "Phage display in proteolysis and signal transduction." *Comb Chem High Throughput Screen* 2(1): 19-28.

Gram, H., R. Schmitz, et al. (1997). "Identification of phosphopeptide ligands for the Src-homology 2 (SH2) domain of Grb2 by phage display." *Eur J Biochem* 246(3): 633-7.

Grimley, P. M., F. Dong, et al. (1999). "Stat5a and Stat5b: fraternal twins of signal transduction and transcriptional activation." *Cytokine Growth Factor Rev* 10(2): 131-57.

Hanahan, D. and R. A. Weinberg (2000). "The hallmarks of cancer." *Cell* 100(1): 57-70.

Handwerger, S. and M. Freemark (2000). "The roles of placental growth hormone and placental lactogen in the regulation of human fetal growth and development." *J Pediatr Endocrinol Metab* 13(4): 343-56.

Hankinson, S. E., W. C. Willett, et al. (1999). "Plasma prolactin levels and subsequent risk of breast cancer in postmenopausal women." *J Natl Cancer Inst* 91(7): 629-34.

Harlow, E. and D. Lane (1988). *Antibodies: a laboratory manual.* Cold Spring Harbor, N.Y., Cold Spring Harbor Laboratory.

Hart, I. R. and D. Easty (1991). "Tumor cell progression and differentiation in metastasis." *Semin Cancer Biol* 2(2): 87-95.

Haspel, R. L. and J. E. Darnell, Jr. (1999). "A nuclear protein tyrosine phosphatase is required for the inactivation of Stat1." *Proc Natl Acad Sci USA* 96(18): 10188-93.

Horn, I. R., A. Wittinghofer, et al. (1999). "Selection of phage-displayed fab antibodies on the active conformation of ras yields a high affinity conformation-specific antibody preventing the binding of c-Raf kinase to Ras." *FEBS Lett* 463(1-2): 115-20.

Hosmer, D. W. and S. Lemeshow (1999) "Applied survival analysis: regression modeling of time to event data. (Wiley Series in Probability and Statistics) New York, Wiley Publisher ISBN 0471154105

Huber, B. E. (1989). "Therapeutic opportunities involving cellular oncogenes: novel approaches fostered by biotechnology." *Faseb J* 3(1): 5-13.

Humphreys, R. C. and L. Hennighausen (1999). "Signal transducer and activator of transcription 5a influences mammary epithelial cell survival and tumorigenesis." *Cell Growth Differ* 10(10): 685-94.

Humphreys, R. C. and L. Hennighausen (2000). "Transforming growth factor alpha and mouse models of human breast cancer." *Oncogene* 19(8): 1085-91.

Igarashi, K., K. Shigeta, et al. (1998). "Sck interacts with KDR and Flt-1 via its SH2 domain." *Biochem Biophys Res Commun* 251(1): 77-82.

Ikeda, N., Y. Miyoshi, et al. (2000). "Prognostic Significance of Occult Bone Marrow Micrometastases of Breast Cancer Detected by Quantitative Polymerase Chain Reaction for Cytokeratin 19 mRNA." *Jpn J Cancer Res* 91(9): 918-924.

Illgen, K., T. Enderle, et al. (2000). "Simulated molecular evolution in a full combinatorial library." *Chem Biol* 7(6): 433-41.

Jones, F. E., T. Welte, et al. (1999). "ErbB4 signaling in the mammary gland is required for lobuloalveolar development and Stat5 activation during lactation." *J Cell Biol* 147(1): 77-88.

Kaplan, E. L., Meier, P. (1958). *J. Am. Stat. Assoc.* 53: 457.

Kazansky, A. V., E. B. Kabotyanski, et al. (1999). "Differential effects of prolactin and src/abl kinases on the nuclear translocation of STAT5B and STAT5A." *J Biol Chem* 274(32): 22484-92.

Kelly, M. A., H. Liang, et al. (1996). "Characterization of SH2-ligand interactions via library affinity selection with mass spectrometric detection." *Biochemistry* 35(36): 11747-55.

Kinzler, K. W. and B. Vogelstein (1996). "Lessons from hereditary colorectal cancer." *Cell* 87(2): 159-70.

Kirken, R. A., M. G. Malabarba, et al. (1997). "Prolactin stimulates serine/tyrosine phosphorylation and formation of heterocomplexes of multiple Stat5 isoforms in Nb2 lymphocytes." *J Biol Chem* 272(22): 14098-103.

Kohler, G. and C. Milstein (1975). "Continuous cultures of fused cells secreting antibody of predefined specificity." *Nature* 256(5517): 495-7.

Kononen, J., L. Bubendorf, et al. (1998). "Tissue microarrays for high-throughput molecular profiling of tumor specimens" *Nat Med* 4(7): 844-7.

Kouraklis, G. (1999). "Progress in cancer gene therapy." *Acta Oncol* 38(6): 675-83.

Kraeft, S. K., R. Sutherland, et al. (2000). "Detection and analysis of cancer cells in blood and bone marrow using a rare event imaging system." *Clin Cancer Res* 6(2): 434-42.

Krenacs, L., T. Krenacs, et al. (1999). "Antigen retrieval for immunohistochemical reactions in routinely processed paraffin sections." *Methods Mol Biol* 115: 85-93.

Lacronique, V., A. Boureux, et al. (1997). "A TEL-JAK2 fusion protein with constitutive kinase activity in human leukemia." *Science* 278(5341): 1309-12.

Lamoyi, E. and A. Nisonoff (1983). "Preparation of F(ab')2 fragments from mouse IgG of various subclasses." *J Immunol Methods* 56(2): 235-43.

Lavabre-Bertrand, T., F. George, et al. (1994). "Quantitative immune phenotyping: a new dimension for the monitoring of haemopoietic malignancies." *Nouv Rev Fr Hematol* 36(5): 373-82.

Lee, C., F. Piazza, et al. (1999). "Characterization of the Stat5 protease." *J Biol Chem* 274(38): 26767-75.

Lengauer, C., K. W. Kinzler, et al. (1998). "Genetic instabilities in human cancers." *Nature* 396(6712): 643-9.

Leonard, W. J. and J. J. O'Shea (1998). "Jaks and STATS: biological implications." *Annu Rev Immunol* 16: 293-322.

Liu, F. and R. A. Roth (1995). "Grb-IR: a SH2-domain-containing protein that binds to the insulin receptor and inhibits its function." *Proc Natl Acad Sci USA* 92(22): 10287-91.

Liu, K. D., S. L. Gaffen, et al. (1998). "JAK/STAT signaling by cytokine receptors." *Curr Opin Immunol* 10(3): 271-8.

Liu, X., G. W. Robinson, et al. (1995). "Cloning and expression of Stat5 and an additional homologue (Stat5b) involved in prolactin signal transduction in mouse mammary tissue." *Proc Natl Acad Sci USA* 92(19): 8831-5.

Liu, X., G. W. Robinson, et al. (1997). "Stat5a is mandatory for adult mammary gland development and lactogenesis." *Genes Dev* 11(2): 179-86.

Marks, L. B. and L. R. Prosnitz (1997). "Lumpectomy with and without radiation for early-stage breast cancer and DCIS." *Oncology (Huntingt)* 11(9): 1361-8, 1371; discussion 1372, 1374.

Marks, L. B. and L. R. Prosnitz (1997). "The role of radiation therapy after local excision of invasive and noninvasive breast cancer." *Surg Oncol Clin N Am* 6(2): 359-79.

Matthew, W. D. and L. F. Reichardt (1982). "Development and application of an efficient procedure for converting mouse IgM into small, active fragments." *J Immunol Methods* 50(3): 239-53.

McGuire, W. L. (1991). "Breast cancer prognostic factors: evaluation guidelines." *J Natl Cancer Inst* 83(3): 154-5.

McGuire, W. L., A. K. Tandon, et al. (1992). "Prognosis and treatment decisions in patients with breast cancer without axillary node involvement." *Cancer* 70(6 Suppl): 1775-81.

McNicol, A. M. and J. A. Richmond (1998). "Optimizing immunohistochemistry: antigen retrieval and signal amplification." *Histopathology* 32(2): 97-103.

Meadowcroft, A. M., C. J. Gilbert, et al. (1998). "Cost of managing anemia with and without prophylactic epoetin alfa therapy in breast cancer patients receiving combination chemotherapy." *Am J Health Syst Pharm* 55(18): 1898-902.

Messmer, B. T., C. J. Benham, et al. (2000). "Sequential determination of ligands binding to discrete components in heterogeneous mixtures by iterative panning and blocking (IPAB)." *J Mol Biol* 296(3): 821-32.

Meyer, J., M. Jucker, et al. (1998). "Carboxyl-truncated STAT5beta is generated by a nucleus-associated serine protease in early hematopoietic progenitors." *Blood* 91(6): 1901-8.

Mighell, A. J., W. J. Hume, et al. (1998). "An overview of the complexities and subtleties of immunohistochemistry." *Oral Dis* 4(3): 217-23.

Moriggl, R., D. J. Topham, et al. (1999). "Stat5 is required for 1L-2-induced cell cycle progression of peripheral T cells." *Immunity* 10(2): 249-59.

Morrison, S. L., M. J. Johnson, et al. (1984). "Chimeric human antibody molecules: mouse antigen-binding domains with human constant region domains." *Proc Natl Acad Sci USA* 81(21): 6851-5.

Morrow, M., J. R. Harris, et al. (1995). "Local control following breast-conserving surgery for invasive cancer: results of clinical trials." *J Natl Cancer Inst* 87(22): 1669-73.

Neuberger, M. S., G. T. Williams, et al. (1984). "Recombinant antibodies possessing novel effector functions." *Nature* 312(5995): 604-8.

Nevalainen, M. T., T. J. Ahonen, et al. (2000). "Epithelial defect in prostates of Stat5a-null mice." *Lab Invest* 80(7): 993-1006.

Noguchi, M., D. W. Kinne, et al. (1996). "Breast-conserving treatment: controversies and consensus." *J Surg Oncol* 62(3): 228-34.

Noguchi, M. and I. Miyazaki (1994). "Breast conserving surgery and radiation in the treatment of operable breast cancer." *Int Surg* 79(2): 142-7.

Ohno, K., B. Levin, et al. (1996). "Cell-specific, multidrug delivery system using streptavidin-protein A fusion protein." *Biochem Mol Med* 58(2): 227-33.

Ohno, K. and D. Meruelo (1996). "Multi-drug delivery system using streptavidin-transforming growth factor-alpha chimeric protein." *DNA Cell Biol* 15(5): 401-6.

Ormerod, M. G. (2000). *Flow cytometry: a practical approach*. Oxford; N.Y., Oxford University Press.

Orr, R. K., J. L. Hoehn, et al. (1999). "The learning curve for sentinel node biopsy in breast cancer: practical considerations." *Arch Surg* 134(7): 764-7.

Panneerselvam, K., H. Reitz, et al. (1995). "A conformation-specific anti-peptide antibody to the beta-type platelet-derived growth factor receptor also recognizes the activated epidermal growth factor receptor." *J Biol Chem* 270(14): 7975-9.

Parham, P. (1983). "On the fragmentation of monoclonal IgG1, IgG2a, and IgG2b from BALB/c mice." *J Immunol* 131(6): 2895-902.

Parham, P., M. J. Androlewicz, et al. (1982). "Monoclonal antibodies: purification, fragmentation and application to structural and functional studies of class I MHC antigens." *J Immunol Methods* 53(2): 133-73.

Parkin, D. M. (1998). "Epidemiology of cancer: global patterns and trends." *Toxicol Lett* 102-103: 227-34.

Patterson, A. and A. L. Harris (1999). "Molecular chemotherapy for breast cancer." *Drugs Aging* 14(2): 75-90.

Pellegrini, M. C., H. Liang, et al. (1998). "Mapping the subsite preferences of protein tyrosine phosphatase PTP-1B using combinatorial chemistry approaches." *Biochemistry* 37(45): 15598-606.

Pharoah, P. D., N. E. Day, et al. (1999). "Somatic mutations in the p53 gene and prognosis in breast cancer: a meta-analysis." *Br J Cancer* 80(12): 1968-73.

Piazza, F., J. Valens, et al. (2000). "Myeloid differentiation of FdCPI cells is dependent on Stat5 processing." *Blood* 96(4): 1358-65.

Prince, H. M. (1998). "Gene transfer: a review of methods and applications." *Pathology* 30(4): 335-47.

Reid, I. M. and J. H. Donohue (1992). "The biological significance of locoregional recurrence following breast conserving therapy." *Semin Surg Oncol* 8(3): 113-6.

Rennie, I. G. (1993). "Clinically important ocular reactions to systemic drug therapy." *Drug Saf* 9(3): 196-211.

Rivadeneira, D. E., R. M. Simmons, et al. (2000). "Predictive factors associated with axillary lymph node metastases in T1a and T1b breast carcinomas: analysis in more than 900 patients." *J Am Coll Surg* 191(1): 1-6; discussion 6-8.

Rousseaux, J., R. Rousseaux-Prevost, et al. (1986). "Optimal conditions for the preparation of proteolytic fragments from monoclonal IgG of different rat IgG subclasses." *Methods Enzymol* 121: 663-9.

Sambrook, J., T. Maniatis, et al. (1989). *Molecular cloning: a laboratory manual*. Cold Spring Harbor, N.Y., Cold Spring Harbor Laboratory.

Schnitt, S. J. (1998). "Can we identify patients with invasive breast cancer adequately treated with breast-conserving surgery alone?" *Mod Pathol* 11(2): 129-33.

Schraml, P., J. Kononen, et. al. (1999). "Tissue microarrays for gene amplification surveys in many different tumor types." *Clin Cancer Res* 5(8): 1966-75.

Shepherd, P. S. and C. J. Dean (2000). *Monoclonal antibodies: a practical approach*. Oxford; N.Y., Oxford University Press.

Shi, S. R., R. J. Cote, et al. (1997). "Antigen retrieval immunohistochemistry: past, present, and future." *J Histochem Cytochem* 45(3): 327-43.

Sikora, K. and H. M. Smedley (1984). *Monoclonal antibodies*. Oxford; Boston, Blackwell Scientific Publications; St Louis Mo.: Distributors USA Blackwell Mosby Book.

Simmons, R. M. and M. P. Osborne (1999). "The evaluation of high risk and pre-invasive breast lesions and the decision process for follow up and surgical intervention." *Surg Oncol* 8(2): 55-65.

Slamon, D. J., G. M. Clark, et al. (1987). "Human breast cancer: correlation of relapse and survival with amplification of the HER-2/neu oncogene." *Science* 235(4785): 177-82.

Spira, G., M. Paizi, et al. (1996). "Generation of biologically active anti-*Cryptococcus neoformans* IgG, IgE and IgA isotype switch variant antibodies by acridine orange mutagenesis." *Clin Exp Immunol* 105(3): 436-42.

Stebbing, J., E. Copson, et al. (2000). "Herceptin (trastuzamab) in advanced breast cancer." *Cancer Treat Rev* 26(4): 287-90.

Stoll, B. A. (1998). "Western diet, early puberty, and breast cancer risk." *Breast Cancer Res Treat* 49(3): 187-93.

Styblo, T. M. and W. C. Wood (1999). "The management of ductal and lobular breast cancer." *Surg Oncol* 8(2): 67-75.

Sugg, S. L., D. J. Ferguson, et al. (2000). "Should internal mammary nodes be sampled in the sentinel lymph node era?" *Ann Surg Oncol* 7(3): 188-92.

Taghian, A. G. and S. N. Powell (1999). "The role of radiation therapy for primary breast cancer." *Surg Clin North Am* 79(5): 1091-115.

Tandon, A. K., G. M. Clark, et al. (1989). "HER-2/neu oncogene protein and prognosis in breast cancer." *J Clin Oncol* 7(8): 1120-8.

Teglund, S., C. McKay, et al. (1998). "Stat5a and Stat5b proteins have essential and nonessential, or redundant, roles in cytokine responses." *Cell* 93(5): 841-50.

Thammana, P. and M. D. Scharff (1983). "Immunoglobulin heavy chain class switch from IgM to IgG in a hybridoma." *Eur J Immunol* 13(8): 614-9.

Thomssen, C. and F. Janicke (2000). "Do we need better prognostic factors in node-negative breast cancer?." *Eur J Cancer* 36(3): 293-8.

Tubiana, M. (1999). "Contribution of human data to the analysis of human carcinogenesis." *C R Acad Sci III* 322(2-3): 215-24.

Udy, G. B., R. P. Towers, et al. (1997). "Requirement of STAT5b for sexual dimorphism of body growth rates and liver gene expression." *Proc Natl Acad Sci USA* 94(14): 7239-44.

Viens, P., D. Genre, et al. (1998). "Benefits of granulocyte-colony-stimulating factor after stem cell transfusion in intensive sequential chemotherapy for breast cancer." *Eur Cytokine Netw* 9(1): 93-8.

Vomachka, A. J., S. L. Pratt, et al. (2000). "Prolactin gene-disruption arrests mammary gland development and retards T-antigen-induced tumor growth." *Oncogene* 19(8): 1077-84.

Wellbrock, C., E. Geissinger, et al. (1998). "Signalling by the oncogenic receptor tyrosine kinase Xmrk leads to activation of STAT5 in Xiphophorus melanoma." *Oncogene* 16(23): 3047-56.

Welte, T., D. Leitenberg, et al. (1999). "STAT5 interaction with the T cell receptor complex and stimulation of T cell proliferation." *Science* 283(5399): 222-5.

Winter, G. and C. Milstein (1991). "Man-made antibodies." *Nature* 349(6307): 293-9.

Wu, N. and M. M. Ataai (2000). "Production of viral vectors for gene therapy applications." *Curr Opin Biotechnol* 11(2): 205-8.

Yamashita, H., J. Xu, et al. (1998). "Differential control of the phosphorylation state of proline-juxtaposed serine residues Ser725 of Stat5a and Ser730 of Stat5b in prolactin-sensitive cells." *J Biol Chem* 273(46): 30218-24.

Zhang, Z., W. Zhu, et al. (2000). "Selection and application of peptide-binding peptides." *Nat Biotechnol* 18(1): 71-4.

Zhong, X. Y., S. Kaul, et al. (2000). "Sensitive detection of micrometastases in bone marrow from patients with breast cancer using immunomagnetic isolation of tumor cells in combination with reverse transcriptase/polymerase chain reaction for cytokeratin-19." *J Cancer Res Clin Oncol* 126(4): 212-8.

```
                       SEQUENCE LISTING

<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: Phosphopeptide used in generating monoclonal
      antibodies
<220> FEATURE:
<221> NAME/KEY: MOD_RES
<222> LOCATION: (6)..(6)
<223> OTHER INFORMATION: PHOSPHORYLATION

<400> SEQUENCE: 1

Lys Ala Val Asp Gly Tyr Val Pro Gln Ile Lys
1               5                   10
```

Wakao, H., F. Gouilleux, et al. (1994). "Mammary gland factor (MGF) is a novel member of the cytokine regulated transcription factor gene family and confers the prolactin response [published erratum appears in EMBO J Feb. 15, 1995;14(4):854-5]." *Embo J* 13(9): 2182-91.

Wang, D., D. Stravopodis, et al. (1996). "Naturally occurring dominant negative variants of Stat5." *Mol Cell Biol* 16(11): 6141-8.

Ward, E. S., D. Gussow, et al. (1989). "Binding activities of a repertoire of single immunoglobulin variable domains secreted from *Escherichia coli*." *Nature* 341(6242): 544-6.

Wartmann, M., N. Celia, et al. (1996). "Lactogenic hormone activation of Stat5 and transcription of the beta-casein gene in mammary epithelial cells is independent of p42 ERK2 mitogen-activated protein kinase activity." *J Biol Chem* 271(50): 31863-8.

What is claimed is:

1. A method of determining reduced risk of breast cancer progression, comprising:
    a) obtaining a sample of breast tissue from an individual in need of breast cancer prognosis, wherein said sample comprises cancer cells;
    b) determining positive or negative Stat5 activation status of said sample by detecting tyrosine phosphorylated Stat5 localized in cancer cell nuclei of said sample; and
    c) determining from said status a reduced risk of breast cancer progression associated with said cancer cells if the status is positive.

2. The method of claim 1 wherein said sample of breast tissue is a breast tumor sample from an individual with node-negative breast cancer.

3. The method of claim 1 wherein, in step b), said detecting comprises contacting said sample with an antibody that detects tyrosine phosphorylated Stat5.

4. The method of claim 1 wherein said detecting comprises a method selected from the group consisting of immunoblotting, immunohistochemistry and immunocytochemistry.

5. The method of claim 1 wherein said detecting comprises Fluorescence-Activated Cell Sorting (FACS).

6. The method of claim 3, wherein said antibody is an antibody to tyrosine-phosphorylated Stat5.

7. The method of claim 1 wherein said sample is a tissue section sample.

8. The method of claim 1 further comprising analyzing the levels of activated Stat5 in conjunction with additional breast cancer markers.

9. The method of claim 1 wherein, in step b), said detecting comprises treating said sample in a microwave oven or by other heat-based methods of antigen retrieval and then detecting tyrosine phosphorylated Stat5 localized in cancer cell nuclei of the resulting treated sample.

10. The method of claim 1 wherein, in step b), said detecting comprises treating said sample in a microwave oven or by another heat-based method of antigen retrieval in an appropriate antigen retrieval solution and then detecting tyrosine phosphorylated Stat5 localized in cancer cell nuclei of the resulting treated sample.

11. The method of claim 10, wherein said appropriate antigen retrieval solution is an aqueous buffer with a pH of about 7-10.

12. The method of claim 11 wherein said antigen-retrieval buffer is 1 mM Tris at pH 10.

13. The method of claim 8, wherein said analyzing comprises univariate or multivariate analysis.

14. The method of claim 3, wherein said antibody is a monoclonal antibody recognizing the phosphopeptide KAVDG(phospho Y)VKPQIK (SEQ ID NO: 1), and which specifically recognizes tyrosine phosphorylated isoforms of Stat5, but not unphosphorylated isoforms, and does not recognize Stat5 mutants in which the tyrosine residue has been substituted with phenylalanine.

15. The method of claim 1, wherein said activated Stat5 comprises Stat5 a phosphorylated on amino acid residue Tyr694.

16. The method of claim 1, wherein said activated Stat5 comprises Stat5b phosphorylated on amino acid residue Tyr699.

17. The method of claim 1 further comprising, after step c):

d) obtaining a subsequent tissue sample from a recurrent tumor in said individual, wherein said subsequent tissue sample contains breast cancer cells; and e) determining positive or negative Stat5 activation status of said subsequent sample by detecting tyrosine phosphorylated Stat5 localized in cancer cell nuclei of said subsequent sample; and f) determining from said status of step e) a reduced risk of breast cancer progression associated with said cancer cells of said subsequent tissue sample if the status of said subsequent sample is positive.

18. The method of claim 17, wherein step f) comprises determining from said positive status that radical mastectomy is not necessary.

19. The method of claim 1, wherein said breast tissue sample is a biopsy sample or a pathological archived material.

20. The method of claim 6, wherein in step b) detecting of tyrosine phosphorylated Stat5 localized in cancer cell nuclei comprised detecting binding of said antibody in said cancer cell nuclei in said breast tissue sample.

* * * * *